United States Patent
Chen et al.

(10) Patent No.: US 9,745,363 B2
(45) Date of Patent: Aug. 29, 2017

(54) COMPOSITIONS AND METHODS FOR INHIBITING THROMBOGENESIS

(71) Applicant: NATIONAL UNIVERSITY OF SINGAPORE, Singapore (SG)

(72) Inventors: Wan Chen, Singapore (SG); Tse Siang Kang, Singapore (SG); Manjunatha Ramachandra Kini, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 14/901,517

(22) PCT Filed: Jul. 1, 2014

(86) PCT No.: PCT/SG2014/000315
§ 371 (c)(1),
(2) Date: Dec. 28, 2015

(87) PCT Pub. No.: WO2015/002611
PCT Pub. Date: Jan. 8, 2015

(65) Prior Publication Data
US 2016/0152689 A1 Jun. 2, 2016

Related U.S. Application Data

(60) Provisional application No. 61/841,642, filed on Jul. 1, 2013.

(51) Int. Cl.
*A61K 38/00* (2006.01)
*A61K 38/16* (2006.01)
*C07K 14/00* (2006.01)
*C07K 14/81* (2006.01)
*C12N 9/64* (2006.01)

(52) U.S. Cl.
CPC ........ *C07K 14/8114* (2013.01); *C12N 9/6443* (2013.01); *A61K 38/00* (2013.01)

(58) Field of Classification Search
CPC ........ A61K 38/00; A61K 38/16; C07K 14/00; C07K 14/8114; C07K 14/81; C12N 9/6443
USPC .......................................... 514/14.2; 530/324
See application file for complete search history.

(56) References Cited

U.S. PATENT DOCUMENTS 6,979,538 B2 * 12/2005 Ladner .................. C07K 1/047
                                                              435/4
2006/0134087 A1    6/2006 Ley et al.
2009/0036647 A1    2/2009 Morita
2009/0285825 A1   11/2009 Kini et al.

FOREIGN PATENT DOCUMENTS

WO    WO 2007/018475 A1    2/2007

OTHER PUBLICATIONS

UniProt VKT9 from UniProtKB, pp. 1-7. Integrated into UniProtKB on May 1, 1992.*
Notification Concerning Transmittal of International Preliminary Report on Patentability for International Application No. PCT/SG2014/000315, Compositions and Methods for Inhibiting Thrombogenesis; dated Jan. 14, 2016.
Chen, W., et al., "Fasxiator, a novel factor XIa inhibitor from snake venom, and its site-specific mutagenesis to improve potency and selectivity", *Journal of Thrombosis and Haemostasis*, 13: 248-261 (2014).
Chen, C., et al., "Solution structure of a Kunitz-type chymotrypsin inhibitor isolated from the elapid snake *Bungarus fasciatus*" *J Biol Chem*, 2001. 276(48): p. 45079-87.
Cheng, Q., et al., "A role for factor XIIa-mediated factor XI activation in thrombus formation in vivo" *Blood*, 2010. 116(19): p. 3981-9.
International Search Report and Written Opinion issued in International Application No. PCT/SG2014/000315, entitled "Compositions and Methods for Inhibiting Thrombogenesis," dated Oct. 8, 2014 (10 pages).
Crosby, J. R., et al., "Antithrombotic Effect of Antisense Factor XI oligonucleotide Treatment in Primates", *Arterioscler Thromb Vast Biol*. 33(7): 1670-1678 (Jul. 2013).
Cunningham, B., et al., "High-Resolution Epitope Mapping of hGH-Receptor Interactions by Alanine-Scanning Mutagenesis", *Science*, 244:1081-1085 (1989).
Danalev, D., "Inhibitors of Serine Proteinases from Blood Coagulation Cascade—View on Current Developments," *Mini Rev Med Chem*. 12(8):721-730 (2012).
De Vos, et al., "Human Growth Hormone and Extracellular Domain of Its Receptor: Crystal Structure of the Complex" *Science*, 255:306-312 (1992).
Deng, H., et al., "Synthesis, SAR exploration, and X-ray crystal structures of factor XIa inhibitors containing an alpha-ketothiazole arginine" *Bioorg Med Chem Lett*, 2006. 16(11): p. 3049-54.
Johari, V. and Loke, C., "Brief Overview of the Coagulation Cascade," *Dis Mon*. 58(8):421-423 (2012).
Lazarova, T.I., et al., "Synthesis and in vitro biological evaluation of aryl boronic acids as potential inhibitors of factor XIa" *Bioorg Med Chem Lett*, 2006. 16(19): p. 5022-7.
Lin, J., et al., "Design, synthesis, and biological evaluation of peptidomimctic inhibitors of factor XIa as novel anticoagulants" *J Med Chem*, 2006. 49(26): p. 7781-91.

(Continued)

*Primary Examiner* — Julie Ha
(74) *Attorney, Agent, or Firm* — Hamilton, Brook, Smith & Reynolds, P.C.

(57) ABSTRACT

The invention is directed to a composition comprising an (one or more) isolated peptide comprising a BF01 peptide, variants of a BF01 peptide and/or mutants of a BF01 peptide. In particular aspects, the composition is a pharmaceutical composition. The composition(s) can be used to inhibit thrombogenesis, selectively inhibit the intrinsic pathway of blood coagulation and selectively inhibit FX1 in an individual in need thereof comprising administering an effective amount of all or a biologically active portion of a BF01 peptide, one or more variants thereof and/or one or more mutants thereof.

19 Claims, 28 Drawing Sheets

(56) References Cited

OTHER PUBLICATIONS

Muller, F., et al., "Factor XI and XII as antithrombotic targets" *Curr Opin Hematol*, 2011. 18(5): p. 349-55.

Navaneetham D., "Structural and mutational analyses of the molecular interactions between the catalytic domain of factor XIa and the Kunitz protease inhibitor domain of protease nexin 2", *J. Biol. Chem*, 280(43): 36165-36175 (2005).

Peter, K. and Lip, G.Y., "Thrombosis and cardiovascular disease: Exciting perspectives in cardiovascular prevention and therapy," *Thromb Haemost*, 103(5):875-876 (2010).

Salomon, O., et al., "Patients with severe factor XI deficiency have a reduced incidence of deep-vein thrombosis" *Thromb Haemost*, 2011. 105(2): p. 269-73.

Salomon, O., et al., "Reduced incidence of ischemic stroke in patients with severe factor XI deficiency" *Blood*, 2008. 111(8): p. 4113-7.

Schumacher, W.A., et al., "Inhibition of factor XIa as a new approach to anticoagulation" *Arterioscler Thromb Vasc Biol*, 2010. 30(3): p. 388-92.

Smith, et al., "Human Interleukin 4—The Solution Structure of a Four-helix Bundle Protein", *J. Mol. Biol.* 224:899-904 (1992).

Tucker, E.I., et al., "Prevention of vascular graft occlusion and thrombus-associated thrombin generation by inhibition of factor XI" *Blood*, 2009. 113(4): p. 936-44.

Van Montfoort, M.L. et al., "Anticoagulation beyond direct thrombin and factor Xa inhibitors: indications for targeting the intrinsic pathway?" *Thromb Haemost*, 2013. 110(2).

Wang, X., et al., "Effects of factor XI deficiency on ferric chloride-induced vena cava thrombosis in mice" *J Thromb Haemost*, 2006. 4(9): p. 1982-8.

Wong, P.C., et al., "A small-molecule factor XIa inhibitor produces antithrombotic efficacy with minimal bleeding time prolongation in rabbits" *J Thromb Thrombolysis*, 2011. 32(2): p. 129-37.

Zhang, H., et al., "Inhibition of the intrinsic coagulation pathway factor XI by antisense oligonucleotides: a novel antithrombotic strategy with lowered bleeding risk" *Blood*, 2010. 116(22): p. 4684-92.

\* cited by examiner

FIG. 2E

```
BF01      KNRPTFCNLLPETGRCNALIPAFYYNSHLRKCQKFNYGGCGGNANNFKTIDECQRTCAAKYG
KunitzIX  KNRPTFCNLLPETGRCNALIPAFYYNSHLHKCQKFNYGGCGGNANNFKTIDECQRTCAAKYGRSS
PN2KPI    ----EVCSEQAETGPCRAMISRWYFDVTEGKCAPFFYGGCGGNRNNFDTEEYCMAVCGSAI
BPTI      ---RPDFCLEPPYTGPCKARIIRYFYNAKAGLCQTFVYGGCRAKRNNFKSAEDCMRTCGGA
H1Ch1     QRKPSLCYLPKDSGVCYAFFPSFYYDSATRTCRRFIYGGCMGNENRFRSFEECTSVCG
AvKTI     ---KDRCLLPKVTGPCKASLTRYYYDKDTKACVEFIYGGCRGNRNNFKQKDECEKACTDH
BBPTI     HDRPKFCYLPADFGECLAHMRSFYDSESKKCKEFIYGGCHGNANKFPSRDKCRQTCGGK
                   Loop I                       Loop II
```

FIGs. 5A–5B
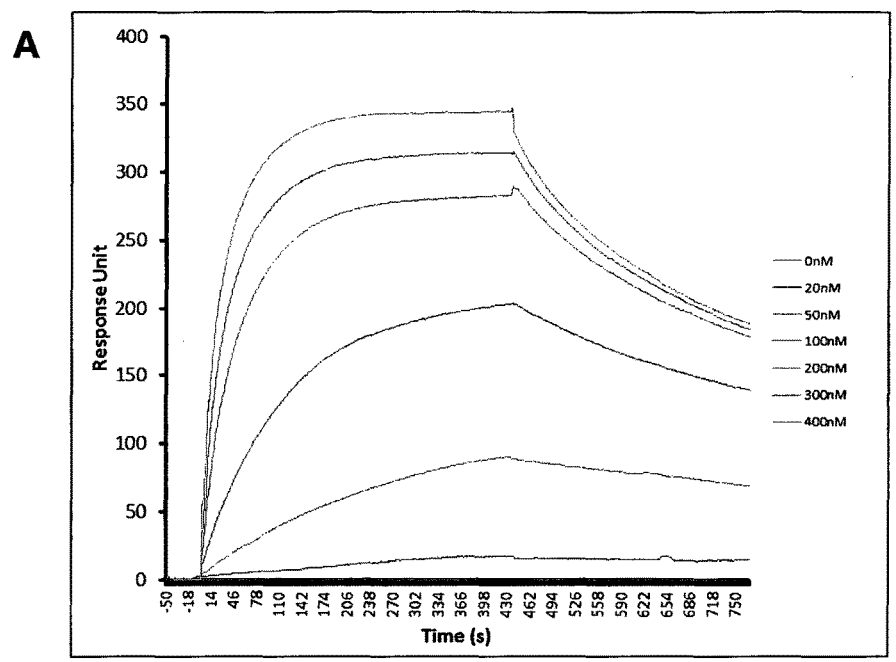
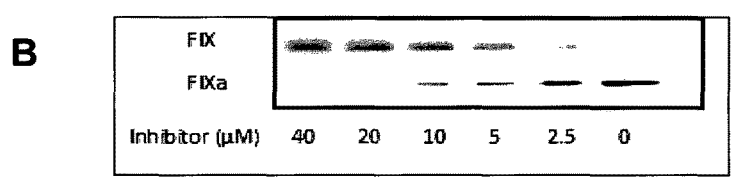
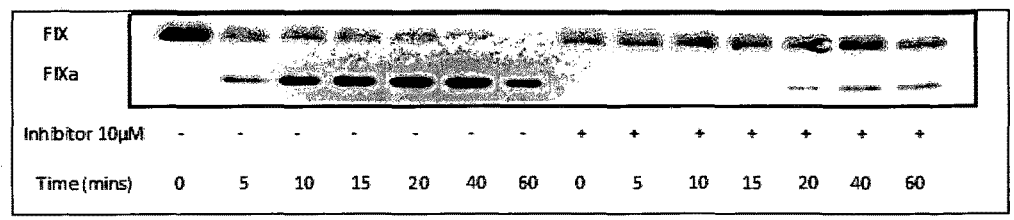

FIG. 8

SEQ ID NO: 1 (native BF01):
KNRPTFCNLLPETGRCNALIPAFYYNSHLRKCQKFNYGGCGGNANNFKTIDECQRTCAAKYG SEQ ID NO: 2 (recombinant BF01):
*GSEFM*KNRPTFCNLLPETGRCNALIPAFYYNSHLRKCQKFNYGGCGGNANNFKTIDECQRTCAAKYG SEQ ID NO: 3 (mutant BF01 N(17)K):
KNRPTFCNLLPETGRC*K*ALIPAFYYNSHLRKCQKFNYGGCGGNANNFKTIDECQRTCAAKYG SEQ ID NO: 4 (mutant BF01 N(17)R):
KNRPTFCNLLPETGRC*R*ALIPAFYYNSHLRKCQKFNYGGCGGNANNFKTIDECQRTCAAKYG SEQ ID NO: 5 (mutant BF01 N(36)F):
KNRPTFCNLLPETGRCNALIPAFYYNSHLRKCQKF*F*YGGCGGNANNFKTIDECQRTCAAKYG SEQ ID NO: 6 (mutant BF01 L(19)A):
KNRPTFCNLLPETGRCNA*A*IPAFYYNSHLRKCQKFNYGGCGGNANNFKTIDECQRTCAAKYG SEQ ID NO: 7 (mutant BF01 L(19)M):
KNRPTFCNLLPETGRCNA*M*IPAFYYNSHLRKCQKFNYGGCGGNANNFKTIDECQRTCAAKYG SEQ ID NO: 8 (mutant BF01 R(15)A):
KNRPTFCNLLPETG*A*CNALIPAFYYNSHLRKCQKFNYGGCGGNANNFKTIDECQRTCAAKYG SEQ ID NO: 9 (mutant BF01 Y(24)A):
KNRPTFCNLLPETGRCNALIPAF*A*YNSHLRKCQKFNYGGCGGNANNFKTIDECQRTCAAKYG

FIG. 8 continued

SEQ ID NO: 10 (mutant BF01 P(21)R:

KNRPTFCNLLPETGRCNALI*R*AFYYNSHLRKCQKFNYGGCGGNANNFKTIDECQRTCAAKYG

SEQ ID NO: 11 (mutant BF01 R(15)P):

KNRPTFCNLLPETG*P*CNALIPAFYYNSHLRKCQKFNYGGCGGNANNFKTIDECQRTCAAKYG

SEQ ID NO: 12 (mutant BF01 N(17)R, L(19)E):

KNRPTFCNLLPETGRC*RA*E*I*PAFYYNSHLRKCQKFNYGGCGGNANNFKTIDECQRTCAAKYG

SEQ ID NO: 40

KNRPTFCNLLPETG*X*C*XA*X*lX*AF*X*YNSHLRKCQKF*X*YGGCGGNANNFKTIDECQRTCAAKYG where X at position 15 is R, A or P; X at position 17 is N, K, or R; X at position 19 is L, A, M, E, F, N, R, or S; X at position 21 is P or R; X at position 24 is Y or A; and/or X at position 36 is N or F.

FIGs. 9G-9L
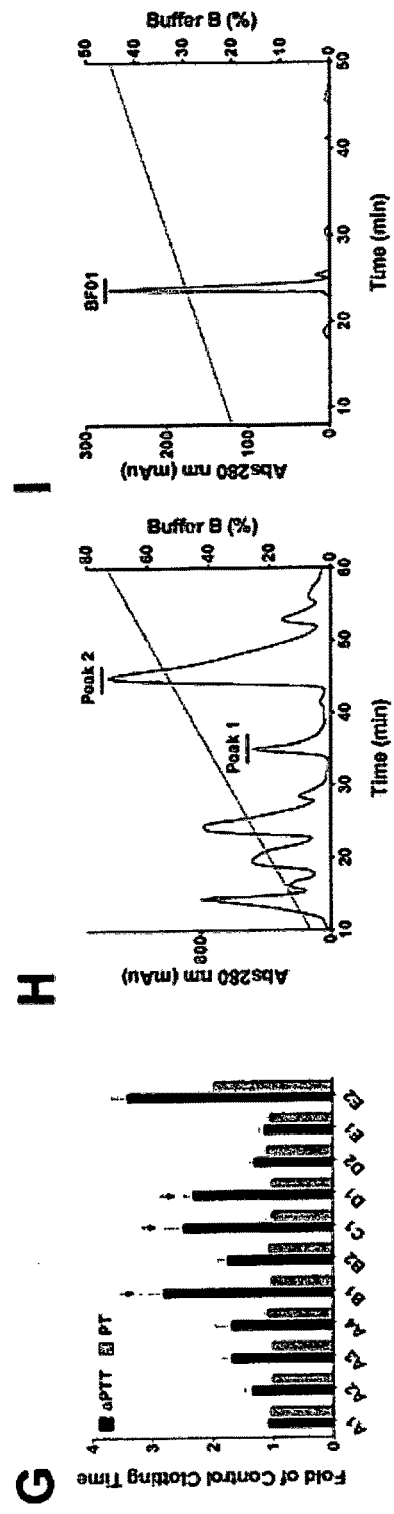
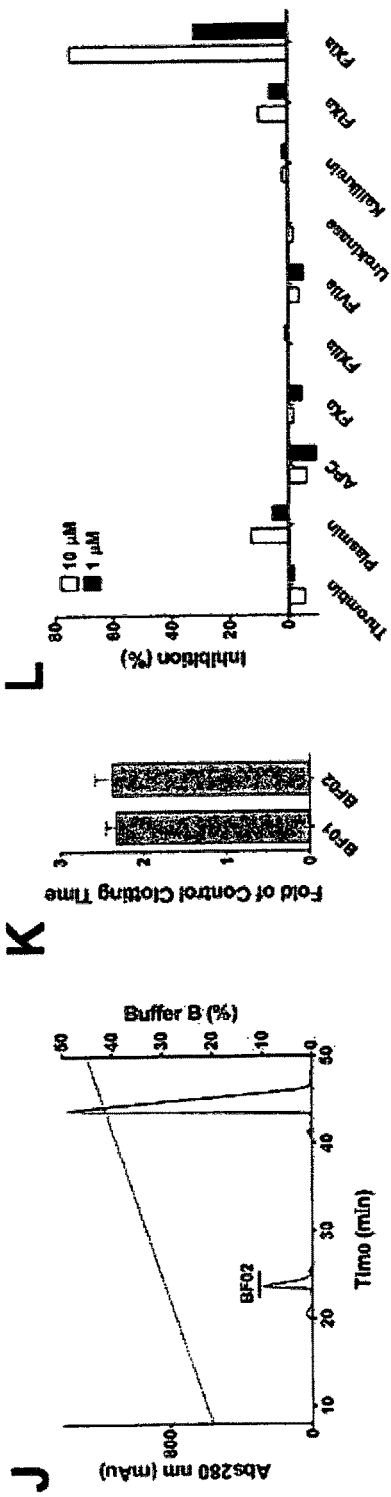

SEQUENCE LISTING

<160> NUMBER OF SEQ ID NOS: 40

<210> SEQ ID NO 1
<211> LENGTH: 62
<212> TYPE: PRT
<213> ORGANISM: Bungarus fasciatus

<400> SEQUENCE: 1

Lys Asn Arg Pro Thr Phe Cys Asn Leu Leu Pro Glu Thr Gly Arg Cys
1 5 10 15

Asn Ala Leu Ile Pro Ala Phe Tyr Tyr Asn Ser His Leu Arg Lys Cys
20 25 30

Gln Lys Phe Asn Tyr Gly Gly Cys Gly Gly Asn Ala Asn Asn Phe Lys
35 40 45

Thr Ile Asp Glu Cys Gln Arg Thr Cys Ala Ala Lys Tyr Gly
50 55 60

<210> SEQ ID NO 2
<211> LENGTH: 67
<212> TYPE: PRT
<213> ORGANISM: Artificial Sequence
<220> FEATURE:
<223> OTHER INFORMATION: recombinant BF01

<400> SEQUENCE: 2

Gly Ser Glu Phe Met Lys Asn Arg Pro Thr Phe Cys Asn Leu Leu Pro
1 5 10 15

Glu Thr Gly Arg Cys Asn Ala Leu Ile Pro Ala Phe Tyr Tyr Asn Ser
20 25 30

His Leu Arg Lys Cys Gln Lys Phe Asn Tyr Gly Gly Cys Gly Gly Asn
35 40 45

Ala Asn Asn Phe Lys Thr Ile Asp Glu Cys Gln Arg Thr Cys Ala Ala
50 55 60

Lys Tyr Gly
65

<210> SEQ ID NO 3
<211> LENGTH: 62
<212> TYPE: PRT
<213> ORGANISM: Artificial Sequence
<220> FEATURE:
<223> OTHER INFORMATION: mutant BF01 N(17)K

<400> SEQUENCE: 3

Lys Asn Arg Pro Thr Phe Cys Asn Leu Leu Pro Glu Thr Gly Arg Cys
1               5                   10                  15

Lys Ala Leu Ile Pro Ala Phe Tyr Tyr Asn Ser His Leu Arg Lys Cys
            20                  25                  30

Gln Lys Phe Asn Tyr Gly Gly Cys Gly Gly Asn Ala Asn Asn Phe Lys
        35                  40                  45

Thr Ile Asp Glu Cys Gln Arg Thr Cys Ala Ala Lys Tyr Gly
    50                  55                  60

<210> SEQ ID NO 4
<211> LENGTH: 62
<212> TYPE: PRT
<213> ORGANISM: Artificial Sequence
<220> FEATURE:
<223> OTHER INFORMATION: mutant BF01 N(17)R

<400> SEQUENCE: 4

Lys Asn Arg Pro Thr Phe Cys Asn Leu Leu Pro Glu Thr Gly Arg Cys
1               5                   10                  15

Arg Ala Leu Ile Pro Ala Phe Tyr Tyr Asn Ser His Leu Arg Lys Cys
            20                  25                  30

Gln Lys Phe Asn Tyr Gly Gly Cys Gly Gly Asn Ala Asn Asn Phe Lys
        35                  40                  45

Thr Ile Asp Glu Cys Gln Arg Thr Cys Ala Ala Lys Tyr Gly
    50                  55                  60

<210> SEQ ID NO 5
<211> LENGTH: 62
<212> TYPE: PRT
<213> ORGANISM: Artificial Sequence
<220> FEATURE:
<223> OTHER INFORMATION: mutant BF01 N(36)F

<400> SEQUENCE: 5

Lys Asn Arg Pro Thr Phe Cys Asn Leu Leu Pro Glu Thr Gly Arg Cys
1               5                   10                  15

Asn Ala Leu Ile Pro Ala Phe Tyr Tyr Asn Ser His Leu Arg Lys Cys
            20                  25                  30

Gln Lys Phe Phe Tyr Gly Gly Cys Gly Gly Asn Ala Asn Asn Phe Lys
        35                  40                  45

Thr Ile Asp Glu Cys Gln Arg Thr Cys Ala Ala Lys Tyr Gly
    50                  55                  60

<210> SEQ ID NO 6
<211> LENGTH: 62
<212> TYPE: PRT
<213> ORGANISM: Artificial Sequence
<220> FEATURE:
<223> OTHER INFORMATION: mutant BF01 L(19)A

<400> SEQUENCE: 6

Lys Asn Arg Pro Thr Phe Cys Asn Leu Leu Pro Glu Thr Gly Arg Cys
1               5                   10                  15

Asn Ala Ala Ile Pro Ala Phe Tyr Tyr Asn Ser His Leu Arg Lys Cys
            20                  25                  30

Gln Lys Phe Asn Tyr Gly Gly Cys Gly Gly Asn Ala Asn Asn Phe Lys
        35                  40                  45

Thr Ile Asp Glu Cys Gln Arg Thr Cys Ala Ala Lys Tyr Gly
    50                  55                  60

<210> SEQ ID NO 7
<211> LENGTH: 62
<212> TYPE: PRT
<213> ORGANISM: Artificial Sequence
<220> FEATURE:
<223> OTHER INFORMATION: mutant BF01 L(19)M

<400> SEQUENCE: 7

Lys Asn Arg Pro Thr Phe Cys Asn Leu Leu Pro Glu Thr Gly Arg Cys
1               5                   10                  15

Asn Ala Met Ile Pro Ala Phe Tyr Tyr Asn Ser His Leu Arg Lys Cys
            20                  25                  30

Gln Lys Phe Asn Tyr Gly Gly Cys Gly Gly Asn Ala Asn Phe Lys
        35                  40                  45

Thr Ile Asp Glu Cys Gln Arg Thr Cys Ala Ala Lys Tyr Gly
    50                  55                  60

<210> SEQ ID NO 8
<211> LENGTH: 62
<212> TYPE: PRT
<213> ORGANISM: Artificial Sequence
<220> FEATURE:
<223> OTHER INFORMATION: mutant BF01 R(15)A

<400> SEQUENCE: 8

Lys Asn Arg Pro Thr Phe Cys Asn Leu Leu Pro Glu Thr Gly Ala Cys
1               5                   10                  15

Asn Ala Leu Ile Pro Ala Phe Tyr Tyr Asn Ser His Leu Arg Lys Cys
            20                  25                  30

Gln Lys Phe Asn Tyr Gly Gly Cys Gly Gly Asn Ala Asn Phe Lys
        35                  40                  45

Thr Ile Asp Glu Cys Gln Arg Thr Cys Ala Ala Lys Tyr Gly
    50                  55                  60

<210> SEQ ID NO 9
<211> LENGTH: 62
<212> TYPE: PRT
<213> ORGANISM: Artificial Sequence
<220> FEATURE:
<223> OTHER INFORMATION: mutant BF01 Y(24)A

<400> SEQUENCE: 9

Lys Asn Arg Pro Thr Phe Cys Asn Leu Leu Pro Glu Thr Gly Arg Cys
1               5                   10                  15

Asn Ala Leu Ile Pro Ala Phe Ala Tyr Asn Ser His Leu Arg Lys Cys
            20                  25                  30

Gln Lys Phe Asn Tyr Gly Gly Cys Gly Gly Asn Ala Asn Phe Lys
        35                  40                  45

Thr Ile Asp Glu Cys Gln Arg Thr Cys Ala Ala Lys Tyr Gly
    50                  55                  60

<210> SEQ ID NO 10
<211> LENGTH: 62
<212> TYPE: PRT
<213> ORGANISM: Artificial Sequence
<220> FEATURE:
<223> OTHER INFORMATION: mutant BF01 P(21)R

<400> SEQUENCE: 10

Lys Asn Arg Pro Thr Phe Cys Asn Leu Leu Pro Glu Thr Gly Arg Cys
1               5                   10                  15

Asn Ala Leu Ile Arg Ala Phe Tyr Tyr Asn Ser His Leu Arg Lys Cys
            20                  25                  30

Gln Lys Phe Asn Tyr Gly Gly Cys Gly Gly Asn Ala Asn Asn Phe Lys
            35                  40                  45

Thr Ile Asp Glu Cys Gln Arg Thr Cys Ala Ala Lys Tyr Gly
    50                  55                  60

<210> SEQ ID NO 11
<211> LENGTH: 62
<212> TYPE: PRT
<213> ORGANISM: Artificial Sequence
<220> FEATURE:
<223> OTHER INFORMATION: mutant BF01 R(15)P

<400> SEQUENCE: 11

Lys Asn Arg Pro Thr Phe Cys Asn Leu Leu Pro Glu Thr Gly Pro Cys
1               5                   10                  15

Asn Ala Leu Ile Pro Ala Phe Tyr Tyr Asn Ser His Leu Arg Lys Cys
            20                  25                  30

Gln Lys Phe Asn Tyr Gly Gly Cys Gly Gly Asn Ala Asn Asn Phe Lys
            35                  40                  45

Thr Ile Asp Glu Cys Gln Arg Thr Cys Ala Ala Lys Tyr Gly
    50                  55                  60

<210

```
<212> TYPE: PRT
<213> ORGANISM: Unknown
<220> FEATURE:
<223> OTHER INFORMATION: Kunitz-type protease inhibitor

<400> SEQUENCE: 14

Glu Val Cys Ser Glu Gln Ala Glu Thr Gly Pro Cys Arg Ala Met Ile
 1               5                  10                  15

Ser Arg Trp Tyr Phe Asp Val Thr Glu Gly Lys Cys Ala Pro Phe Phe
             20                  25                  30

Tyr Gly Gly Cys Gly Gly Asn Arg Asn Asn Phe Asp Thr Glu Glu Tyr
         35                  40                  45

Cys Met Ala Val Cys Gly Ser Ala Ile
 50                  55

<210> SEQ ID NO 15
<211> LENGTH: 57
<212> TYPE: PRT
<213> ORGANISM: Unknown
<220> FEATURE:
<223> OTHER INFORMATION: Kunitz-type protease inhibitor

<400> SEQUENCE: 15

Arg Pro Asp Phe Cys Leu Glu Pro Pro Tyr Gly Pro Cys Lys Ala Arg
 1               5                  10                  15

Ile Ile Arg Tyr Phe Tyr Asn Ala Lys Ala Gly Leu Cys Gln Thr Phe
             20                  25                  30

Val Tyr Gly Gly Cys Arg Ala Lys Arg Asn Asn Phe Lys Ser Ala Glu
         35                  40                  45

Asp Cys Met Arg Thr Cys Gly Gly Ala
 50                  55

<210> SEQ ID NO 16
<211> LENGTH: 58
<212> TYPE: PRT
<213> ORGANISM: Unknown
<220> FEATURE:
<223> OTHER INFORMATION: Kunitz-type protease inhibitor

<400> SEQUENCE: 16

Gln Arg Lys Pro Ser Leu Cys Tyr Leu Pro Lys Asp Ser Gly Val Cys
 1               5                  10                  15

Tyr Ala Phe Phe Pro Ser Phe Tyr Tyr Asp Ser Ala Thr Arg Thr Cys
             20                  25                  30

Arg Arg Phe Ile Tyr Gly Gly Cys Met Gly Asn Glu Asn Arg Phe Arg
         35                  40                  45

Ser Phe Glu Glu Cys Thr Ser Val Cys Gly
 50                  55

<210> SEQ ID NO 17
<211> LENGTH: 57
<212> TYPE: PRT
<213> ORGANISM: Unknown
<220> FEATURE:
<223> OTHER INFORMATION: Kunitz-type protease inhibitor

<400> SEQUENCE: 17

Lys Asp Arg Cys Leu Leu Pro Lys Val Thr Gly Pro Cys Lys Ala Ser
 1               5                  10                  15

Leu Thr Arg Tyr Tyr Tyr Asp Lys Asp Thr Lys Ala Cys Val Glu Phe
             20                  25                  30
```

Ile Tyr Gly Gly Cys Arg Gly Asn Arg Asn Phe Lys Gln Lys Asp
        35                  40                  45

Glu Cys Glu Lys Ala Cys Thr Asp His
 50                  55

<210> SEQ ID NO 18
<211> LENGTH: 60
<212> TYPE: PRT
<213> ORGANISM: Unknown
<220> FEATURE:
<223> OTHER INFORMATION: Kunitz-type protease inhibitor

<400> SEQUENCE: 18

His Asp Arg Pro Lys Phe Cys Tyr Leu Pro Ala Asp Pro Gly Glu Cys
 1               5                  10                  15

Leu Ala His Met Arg Ser Phe Tyr Tyr Asp Ser Glu Ser Lys Lys Cys
                20                  25                  30

Lys Glu Phe Ile Tyr Gly Gly Cys His Gly Asn Ala Asn Lys Phe Pro
                35                  40                  45

Ser Arg Asp Lys Cys Arg Gln Thr Cys Gly Gly Lys
 50                  55                  60

<210> SEQ ID NO 19
<211> LENGTH: 65
<212> TYPE: PRT
<213> ORGANISM: Bungarus fasciatus

<400> SEQUENCE: 19

Lys Asn Arg Pro Thr Phe Cys Asn Leu Leu Pro Glu Thr Gly Arg Cys
 1               5                  10                  15

Asn Ala Leu Ile Pro Ala Phe Tyr Tyr Asn Ser His Leu Arg Lys Cys
                20                  25                  30

Gln Lys Phe Asn Tyr Gly Gly Cys Gly Gly Asn Ala Asn Asn Phe Lys
                35                  40                  45

Thr Ile Asp Glu Cys Gln Arg Thr Cys Ala Ala Lys Tyr Gly Arg Ser
 50                  55                  60

Ser
65

<210> SEQ ID NO 20
<211> LENGTH: 65
<212> TYPE: PRT
<213> ORGANISM: Unknown
<220> FEATURE:
<223> OTHER INFORMATION: Kunitz-type protease inhibitor

<400> SEQUENCE: 20

Lys Asn Arg Pro Thr Phe Cys Asn Leu Leu Pro Glu Thr Gly Arg Cys
 1               5                  10                  15

Asn Ala Leu Ile Pro Ala Phe Tyr Tyr Asn Ser His Leu His Lys Cys
                20                  25                  30

Gln Lys Phe Asn Tyr Gly Gly Cys Gly Gly Asn Ala Asn Asn Phe Lys
                35                  40                  45

Thr Ile Asp Glu Cys Gln Arg Thr Cys Ala Ala Lys Tyr Gly Arg Ser
 50                  55                  60

Ser
65

<210> SEQ ID NO 21
<211> LENGTH: 22

<212> TYPE: PRT
<213> ORGANISM: Bungarus fasciatus

<400> SEQUENCE: 21

Lys Asn Arg Pro Thr Phe Cys Asn Leu Leu Pro Glu Thr Gly Arg Cys
1               5                   10                  15

Asn Ala Leu Ile Pro Ala
            20

<210> SEQ ID NO 22
<211> LENGTH: 39
<212> TYPE: PRT
<213> ORGANISM: Bungarus fasciatus

<400> SEQUENCE: 22

Lys Asn Arg Pro Thr Phe Cys Asn Leu Leu Pro Glu Thr Gly Arg Cys
1               5                   10                  15

Asn Ala Leu Ile Pro Ala Phe Tyr Tyr Asn Ser His Leu Arg Lys Cys
            20                  25                  30

Gln Lys Phe Asn Tyr Gly Gly
        35

<210> SEQ ID NO 23
<211> LENGTH: 25
<212> TYPE: PRT
<213> ORGANISM: Bungarus fasciatus

<400> SEQUENCE: 23

Lys Cys Gln Lys Phe Asn Tyr Gly Gly Cys Gly Gly Asn Ala Asn Asn
1               5                   10                  15

Phe Lys Thr Ile Asp Glu Cys Gln Arg
            20                  25

<210> SEQ ID NO 24
<211> LENGTH: 10
<212> TYPE: PRT
<213> ORGANISM: Bungarus fasciatus

<400> SEQUENCE: 24

Thr Cys Ala Ala Lys Tyr Gly Arg Ser Ser
1               5                   10

<210> SEQ ID NO 25
<211> LENGTH: 12
<212> TYPE: PRT
<213> ORGANISM: Bungarus fasciatus

<400> SEQUENCE: 25

Pro Thr Phe Cys Asn Leu Leu Pro Glu Thr Gly Arg
1               5                   10

<210> SEQ ID NO 26
<211> LENGTH: 25
<212> TYPE: PRT
<213> ORGANISM: Bungarus fasciatus

<400> SEQUENCE: 26

Lys Cys Gln Lys Phe Asn Tyr Gly Gly Cys Gly Gly Asn Ala Asn Asn
1               5                   10                  15

Phe Lys Thr Ile Asp Glu Cys Gln Arg
            20                  25

```
<210> SEQ ID NO 27
<211> LENGTH: 15
<212> TYPE: PRT
<213> ORGANISM: Bungarus fasciatus

<400> SEQUENCE: 27

Cys Asn Ala Leu Ile Pro Ala Phe Tyr Tyr Asn Ser His Leu Arg
1               5                   10                  15

<210> SEQ ID NO 28
<211> LENGTH: 30
<212> TYPE: PRT
<213> ORGANISM: Bungarus fasciatus

<400> SEQUENCE: 28

Asn Arg Pro Thr Phe Cys Asn Leu Leu Pro Glu Thr Gly Arg Cys Asn
1               5                   10                  15

Ala Leu Ile Pro Ala Phe Tyr Tyr Asn Ser His Leu Arg Lys
            20                  25                  30

<210> SEQ ID NO 29
<211> LENGTH: 12
<212> TYPE: PRT
<213> ORGANISM: Bungarus fasciatus

<400> SEQUENCE: 29

Thr Ile Asp Glu Cys Gln Arg Thr Cys Ala Ala Lys
1               5                   10

<210> SEQ ID NO 30
<211> LENGTH: 14
<212> TYPE: PRT
<213> ORGANISM: Bungarus fasciatus

<400> SEQUENCE: 30

Phe Asn Tyr Gly Gly Cys Gly Gly Asn Ala Asn Asn Phe Lys
1               5                   10

<210> SEQ ID NO 31
<211> LENGTH: 15
<212> TYPE: PRT
<213> ORGANISM: Bungarus fasciatus

<400> SEQUENCE: 31

Lys Asn Arg Pro Thr Phe Cys Asn Leu Leu Pro Glu Thr Gly Arg
1               5                   10                  15

<210> SEQ ID NO 32
<211> LENGTH: 25
<212> TYPE: PRT
<213> ORGANISM: Bungarus fasciatus

<400> SEQUENCE: 32

Lys Cys Gln Lys Phe Asn Tyr Gly Gly Cys Gly Gly Asn Ala Asn Asn
1               5                   10                  15

Phe Lys Thr Ile Asp Glu Cys Gln Arg
            20                  25

<210> SEQ ID NO 33
<211> LENGTH: 12
<212> TYPE: PRT
<213> ORGANISM: Bungarus fasciatus

<400> SEQUENCE: 33
```

```
Pro Thr Phe Cys Asn Leu Leu Pro Glu Thr Gly Arg
1               5                   10
```

```
<210> SEQ ID NO 34
<211> LENGTH: 10
<212> TYPE: PRT
<213> ORGANISM: Bungarus fasciatus

<400> SEQUENCE: 34

Thr Cys Ala Ala Lys Tyr Gly Arg Ser Ser
1               5                   10
```

```
<210> SEQ ID NO 35
<211> LENGTH: 15
<212> TYPE: PRT
<213> ORGANISM: Bungarus fasciatus

<400> SEQUENCE: 35

Cys Asn Ala Leu Ile Pro Ala Phe Tyr Tyr Asn Ser His Leu Arg
1               5                   10                  15
```

```
<210> SEQ ID NO 36
<211> LENGTH: 8
<212> TYPE: PRT
<213> ORGANISM: Bungarus fasciatus

<400> SEQUENCE: 36

Thr Cys Ala Ala Lys Tyr Gly Arg
1               5
```

```
<210> SEQ ID NO 37
<211> LENGTH: 30
<212> TYPE: PRT
<213> ORGANISM: Bungarus fasciatus

<400> SEQUENCE: 37

Asn Arg Pro Thr Phe Cys Asn Leu Leu Pro Glu Thr Gly Arg Cys Asn
1               5                   10                  15

Ala Leu Ile Pro Ala Phe Tyr Tyr Asn Ser His Leu Arg Lys
            20                  25                  30
```

```
<210> SEQ ID NO 38
<211> LENGTH: 14
<212> TYPE: PRT
<213> ORGANISM: Bungarus fasciatus

<400> SEQUENCE: 38

Phe Asn Tyr Gly Gly Cys Gly Gly Asn Ala Asn Asn Phe Lys
1               5                   10
```

```
<210> SEQ ID NO 39
<211> LENGTH: 12
<212> TYPE: PRT
<213> ORGANISM: Bungarus fasciatus

<400> SEQUENCE: 39

Thr Ile Asp Glu Cys Gln Arg Thr Cys Ala Ala Lys
1               5                   10
```

```
<210> SEQ ID NO 40
<211> LENGTH: 62
<212> TYPE: PRT
<213> ORGANISM: Artificial Sequence
<220> FEATURE:
<223> OTHER INFORMATION: mutant BF01
```

```
<220> FEATURE:
<221> NAME/KEY: VARIANT
<222> LOCATION: (15)...(15)
<223> OTHER INFORMATION: Xaa=R,A,orP
<220> FEATURE:
<221> NAME/KEY: VARIANT
<222> LOCATION: (17)...(17)
<223> OTHER INFORMATION: Xaa=N,K,orR
<220> FEATURE:
<221> NAME/KEY: VARIANT
<222> LOCATION: (19)...(19)
<223> OTHER INFORMATION: Xaa=L,A,M,F,N,RorS
<220> FEATURE:
<221> NAME/KEY: VARIANT
<222> LOCATION: (21)...(21)
<223> OTHER INFORMATION: Xaa=PorR
<220> FEATURE:
<221> NAME/KEY: VARIANT
<222> LOCATION: (24)...(24)
<223> OTHER INFORMATION: Xaa=YorA
<220> FEATURE:
<221> NAME/KEY: VARIANT
<222> LOCATION: (36)...(36)
<223> OTHER INFORMATION: Xaa=NorF

<400> SEQUENCE: 40

Lys Asn Arg Pro Thr Phe Cys Asn Leu Leu Pro Glu Thr Gly Xaa Cys
1               5                   10                  15

Xaa Ala Xaa Ile Xaa Ala Phe Xaa Tyr Asn Ser His Leu Arg Lys Cys
            20              25                  30

Gln Lys Phe Xaa Tyr Gly Gly Cys Gly Gly Asn Ala Asn Phe Lys
            35              40              45

Thr Ile Asp Glu Cys Gln Arg Thr Cys Ala Ala Lys Tyr Gly
50              55                  60
```

COMPOSITIONS AND METHODS FOR INHIBITING THROMBOGENESIS

RELATED APPLICATION

This application is the U.S. National Stage of International Application No. PCT/SG2014/000315, filed Jul. 1, 2014, which designates the U.S., published in English, and claims the benefit of U.S. Provisional Application No. 61/841,642, filed Jul. 1, 2013.

The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 44891080002_SEQUENCE_LISTING; created 12/18/2015, 18KB in size.

BACKGROUND OF THE INVENTION

Blood coagulation, also known as thrombogenesis, is an important physiological process that prevents the excessive loss of blood from the body in the events of injury and tissue damage. The process of coagulation is orchestrated largely by the different proteins present in the plasma, in particular, those along a complex cascade of enzymatic reactions, known as the blood coagulation cascade. While physiological formation of clots (thrombus) is critical for hemostasis and preservation of blood volume, abnormal and pathogenic thrombosis is related to a number of cardiovascular diseases [Peter, K. and G. Y. Lip, Thromb Haemost, 2010. 103(5): 875-6].

The blood coagulation cascade is a crucial process for regulating thrombosis and can be divided into three pathways: intrinsic, extrinsic and common pathway [Johan, V. and C. Loke, Dis Mon, 2012. 58(8):421-3]. Protease such as Factor X (FX), thrombin and tissue factor, which participate in the extrinsic and common pathways are the prevailing drug targets for anti-thrombotic design, as the inhibition of these proteins' functions can easily achieve high inhibitory potency in clot formation in blood [Danalev, D., Mini Rev Med Chem, 2012. 12(8): p. 721-30]. However, the current approved drugs targeting these targets are all associated with high risks of excessive bleeding when used for anti-thrombotic purpose.

Therefore, improved anti-coagulent compositions and methods are needed to minimize the most common and severe side effects of excessive bleeding seen in many of the current anti-coagulants seen on the market.

SUMMARY OF THE INVENTION

As described herein, *Bungarus fasciatus* venom was fractionated and examined for effects on prothrombin time (PT) and activated partial thromboplastin time (aPTT) of human plasma. Fractions that prolonged aPTT and left PT unaffected were further analyzed by mass spectrometry, protein sequencing, and circular dichroism spectroscopy and screened for specificity against different coagulation enzymes. Isolated candidate peptide was further characterized by a series of functional assays including inhibition kinetics, western blotting, surface plasmon resonance and blood coagulation assays.

A kunitz-type protease inhibitor (termed BF01 or Fasxiator) showing highly specific inhibition of FXIa was purified. The protein was recombinantly expressed in *Escherichia coli* system, and purified by Ni-NTA beads. A recombinant form of BF01 (rBF01) prolonged aPTT and was demonstrated to interact and inhibit FXIa in a dose- and time-dependent manner, while inhibition of other protease in the coagulation pathways (Kallikrein, FXIIa, FXIa, FXa, FIXa, FVIIa, Urokinase, alpha-Thrombin) were not observed. rBF01's inhibitory effect on the cleavage of FIX by FXIa was observed using western blotting through probing for FIX and FIXa. Mutagenesis analysis of rBF01 was carried out as well, which produced mutants with much higher potency (e.g., about 100-1000 times with one or more residue substitutions).

Therefore, BF01 is a highly specific anticoagulant protein that targets FXIa of the intrinsic pathway, but leaves the extrinsic and common pathway of the coagulation cascade untouched. Thus, BF01 represents a novel anticoagulant with minimal bleeding side effects that is associated with many of the currently approved anticoagulants.

Accordingly, in one aspect, the invention is directed to an (one or more) isolated peptide comprising a BF01 peptide, variants of a BF01 peptide and/or mutants of a BF01 peptide.

In another aspect, the invention is directed to a method of inhibiting thrombogenesis in an individual in need thereof comprising administering an effective amount of all or a biologically active portion of a (one or more) BF01 peptide, one or more variants thereof and/or one or more mutants thereof.

In another aspect, the invention is directed to a method of selectively inhibiting the intrinsic pathway of blood coagulation in an individual in need thereof comprising administering an effective amount of all or a biologically active portion of a (one or more) BF01 peptide, one or more variants thereof and/or one or more mutants thereof.

In yet another aspect, the invention is directed to a method of selectively inhibiting FX1 in an individual in need thereof comprising administering an effective amount of all or a biologically active portion of a (one or more) BF01 peptide, one or more variants thereof and/or one or more mutants thereof.

BRIEF DESCRIPTION OF THE DRAWINGS

FIGS. 2A-2E: (2A) SEC profile of crude venom. The labeled peak contained BF01. (2B) HPLC profile of SEC peak labeled in FIG. 2A. The labeled peak contained BF01. (2C) ESI-MS profile of BF01. BF01 has a molecular weight of 6977.5±0.85. (2D) Circular dichroism spectroscopy of BF01. The profile is consistent with other Kunitz type inhibitors (2E) Sequence alignment of BF01 with other Kunitz type protease inhibitors (SEQ ID NOs: 1 and 13-18).

FIGS. 5A-5D: (5A) Interaction of FXIa with rBF01 was studied by immobilizing rBF01 on a COOH5 chip and running different concentrations of FXIa through the chip surface; (5B) Cleavage of FIX by FXIa in the presence of rBF01; (5C) Cleavage of FIX by FXIa in the presence of rBF01 was monitor by Chromogenic assay. (5D) rBF01's prolongation of aPTT in FXIa deficient plasma W/O external FXI.

FIG. 8: sequences of native BF01 (SEQ ID NO: 1), a recombinant BF01 (SEQ ID NO: 2), and mutant BF01 (SEQ ID NOs: 3-12, and 40).

FIGS. 9A-9M: Identification of novel anticoagulants from *Bungarus fasciatus* venom. (9A) SEC of *B. fasciatus* venom. Crude venom (100 mg) was dissolved in 50 mM Tris-HCl buffer (pH 8.0) and separated on a HiLoad 16/60 Superdex 30 preparative grade column. Fractions (1 ml) were collected and pooled into pools A-E. Individual pools were subfractionated on a RP-HPLC column (9B-9F). Fractions with MW between 5 kDa and 8 kDa (Table 2) were pooled into A1, A2, A3, A4, B1, B2, C1, D1, D2, E1 and E2. (9G) Anticoagulant activities of RP-HPLC fractions. Pooled fractions were evaluated using aPTT and PT in triplicate. Error bars represent standard deviations. Pools B1, C1 and D1 prolonged aPTT without significant effects on PT and were further characterized. MS studies revealed that pools B1, C1 and D1 mainly contain two proteins with molecular weights of 6977.5±0.85 Da and 7307.3±0.67 Da (Table 2). (9H) Pooled SEC fractions containing anticoagulant proteins were loaded on a Bio-Rad S6 cation exchange chromatography column. Peak 1 contained BF01 (MW: 6977.5±0.85 Da) and Peak 2 contained BF02 (MW: 7307.3±0.67 Da). (9I and 9J) BF01 and BF02 were further fractionated using RP-HPLC. Fractions containing BF01 and BF02 were pooled and lyophilized for future use. (9K) BF01 and BF02 prolong aPTT at a final concentration of 3.75 µM. (9L) Effects of BF01 on various procoagulant proteases in the coagulation cascade were evaluated. Results indicate that both proteins are selective inhibitors of FXIa. (9M) Alignment of the protein sequences (SEQ ID NOs: 1 and 14-20) with relevant Kunitz-type inhibitors. Dark grey: Cysteines; Light grey: Loop 1 and Loop 2 residues. The disulfide bridges were shown by solid lines.

FIG. 21A-21C represent for triplicates.

DETAILED DESCRIPTION OF THE INVENTION

Figure 1A:
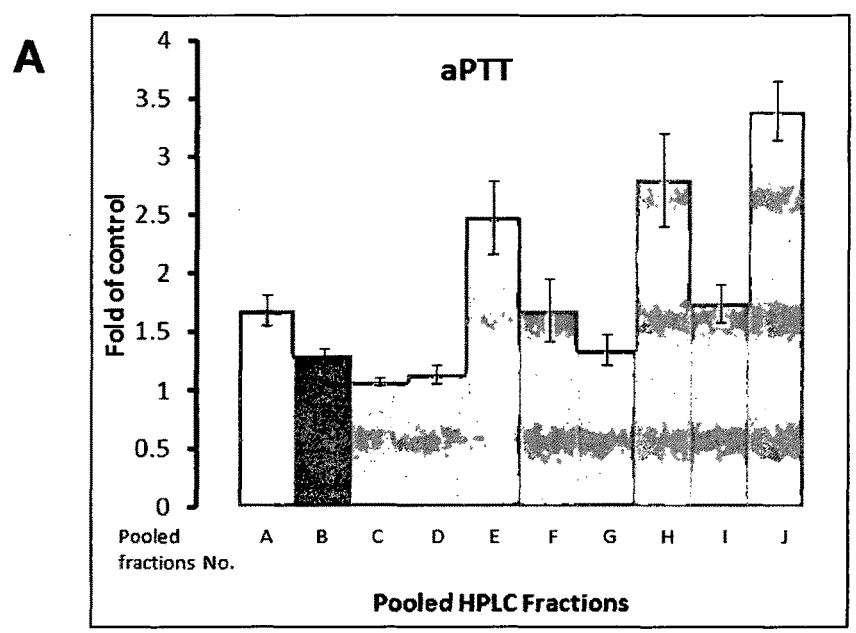
FIGS. 1A-1B: Pooled HPLC fractions with components' molecular weights below 8 KD were checked for prolongation of activated Partial Thromboplastin Time (aPTT) (FIG. 1A) and Prothrombin Time (PT) (FIG. 1B).

Described herein is the identification of a protein (referred to herein as "BF01" or "Fasxiator") from the venom of *Bungarus fasciatus* that inhibits the enzymatic activity of FXIa. Structural analysis revealed that this protein belongs to the Kunitz type inhibitor family. Kunitz type inhibitors/domains are ubiquitously existed in nature. They are relatively small in size, 50-65 amino acids, and structurally characterized by three conserved disulfide bond and two loops that interact with proteases. Interestingly, the physiological inhibitor of FXIa, protease nexin 2, also contains a kunitz domain and the recombinant truncated Kunitz domain (Kunitz protease inhibitor domain of protease nexin-2, in short PN2KPI) preserved the inhibitory activity of PN2 against FXIa [Navaneetham, D., et al., J Biol Chem, 2005. 280(43):36165-75]. In fact, a number of Kunitz type inhibitors are reported to act on important physiological processes and have been well characterized both structurally and functionally.

Surprisingly, the amino acid sequence alignments of BF01 with PN2KPI indicated only 45% identity of the venom protein with PN2KPI. It was of value to explore this venom protein as a small percentage of identity of amino acid sequence with PN2KPI likely means its mode of interaction with FXIa is different from PN2KPI and its surface amino acids are different from PN2KPI which leads to different immunogenicity properties. Further, unlike PN2KPI which is a truncated protein from a significantly larger endogenous protein, BF01 is the first exogenously derived protein that has been shown to inhibit human FXIa.

Factor XI (FXI, FXIa) is an important serine protease in the intrinsic pathway. It has been suggested to play a significant role in thrombosis models such as deep vein thrombosis and ferric chloride induced carotid artery thrombosis [Wang, X., et al., J Thromb Haemost, 2006. 4(9):1982-8; Cheng, Q. et al., Blood, 2010. 116(19):3981-9]. It has also been reported that human beings with elevated levels of plasma FXI experienced higher chance of cerebrovascular events and ischemic stroke [Salomon, O., et al., Blood, 2008. 111(8):4113-7; Salomon, O., et al., Thromb Haemost, 2011. 105(2):269-73]. Interestingly, in contrast to FX and thrombin, disruption of FXI resulted in little bleeding tendency [Muller, F., et al., Curr Opin Hematol, 2011. 18(5): 349-55].

Accordingly, in some aspects, the invention is directed to a composition comprising (consisting essentially of, consisting of) an (one or more) isolated BF01 peptide, variants thereof and/or mutants thereof. In a particular aspect, the BF01 peptide has an amino acid comprising, consisting essentially of, or consisting of SEQ ID NO: 40. In other aspects, the BF01 peptide has an amino acid comprising, consisting essentially of, or consisting of SEQ ID NO: 1. In other aspects, the BF01 peptide has an amino acid comprising, consisting essentially of, or consisting of SEQ ID NO: 2. In other aspects, the BF01 peptide has an amino acid comprising, consisting essentially of, or consisting of SEQ ID NO: 3. In other aspects, the BF01 peptide has an amino acid comprising, consisting essentially of, or consisting of SEQ ID NO: 4. In other aspects, the BF01 peptide has an amino acid comprising, consisting essentially of, or consisting of SEQ ID NO: 12. In yet other aspects, the BF01 peptide has an amino acid comprising, consisting essentially of, or consisting of SEQ ID NO: 5, 6, 7, 8, 9, 10, or 11.

In other aspects, provided herein is a method of inhibiting thrombogenesis in an individual in need thereof comprising (consisting essentially of, consisting of) administering an effective amount of all or a biologically active portion of a (one or more) BF01 peptide (BF01 protein), one or more variants thereof, and/or one or more mutants thereof to the individual.

Thrombogenesis refers to the formation of a blood clot inside a blood vessel, which can obstruct the flow of blood through the circulatory system. When a blood vessel is injured, the body uses platelets (thrombocytes) and fibrin to form a blood clot to prevent blood loss. Even when a blood vessel is not injured, blood clots may form in the body under certain conditions. A clot that breaks free and begins to travel around the body is known as an embolus. Thrombosis can be caused by abnormalities in one or more of the following: the composition of the blood (hypercoagulability or thrombophilia), quality of the vessel wall (endothelial cell injury), and/or nature of the blood flow (stasis, turbulence). Hypercoagulability is caused by, for example, genetic deficiencies or autoimmune disorders. Endothelial cell injury include injury to the vessel's wall by trauma, surgery, infection or turbulent flow at bifurcations. The main mechanism is exposure of tissue factor to the blood coagulation system. Causes of disturbed blood flow include stagnation of blood flow past the point of injury, or venous stasis which may occur in heart failure, in varicose veins or after long periods of sedentary behavior, such as sitting on a long airplane flight. Also, atrial fibrillation, causes stagnant blood in the left atrium (LA) or left atrial appendage (LAA), and can lead to a thromboembolism. Cancers or malignancies such as leukemia may cause increased risk of thrombosis by possible activation of the coagulation system by cancer cells or secretion of procoagulant substances (paraneoplastic syndrome), by external compression on a blood vessel when a solid tumor is present, or (more rarely) extension into the vasculature (for example, renal cell cancers extending into the renal veins). Also, treatments for cancer (radiation, chemotherapy) often cause additional hypercoagulability.

There are at least two distinct forms of thrombosis, venous thrombosis and arterial thrombosis, each of which can be presented by several subtypes. Venous thrombosis is the formation of a thrombus (blood clot) within a vein. There are several diseases which can be classified under this category such as: (1) deep vein thrombosis which is the formation of a blood clot within a deep vein. It most commonly affects leg veins, such as the femoral vein. Three factors are important in the formation of a blood clot within a deep vein—these are the rate of blood flow, the thickness of the blood and qualities of the vessel wall. Classical signs of DVT include swelling, pain and redness of the affected area; (2) portal vein thrombosis which can affect the hepatic portal vein, which can lead to portal hypertension and reduction of the blood supply to the liver (e.g., usually has a pathological cause such as pancreatitis, cirrhosis, diverticulitis or cholangiocarcinoma; (3) renal vein thrombosis which is the obstruction of the renal vein by a thrombus. This tends to lead to reduced drainage from the kidney (4) jugular vein thrombosis which is a condition that may occur due to infection, intravenous drug use or malignancy and can have a varying list of complications, including: systemic sepsis, pulmonary embolism, and papilledema; (5) Budd-Chiari syndrome which is the blockage of the hepatic vein or the inferior vena cava. This form of thrombosis presents with abdominal pain, ascites and hepatomegaly; (6) Paget-Schroetter disease which is the obstruction of an upper extremity vein (such as the axillary vein or subclavian vein) by a thrombus; (7) cerebral venous sinus thrombosis which is a rare form of stroke which results from the blockage of the dural venous sinuses by a thrombus; (8) arterial thrombosis which is the formation of a thrombus within an artery; (9) atrial fibrillation, which causes a blood stasis within the atria with easy thrombus formation.

Arterial thrombosis can embolize and is a major cause of arterial embolism, potentially causing infarction of almost any organ in the body. Examples of arterial thrombosis can occur due to (1) stroke which is the rapid decline of brain function due to a disturbance in the supply of blood to the brain (e.g., thrombotic stroke such as large vessel disease and small vessel disease); (2) myocardial infarction which is caused by ischemia, (restriction in the blood supply), often due to the obstruction of a coronary artery by a thrombus; (3) hepatic artery thrombosis usually occurs as a devastating complication after liver transplantation.

In other aspects, the invention is directed to a method of selectively inhibiting the intrinsic pathway of blood coagulation in an individual in need thereof comprising (consisting essentially of, consisting of) administering an effective amount of all or a biologically active portion of a BF01 peptide, one or more variants thereof, and/or one or more mutants thereof to the individual. In particular aspects, administration of the BF01 peptide, one or more variants thereof, and/or one or more mutants thereof to the individual inhibits only the intrinsic pathway of blood coagulation and not the extrinsic and/or common pathways of blood coagulation.

As discussed herein, the blood coagulation cascade is a crucial process for regulating thrombosis and can be divided into three pathways: intrinsic, extrinsic and common pathway [Johari, V. and C. Loke, Dis Mon, 2012. 58(8):421-3]. The pathways are a series of reactions, in which a zymogen (inactive enzyme precursor) of a serine protease and its glycoprotein co-factor are activated to become active components that then catalyze the next reaction in the cascade, ultimately resulting in cross-linked fibrin. The coagulation factors are generally serine proteases (enzymes), which act by cleaving downstream proteins.

In yet other aspects, the invention is directed to a method of selectively inhibiting (partially, completely) FXI in an individual in need thereof comprising (consisting essentially of, consisting of) administering an effective amount of a BF01 peptide, one or more variants thereof, and/or one or more mutants thereof to the individual. In a particular aspect, the BF01 peptide, one or more variants thereof, and/or one or more mutants thereof inhibits the enzymatic activity of FXIa. As discussed herein, FXIa is a serine protease involved in the blood coagulation cascade having FXI as a physiological substrate.

In some aspects, the BF01 peptide of the compositions and methods provided herein comprises an amino acid sequence SEQ ID NO: 40. In other aspects, the BF01 peptide of the compositions and methods provided herein comprises a wild type (naturally occurring; native) BF01 peptide. In a particular aspect, the BF01 peptide comprises an amino acid sequence of SEQ ID NO:1.

In other aspects, the peptide comprises a BF01 variant peptide. A variant BF01 peptide can differ in amino acid sequence by one or more substitutions, deletions, insertions, inversions, fusions, and truncations or a combination of any of these. Further, variant polypeptides can be fully or partially functional (e.g., ability to inhibit FXI) compared to the wild type BF01 peptide. Fully functional variants typically contain only conservative variation or variation in non-critical residues or in non-critical regions. Functional variants can also contain substitution of similar amino acids and/or additional amino acids that result in no change or an insignificant change in function.

Amino acid residues that are essential for function (e.g., ability to inhibit FX1) can be identified by methods described herein and as known in the art, such as site-directed mutagenesis or alanine-scanning mutagenesis (Cunningham et al., Science, 244: 1081-1085 (1989)). The latter procedure introduces a single alanine mutation at each of the residues in the molecule (one mutation per molecule). The resulting mutant molecules are then tested for biological activity in vitro or in vivo. Sites that are critical for polypeptide activity can also be determined by structural analysis, such as crystallization, nuclear magnetic resonance, or photoaffinity labeling (See Smith et al., *J. Mol. Biol.,* 224: 899-904 (1992); and de Vos et al. *Science*, 255: 306-312 (1992)).

In a particular aspect, the variant BF01 peptide is a recombinantly produced BF01 peptide. As shown herein, recombinant expression of the BF01 peptide resulted in a BF01 peptide with extra N terminal sequence (GSEFM) due to expression of the peptide in a vector that bore a thrombin cleavage site. The peptide was expressed with a histidine tag for purification. The histidine tag was subsequently cleaved off by treating with enzyme and the N terminal GSEFM sequence was the left over segment from the cleavage. In some aspects the BF01 variant peptide comprises an amino acid sequence of SEQ ID NO: 2. As will be apparent to those of skill in the art, expression of the (one or more) BF01 peptide using other expression systems (e.g., other vectors) can result in other tags that are attached (e.g., fused) to the BF01 peptide (e.g., at the N terminus, at the C terminus or within the BF01 peptide).

In other aspects, the BF01 peptide is a mutant BF01 peptide that has enhanced, similar (substantially similar) or decreased biological activity (e.g., ability to inhibit FXIa) compared to native BF01 peptide (wild type BF01 peptide). In some aspects, the mutant BF01 peptide has increased (enhanced) activity (e.g., increased ability to inhibit FXIa) compared to the native BF01 peptide. In some aspects, the BF01 mutant has about 20-fold, 40-fold, 60-fold, 80-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold or greater activity compared to native BF01. In particular aspects, the BF01 mutant comprise an amino acid sequence of SEQ ID NO: 3 (BF01 N(17)K). In another aspect, the BF01 mutant comprise an amino acid sequence of SEQ ID NO: 4 (BF01 N(17)R). In another aspect, the BF01 mutant comprise an amino acid sequence of SEQ ID NO: 12 (BF01 N(17)R, L19E),In other aspects, the BF01 mutant comprises BF01 N(36)F (SEQ ID NO: 5): BF01 L(19)A (SEQ ID NO: 6); BF01 L(19)M (SEQ ID NO: 7); BF01 R(15)A (SEQ ID NO: 8); BF01 Y(24)A (SEQ ID NO: 9): BF01 P(21)R (SEQ ID NO: 10); or BF01 R(15)P (SEQ ID NO: 11).

In yet other aspects, the peptide comprises a biologically active portion (biologically active fragment) of a BF01 peptide, variant thereof and/or mutant thereof. As used herein, a biologically active portion of a BF01 peptide, variant thereof and/or mutant thereof includes a portion that retains at least one activity of BF01, e.g., ability to inhibit FXIa. Biologically active portions can be derived from a polypeptide comprising e.g., SEQ ID NO: 1, SEQ ID NO: 2, SEQ ID NO: 3 and/or SEQ ID NO: 4, or from a polypeptide encoded by a nucleic acid molecule that encodes BF01, and/or variant or portion thereof, complements thereof, or other variant thereof. The present invention also encompasses biologically active portions of the BF01 peptide and/or variants thereof.

Biologically active fragments include peptides that are, for example, about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61 more amino acid residues in length.

Fragments can be discrete (not fused to other amino acid residues or polypeptides) or can be fused to one or more components of a polypeptide. Further, several fragments can be comprised within a single larger polypeptide. In one embodiment, a fragment designed for expression in a host can have wild type and/or heterologous pre- and pro-polypeptide regions fused to the amino terminus and/or the carboxyl terminus of the BF01 polypeptide and/or variant or fragment thereof.

Standard molecular biology methods for generating polypeptide fragments are known in the art. Once the fragments are generated, they can be tested for biological activity, using, for example, any of the methods described herein.

The invention also provides chimeric or fusion polypeptides. These comprise a BF01 polypeptide, variant, mutant and/or biologically active portion thereof operatively linked to a heterologous protein or polypeptide having an amino acid sequence not substantially homologous to the polypeptide. "Operatively linked" indicates that the polypeptide and the heterologous protein are fused in-frame. The heterologous protein can be fused to the N-terminus or C-terminus of the polypeptide. In one embodiment, the fusion polypeptide does not affect the function of the polypeptide per se. For example, the fusion polypeptide can be a GST-fusion polypeptide in which the polypeptide sequences are fused to the C-terminus of the GST sequences. Other types of fusion polypeptides include, but are not limited to, enzymatic fusion polypeptides, for example, β-galactosidase fusions, yeast two-hybrid GAL fusions, histidine (e.g., poly-His) fusions, FLAG-tagged fusions and Ig fusions. Such fusion polypeptides can facilitate the visualization and/or purification of recombinant polypeptide. In certain host cells (e.g., mammalian host cells), expression and/or secretion of a polypeptide can be increased by using a heterologous signal sequence. Therefore, in another embodiment, the fusion polypeptide contains a heterologous signal sequence at its N-terminus.

EP-A 0464 533 discloses fusion proteins comprising various portions of immunoglobulin constant regions. The Fc is useful in therapy and diagnosis and thus results, for example, in improved pharmacokinetic properties (EP-A 0232 262). Thus, this invention also encompasses soluble fusion polypeptides containing a polypeptide of the invention and various portions of the constant regions of heavy or light chains of immunoglobulins of various subclass (IgG, IgM, IgA, IgE).

A chimeric or fusion polypeptide can be produced by standard recombinant DNA techniques. For example, DNA fragments coding for the different polypeptide sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., "*Current Protocols in Molecular Biology*," John Wiley & Sons, (1998), the entire teachings of which are incorporated by reference herein). Moreover, many expression vectors are commercially available that already encode a fusion moiety (e.g., a GST protein). A nucleic acid molecule encoding a polypeptide of the invention can be cloned into such an expression vector such that the fusion moiety is linked in-frame to the polypeptide.

Useful biologically active portions include those that retain one or more of the biological activities of the polypeptide (e.g., ability to inhibit FXIa).

In some aspects, the BF01 peptide, variant, mutant and/or biologically active portion thereof is isolated. As used herein, a polypeptide is said to be "isolated," "substantially pure," or "substantially pure and isolated" when it is substantially free of cellular material, when it is isolated from recombinant or non-recombinant cells, or free of chemical precursors or other chemicals when it is chemically synthesized. In addition, a polypeptide can be joined to another polypeptide with which it is not normally associated in a cell (e.g., in a "fusion protein") and still be "isolated," "substantially pure," or "substantially pure and isolated." An isolated, substantially pure, or substantially pure and isolated polypeptide may be obtained, for example, using affinity purification techniques described herein, as well as other techniques described herein and known to those skilled in the art.

The substantially pure, isolated, or substantially pure and isolated BF01 polypeptide, variant, mutant and/or biologically active can be purified from cells that naturally express it, purified from cells that have been altered to express it (recombinant), or synthesized using known protein synthesis methods. In one embodiment, the polypeptide is produced by recombinant DNA techniques. For example, a nucleic acid molecule encoding the polypeptide is cloned into an expression vector, the expression vector is introduced into a host cell, and the polypeptide is expressed in the host cell.

In the methods of the invention, any suitable route of administration can be used to administer, either systemically or locally, a composition comprising, consisting essentially of, or consisting of a BF01 peptide, variant, mutant and/or biologically active portion thereof. As will be apparent to those of skill in the art, the BF01 peptide, variant, mutant and/or biologically active peptide thereof can be administered as a nucleic acid encoding the BF01 peptide, variant, mutant and/or biologically active peptide thereof.

Examples of suitable routes of administration include oral, dietary, topical, transdermal, rectal, parenteral, intraarterial, intravenous, intramuscular, subcutaneous injection, intradermal injection), inhalation (e.g., intrabronchial, intranasal or oral inhalation, intranasal drops), ocular, pulmonary, nasal, gene gun and the like. Administration can be local or systemic as indicated. The preferred mode of administration can vary depending on the particular agent chosen. Suitable dosage forms include tablets, troches, dispersions, suspensions, solutions, capsules, creams, ointments, aerosols, and the like. The mode of administration will vary depending on the particular agent chosen.

The BF01 peptide, variant, mutant and/or biologically active portion thereof can be administered in a single dose (e.g., in a day) or in multiple doses. In addition, the BF01 peptide, variant, mutant and/or biologically active portion thereof can be administered in one or more days (e.g. over several consecutive days or non-consecutive days).

The BF01 peptide, variant, mutant and/or biologically active portion thereof used in the methods described herein can be administered to a subject as part of a pharmaceutical composition. Formulations will vary according to the route of administration selected (e.g., solution, emulsion or capsule). A "pharmaceutical composition" comprises a (one or more) composition or compound described herein as the active ingredient and inert ingredient(s), such as pharmaceutically acceptable excipients, that make up the carrier. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

In one aspect, the therapy or treatment ameliorates the symptoms associated with the condition and/or disease in an individual. In other aspect, the therapy arrests and/or delays onset of the condition and/or disease in the individual. In yet other aspects, the therapy eradicates the condition and/or disease in an individual. In yet other aspects, the treatment lessens the severity or frequency of symptoms of the disease.

As used herein an "individual" refers to an animal, and in a particular aspect, a mammal. Examples of mammals include primates, a canine, a feline, a rodent, and the like. Specific examples include humans, dogs, cats, horses, cows, sheep, goats, rabbits, guinea pigs, rats and mice.

The term "individual in need thereof" refers to an individual who is in need of treatment or prophylaxis as determined by a researcher, veterinarian, medical doctor or other clinician. In one embodiment, an individual in need thereof is a mammal, such as a human.

The need or desire for administration according to the methods of the present invention is determined via the use of well known risk factors. The effective amount of a (one or more) particular compound is determined, in the final analysis, by the physician in charge of the case, but depends on factors such as the exact condition and/or disease to be treated, the severity of the condition and/or disease from which the patient suffers, the chosen route of administration, other drugs and treatments which the patient may concomitantly require, and other factors in the physician's judgment.

An effective amount of a BF01 peptide, variant, mutant and/or biologically active portion thereof is delivered to an individual in need thereof. As used herein, "effective amount" or "therapeutically effective amount" means an amount of the active compound that will elicit the desired biological or medical response in a tissue, system, subject, or individual, e.g., human, which includes alleviation of the symptoms, in whole or in part, of the condition and/or disease being treated.

The composition can be administered in a single dose (e.g., in a day) or in multiple doses. In addition, the composition can be administered in one or more days (e.g. over several consecutive days or non-consecutive days).

In other aspects, the invention is directed to pharmaceutical compositions comprising one or more BF01 peptides, variants, mutants and/or biologically active portions thereof described herein and/or nucleic acids that encode one or more BF01 peptides, variants, mutants and/or biologically active portions thereof described herein. The pharmaceutical compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrrolidone, sodium saccharine, cellulose, magnesium carbonate, etc.

The pharmaceutical compositions of this invention can also be administered as part of a combinatorial therapy with other compounds. The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The compound may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air. In addition, or alternatively, long-term use of continuous infusion e.g., using Alzet pumps, dermal patches and slow release formulations can be used.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The compounds are administered in a therapeutically effective amount. The amount of compounds that will be therapeutically effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms of an angiogenic disease, a vascular disease, a heart disease, or a circulatory disease, and should be decided according to the judgment of a practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, that notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the compounds can be separated, mixed together in any combination, present in a single vial or tablet. Compounds assembled in a blister pack or other dispensing means is preferred. For the purpose of this invention, unit dosage is intended to mean a dosage that is dependent on the individual pharmacodynamics of each compound and administered in FDA approved dosages in standard time courses.

In particular aspects, the invention is directed to a pharmaceutical composition comprising SEQ ID NO: 1, 2, 3, 4, 5, 6, 7, 8, 9, 10, 11, 12, 40 variants thereof, mutants thereof, biologically active fragments thereof and combinations thereof.

EXEMPLIFICATION

Example 1

Materials and Methods

Thromboplastin-D and APTT-XL were purchased from Pacific Hemostasis, Thermo Scientific (Waltham, Mass., USA). Thrombin from bovine plasma was purchased from Merck Millipore (Darmstadt, Germany). FVIIa, FIXa, FXa, FXIa, activated protein C, plasmin and thrombin were purchased from Hematologic Technologies (Essex Junction, Vt., USA). FXIIa, kallikrein, trypsin and urokinase were purchased from Calbiochem, EMD Millipore (Billerica, Mass., USA). Phosphatidylcholine and phosphatidylserine were purchased from Avanti Polar Lipids Inc (Alabaster, Ala., USA). Chromogenic substrates N-Benzoyl-L-isoleucyl-L-glutamyl-glycyl-L-arginine-p-nitroaniline hydrochloride and its methyl ester (S-2222), H-D-Phenylalanyl-L-pipecolyl-L-arginine-p-nitroaniline dihydrochloride (S-2238), H-D-Valyl-L-leucyl-L-lysine-p-nitroaniline dihydrochloride (S-2251), H-D-Isoleucyl-L-prolyl-L-arginine-p-nitroaniline dihydrochloride (S-2288), H-D-Prolyl-L-phenylalanyl-L-arginine-p-nitroaniline dihydrochloride (S-2302), L-Pyroglutamyl-L-prolyl-L-arginine-p-nitroaniline hydrochloride (S-2366), L-Pyroglutamyl-glycyl-L-arginine-p-nitroaniline hydrochloride (S-2444), and 3-Carbomethoxypropionyl-L-arginyl-L-prolyl-L-tyrosine-p-nitroaniline hydrochloride (S-2586) were purchased from DiaPharma (Westchester, Ohio, USA). D-leucyl-phenylglycyl-arginine-para-nitroanilide diacetate (Spectrozyme FIXa) were purchased from Sekisui Diagnostics (Stanford, Conn., USA).

40% acrylamide, diothiothreitol and Coomassie brilliant blue R-250 were purchased from Bio Rad Laboratories (Hercules, Calif., USA). Ammonia persulphate (APS) was purchased from AppliChem GmbH (Darmstadt, Germany). TEMED was purchased from MP Biomedicals (Solon, Ohio, USA). Tris-glycine SDS buffer were purchased from 1st Base (Singapore). Tris and Guanidine HCl were purchased from Alfa Aesar (Ward Hill, Mass., USA). Pre-stained protein ladder was purchased from Fermentas (Ontario, Canada). Reagents for N-terminal protein sequencing were purchased from Sematec Pte Ltd (Tokyo, Japan). All other chemicals used unless otherwise indicated were of analytical grade and were obtained from Sigma-Aldrich (St. Louis, Mo., USA).

Size Exclusion Chromatography (SEC)

Crude *Bungarus fasciatus* venom (100 mg) (a generous gift from professor Cassian Bon, Pasteur Institute, Paris, France) was dissolved in 1 ml of distilled water and clarified by centrifugation at 13,200 rpm for 10 min. The clarified venom solution was applied to a HiLoad 16/60 Superdex 30 preparative grade size exclusion column (GE Healthcare, Life Sciences, Piscataway, N.J. USA) equilibrated with 50 mM Tris-HCl buffer (pH 8.0) and eluted with the same buffer using AKTA Prime Plus system (GE Healthcare Life Sciences, Piscataway, N.J., USA) at 0.5 ml/min flow rate. The elution of proteins from the column was monitored by absorbance at 280 nM.

Reverse Phase High Performance Liquid Chromatography (RP-HPLC)

The segregated fractions from SEC were individually resolved by HPLC using the Chromeleon Chromatography Data System on a Dionex Ultimate 3000 HPLC system (Thermo Fisher Scientific, Waltham, Mass. USA). The fractions were applied to a Jupiter C18 (250×4.6 mm) reversed-phase column (Phenomenex, Torrance, Calif., USA) and resolved using a multi-step gradient elution profile with buffer A being 0.1% TFA in water and buffer B being 0.1% TFA in 80% acetonitrile water solution.

Electrospray Ionization Mass Spectrometer (ESI-MS)

Sample (20 µl) was injected through the auto-sampler into a LCQ Fleet Ion Trap Mass Spectrometer (Thermo. Scientific, Waltham, Mass., USA) with a flow rate of 100 µl/min and the signals between 0.1-0.3 min after injection were captured using full scan mode and converted to actual mass by Xcalibur software.

Circular Dichroism Spectroscopy

Far-UV CD spectra (260-190 nm) of protein MilliQ water solution (0.1 mg/ml) was recorded using a Jasco J-810 Spectropolarimeter (Jasco Corp., Tokyo, Japan).

Pyridylethylation and Digestion

Pyridylethylation of cysteine residues of protein was carried out by dissolving protein (50-100 µg) into 1 ml of denaturing buffer (0.1 M Tris-HCl, pH 8.5, 6 M guanidine hydrochloride) followed by the addition of 5 µl of β-mercaptoethanol and 2 µl of 4-vinyl-pyridine. Oxygen was displaced from the mixture by blowing nitrogen gas over the solution before sealing the tube. The mixture was further incubated at 37° C. for 1 h. The pyridylethylated protein sample was purified by RP-HPLC, lyophilized and digested with Lys-C and Arg-C for 2-16 hours, after which the respected resulted peptides were separated and purified by RP-HPLC.

N-Terminal Sequencing

N-terminal sequencing of the pyridylethylated proteins was performed by automated Edman degradation using a PPSQ31 protein sequencer (Shimazu, Kyoto, Japan) equipped with an UV detector and a pump. The amino acids were identified by matching their retention times with that of a PTH-amino acid standard.

Recombinant Expression and Purification

The gene was synthesized by Geniwiz (South Plainfield, N.J., USA) according to the N-terminal sequencing results and cloned into pET28a expression vector using EcoRI and HindIII. pET28a containing the gene of interest was transformed into BL21 competent cells and expression of the proteins was induced by 1 mM IPTG at 18° C. for 20 h. The *E. coli* cells after induction were collected by centrifugation at 6,000 rpm for 30 min and resuspended in phosphate buffered saline (PBS) containing 8 M Urea. The resuspended solution was shook for 2 h at room temperature to lyse the cells and then subjected to centrifugation at 15,000 rpm for 30 min. The supernatants were filtered through 0.45 µm filter, mixed with Ni-NTA beads (Bio-Rad, Hercules, Calif., USA) and further shook for 2 h at room temperature. The Ni-NTA was collected and washed extensively in sequence with PBS containing 8 M Urea, PBS containing 160 mM NaCl and PBS. After which, the Ni-NTA beads were added into PBS containing 0.5 mg/ml bovine plasma thrombin and incubated in room temperature for 16 hours. The released proteins in the PBS were concentrated by HPLC and lyophilized. After dissolving into suitable buffer, the protein concentration was determined by measuring absorbance at 280 nM and using an extinction coefficient of 0.841 M-1·cm-1 as predicted by ExPASy ProtParam tool.

Effect on Activated Partial Thromboplastin Time (aPTT)

Equal volumes of human plasma, APTT-XL, 25 mM $CaCl_2$ and various concentration of protein diluted with HEPES buffer (25 mM, pH 7.4) were pre-warmed to 37° C. individually. Protein was added to plasma and incubated for 10 min, followed by the addition of APTT-XL and further incubation of 3 min. Clotting was initiated by the addition of 20 mM $CaCl_2$ to the mixture and the timing for clot formation was measured using an Infinite M200 microplate reader (Tecan, Mannedorf, Switzerland) or a BBL fibrometer BBL fibrometer (Becton Dickinson and Co., Maryland, USA). Human plasma was obtained from health donor's blood by centrifugation of the blood (containing one part 3.2% sodium citrate and 9 parts of blood) at 1500 rcf for 15 min.

Effect on Prothrombin Time

Equal volumes of human plasma, thromboplastin-D and various concentration of protein diluted with HEPES buffer (25 mM, pH 7.4) were pre-warmed to 37° C. individually. Protein was added to plasma and incubated for 10 min. Clotting was initiated by the addition of thromboplastin-D to the mixture and the timing for clot formation was measured using a BBL fibrometer (Becton Dickinson and Co., Maryland, USA). Human plasma was obtained from health donor's blood by centrifugation of the blood (containing one part 3.2% sodium citrate and 9 parts of blood) at 1500 rcf for 15 min.

Effect on Extrinsic Tenase Complex

Extrinsic tenase complex was reconstituted by adding 6.25 µl each of activation buffer (50 mM HEPES pH 7.4, 140 mM NaCl, 5 mM $CaCl_2$, 0.1% BSA), phosphatidylcholine:phosphatidylserine (PCPS) (7:3) (16 µM), tissue factor (80 nM) and FVIIa (160 pM) to a microtiter plate and incubating at 37° C. for 15 min. 12.5 µl of various concentrations of protein diluted with activation buffer were added and the mixture was incubated for another 15 min, followed by the addition of 12.5 µl of human FX (240 nM) and incubation for a further 15 min. The activation of FX to FXa by tenase complex was stopped by adding 25 µl of quench buffer (50 mM HEPES pH 7.4, 140 mM NaCl, 50 mM EDTA, 0.1% BSA), after which 25 µl of 2 mM S-2222 was added as a substrate for hydrolysis by FXa. The reaction velocity of S-2222 cleavage was monitored by measuring the absorbance at 405 nm using the Infinite M200 microplate reader. PCPS, tissue factor, FVIIa and FX were diluted with activation buffer from stock, while 52222 was diluted with distill water.

Effect on Intrinsic Tenase Complex

Intrinsic tenase complex was reconstituted by adding 6.25 µl each of activation buffer (50 mM HEPES pH 7.4, 140 mM NaCl, 5 mM $CaCl_2$, 0.1% BSA), PCPS (7:3) (16 µM), FVIIIa (80 units/ml) and FIXa (160 pM) to a microtiter plate and incubating at 37° C. for 10 min. 12.5 µl of various concentrations of protein diluted with activation buffer were added and the mixture was incubated for another 15 min, followed by the addition of 12.5 µl of human FX (240 nM) and incubation for a further 2 min. The activation of FX to FXa by tenase complex was stopped by adding 25 µl of quench buffer (50 mM HEPES pH 7.4, 140 mM NaCl, 50 mM EDTA, 0.1% BSA), after which 25 µl of 2 mM S-2222 was added as a substrate for hydrolysis by FXa. The reaction velocity of S-2222 cleavage was monitored by measuring the absorbance at 405 nm using the Infinite M200 microplate reader. PCPS, FIXa and FX were diluted with activation buffer from stock, while 52222 was diluted with distill water. FVIIIa was freshly activated from FVIII. FVIII was purchased from Bayer Pharmaceutics (Leverkusen, Germany) and reconstituted to a final concentration of 100 units/ml. 40 µl of 100 units/ml FVIII was mixed with 6 µl of activation buffer, 2 µl of 25 nM alpha-thrombin and incubated in 37° C. for 10 min. The reaction was stopped by adding 2 µl of 11,500 units/ml Hirudin and incubating in 37° C. for 5 min.

Selectivity Profile

The selectivity profiles of the anticoagulant proteins were examined against twelve serine proteases: procoagulant serine proteases (FVIIa, FIXa, FXa, FXIa, FXIIa, kallikrein, and thrombin), anticoagulant serine protease (activated protein C), fibrinolytic serine proteases (urokinase and plasmin), and classical serine proteases (trypsin and chymotrypsin).

50 µl of the respective serine protease diluted with activation buffer (50 mM HEPES pH 7.4, 140 mM NaCl, 5 mM $CaCl_2$, 0.1% BSA) from stock was pre-incubated with 25 µl of different concentrations of proteins in a microtiter plate for 30 min at 37° C., followed by the addition of 25 µl the appropriate chromogenic substrate. In a total volume of 100 µl, the final serine protease/chromogenic substrate concentrations were as follow: FVIIa (200 nM)/S-2288 (1 mM), FIXa (150 nM)/Spectrozyme FIXa (1 mM), FXa (2 nM)/S-2222 (0.5 mM), FXIa (0.5 nM)/S-2366 (0.5 mM), FXIIa (10 nM)/S-2302 (0.5 mM), kallikrein (16 nM)/S-2302 (0.5 mM), thrombin (2 nM)/S-2238 (0.1 mM), activated protein C (5 nM)/S-2366 (1 mM), urokinase (400 ng/ml)/S-2444 (0.5 mM), plasmin (5 nM)/S-2251 (0.5 mM), trypsin (10 nM)/S-2222 (1 mM), chymotrypsin (10 nM)/S-2586 (0.5 mM). The reaction velocity of substrate cleavage was monitored by measuring the absorbance at 405 nm using the Infinite M200 microplate reader.

Western Blotting

Concentration dependent assay: 5 µl of 750 pM FXIa, 5 µl of 300 nM FIX and 5 µl of various concentration of recombinant protein were pre-warmed to 37° C., mixed and further incubated in 37° C. for another 15 min. The reaction was terminated by adding 5 µl of 4×SDS sample buffer into each mixture and heating at 100° C. for 10 min. All the 20 µl was then loaded to a 10% SDS-PAGE, transferred to a nitrocellulose membrane (Bio Rad Laboratories, Hercules, Calif., USA) and probe for FIX and FIXa using mouse anit-FIX antibody (Hematologic Technologies, Essex Junction, Vt., USA).

Time dependent assay: 40 µl of 750 pM FXIa, 40 µl of 300 nM FIX and 40 µl of buffer or 30 µM recombinant proteins were pre-warmed to 37° C. and mixed. 15 µl aliquots were removed from the mixture at indicated times, mixed with 5 µl of 4×SDS sample buffer and heated in 37° C. for 10 min. All the 20 µl was then loaded to a 10% SDS-PAGE, transferred to a nitrocellulose membrane and probe for FIX and FIXa using mouse anit-FIX antibody.

Inhibition of FIX Cleavage

20 µl of indicated concentrations of recombinant protein or buffer was mixed with 15 µl of 667 pM FXIa and incubated in 37° C. for 1 hour. The cleavage of FIX was initialed by adding of 5 µl of 400 nM FIX into the above mixture. 2 min after adding FIX, 10 µl aliquots were removed from the mixture and quickly diluted by 125 times. 7.5 µl of the diluted solution was immediately mixed with 7.5 µl of freshly activated FVIIIa (80 units/ml), 7.5 µl of activation buffer (50 mM HEPES pH 7.4, 140 mM NaCl, 5 mM $CaCl_2$, 0.1% BSA), 7.5 µl of 16 µM PCPS and incubated in 37° C. for 10 min to form the intrinsic tenase complex. 25 µl of the above intrinsic tenase complex was mixed with 25 µl of 120 nM FX and further incubated for 2 min in room temperature, after which, 25 µl of quench buffer was added, followed by 25 µl of 2 mM S2222. The hydrolyze velocity of S2222 was monitored at 405 nM using a microplate reader. PCPS, FIXa, FXIa, recombinant protein and FX were diluted with activation buffer from stock, while S2222 was diluted with distill water.

Surface Plasmon Resonance

Protein (50 µl of 500 nM, in 10 mM acetate buffer, pH 6.0) was immobilized on a COOH5 chip (SensiQ technologies, Oklahoma, Okla., USA) using amine coupling with a SensiQ® Pioneer system (SensiQ technology, Oklahoma, Okla., USA). 145 µl of different concentrations of FXIa or chymotrypsin diluted in running buffer (10 mM Hepes, 150 mM NaCl, 5 mM $CaCl_2$ and 0.1% Tween 20, pH 7.4) were run though the chip surface at a flow rate of 20 µl/min and a dissociation time of 240 s was applied. The chip surface was regenerated with 25 µl of 10 mM glycine/HCl buffer pH 3.1 at a flow rate of 50 µl/min and a dissociation time of 240 s after each analysis cycle.

Progress Curve

Recombinant proteins, FXIa and substrate S2366 were pre-warmed to 37° C. 50 µl of indicated concentrations of recombinant protein were mixed with 40 µl of 1.25 nM FXIa. The reactions were started by adding of 10 µl of 10 mM S2366 and the hydrolysis of 52366 was monitored at 405 nM using a microplate reader.

Results:

BF01 was isolated as an anticoagulant selectively targeting intrinsic coagulation pathway.

Figure 1B:
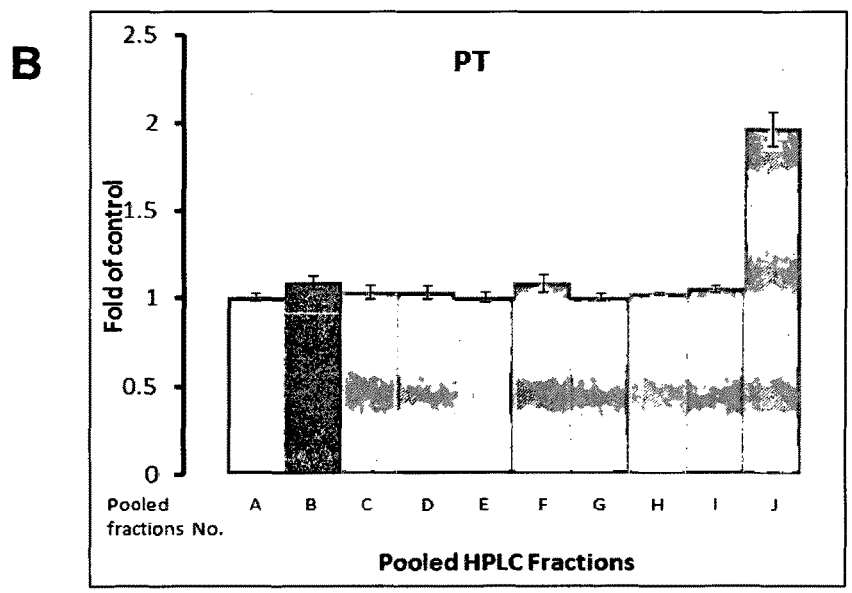

A plethora of different small-sized venom toxins have been derived from the venom of snakes from the *Bungarus* genus, and many of these toxins not only possess unique structure, more importantly, have potent agonistic or antagonistic effects on biological processes across various physiological systems. Examples of these toxins include three finger toxins, Kunitz type protease inhibitors, natriuretic peptides and C-type lectin. In order to isolate small size anticoagulant proteins that affect intrinsic coagulation pathway while leaving extrinsic coagulation pathway unaffected from the *Bungarus fasciatus* crude venom, crude *Bungarus fasciatus* venom was subjected to a two step fractionation using size exclusion chromatography (SEC) and reverse phase high performance liquid chromatography (RP-HPLC). The compositions' molecular weight (MW) of each RP-HPLC peak was checked by electrospray ionization mass spectrometer (ESI-MS) and peaks with major compositions' MW below 8 Kd were tested for their effect on activated partial thromboplastin time (aPTT) (FIG. 1A), a time that is used to detect effects on intrinsic and common pathways, and prothrombin time (PT) (FIG. 1B), a time that is used to detect effects in extrinsic and common pathways.

Figures 2A, 2B:
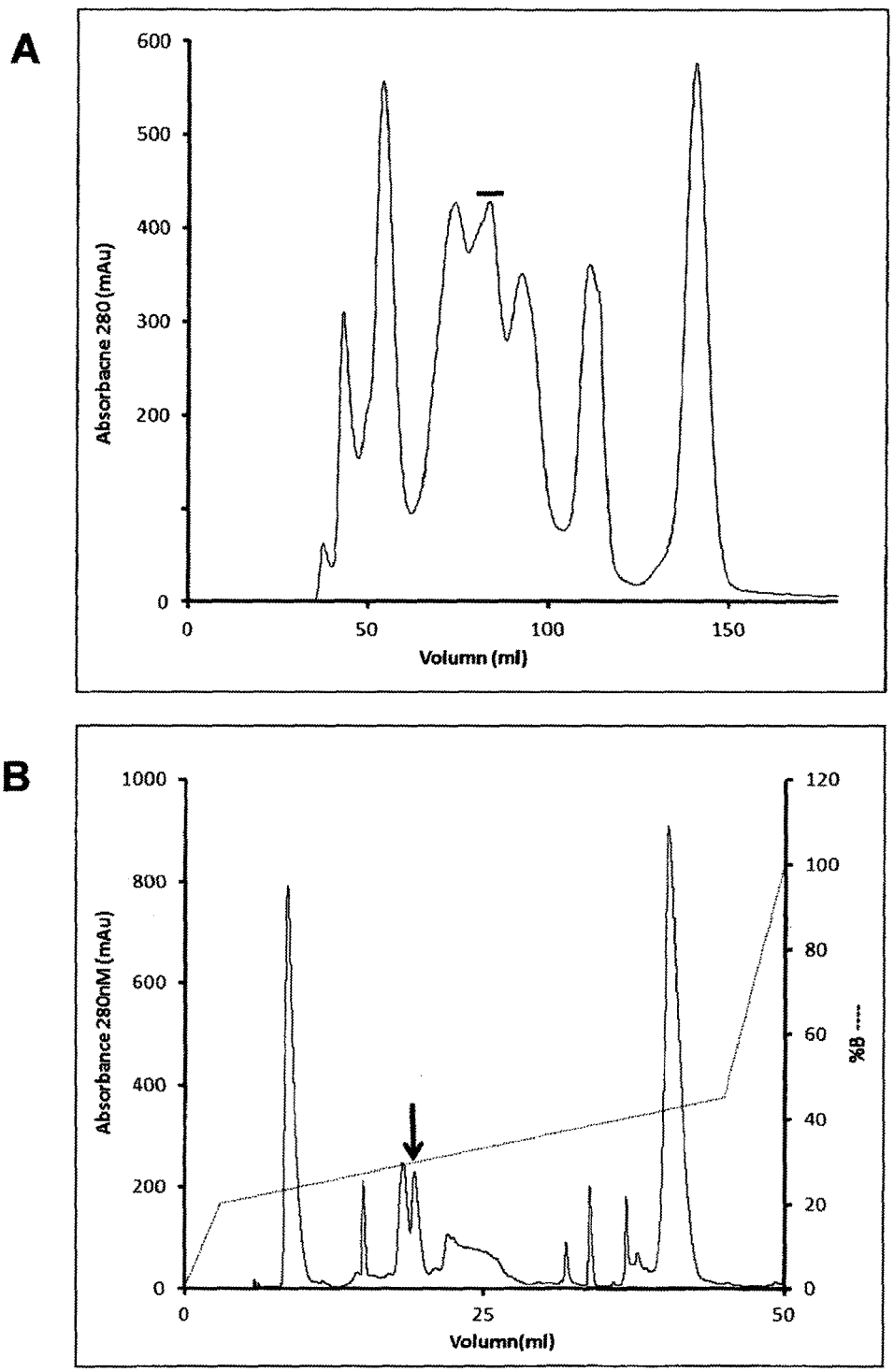

Two peaks labeled as E (major component MW 6977, named BF01) and H (major component MW 7307, named BF02) were shown to prolong aPTT significantly while having no effect on PT, which means peak E and F affect intrinsic coagulation only. These two peaks were chosen for further investigation and refractionated on RP-HPLC with a shallower gradient to get pure BF01 (SEC FIG. 2A, RP-HPLC FIG. 2B) and BF02 (purification profile not shown).

Figure 2C:
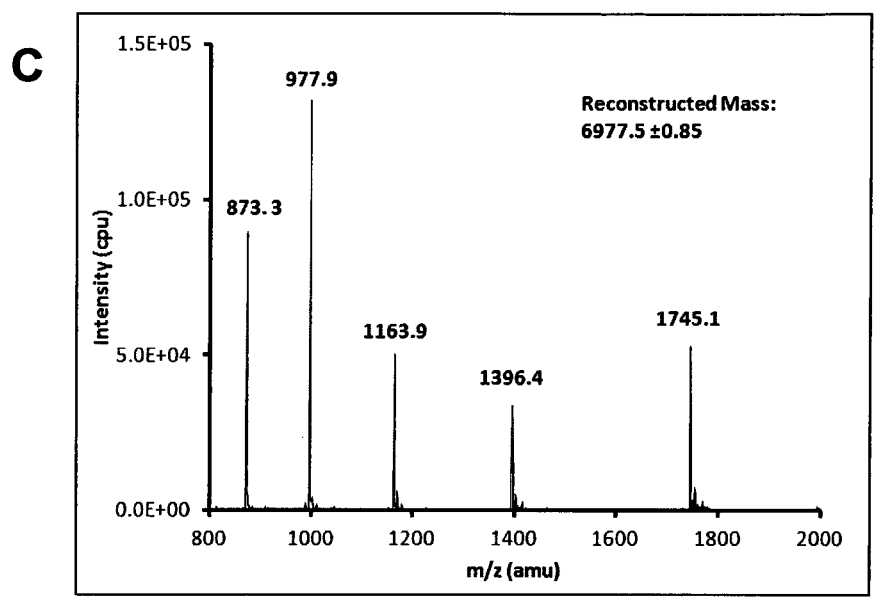
Figure 2D:
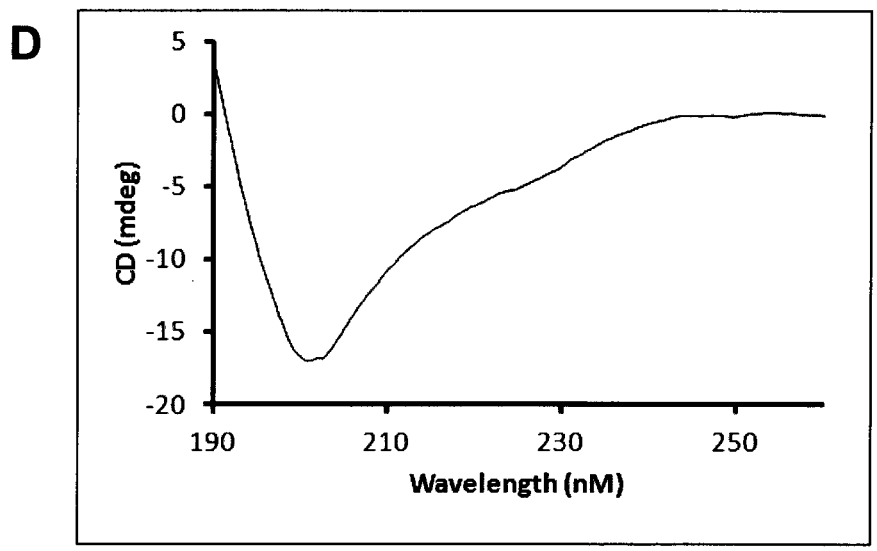

In order to determine the identity of these two proteins, they were subjected to pyridylethylation, Lys-C/Arg-C digestion and protein sequencing individually. ESI-MS profile of digestion resulted fragments and whole proteins (FIG. 2C and data not shown) together with N-terminal sequencing results suggested that the two proteins were isoforms sharing same amino acid sequence except that BF02 was three amino acids longer than BF01 in the C-terminal: Alignments of amino acid sequences of BF01 and BF02 with databases indicated that they were Kunitz type protease inhibitors and BF02 was only one residue different from one reported chymotrypsin inhibitor, Kunitz IX, isolated from venom of the same species (FIG. 2E) [Chen, C., et al., J Biol Chem, 2001. 276(48): p. 45079-87]. The secondary structures of BF01 (FIG. 2D) and BF02 (data not shown) were studied by circular dichroism spectroscopy which consistent with the profile of Kunitz type protease inhibitors. Since BF01 and BF02 exhibit similar activity and structure, only BF01 was further characterized.

rBF01 prolongs aPTT through inhibition of FXIa.

Figures 3A, 3B:
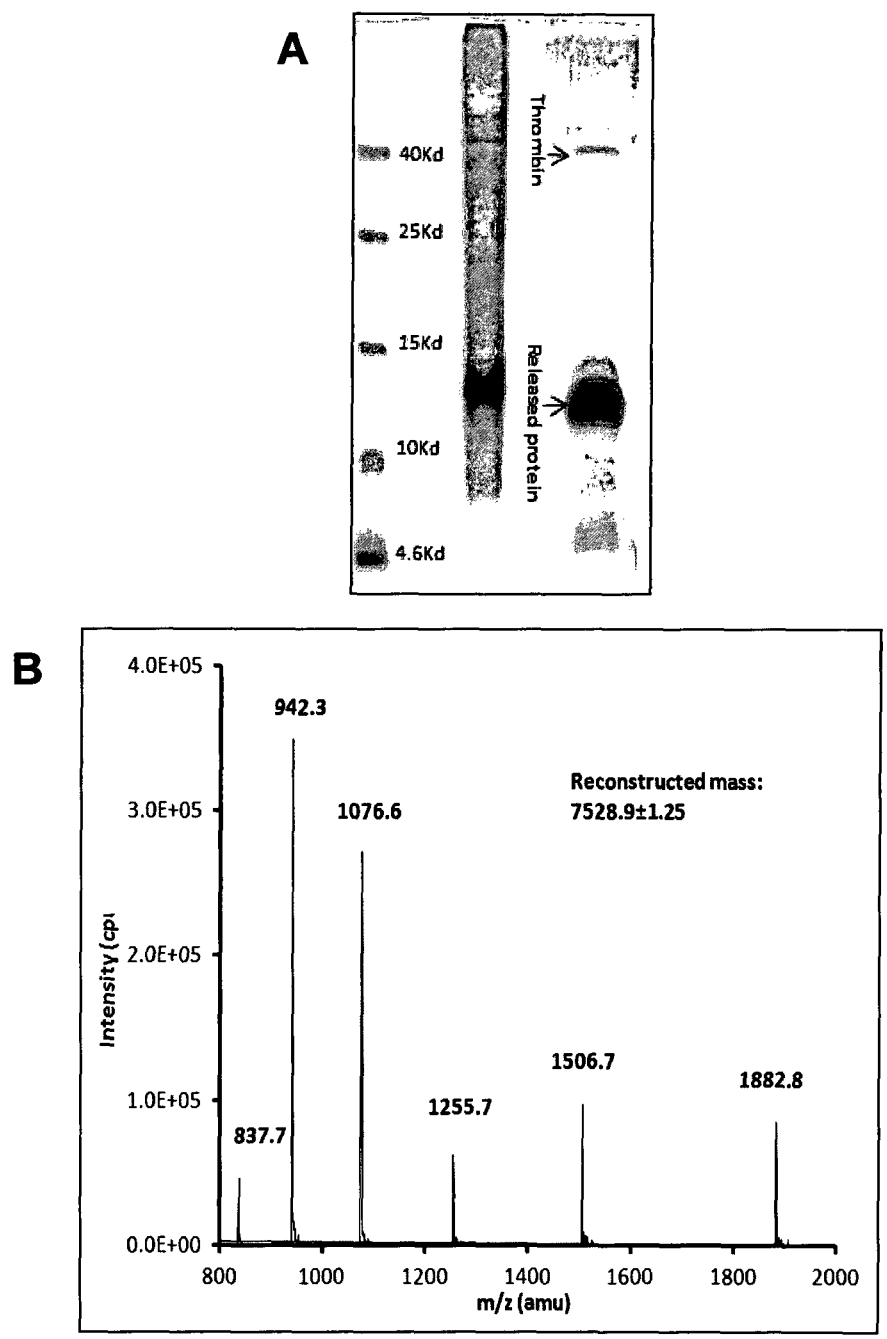
FIGS. 3A-3B: (3A) SDS PAGE. Left lane: Protein ladder; Middle lane: Bacteria suspension; Right lane: Released recombinant BF01 (rBF01) from Ni-NTA beads through thrombin cleavage. (3B) ESI-MS after concentrated by HPLC. rBF01 has a molecular weight of 7528.9±1.25 due to N-terminal modification.
Figures 4A, 4B:
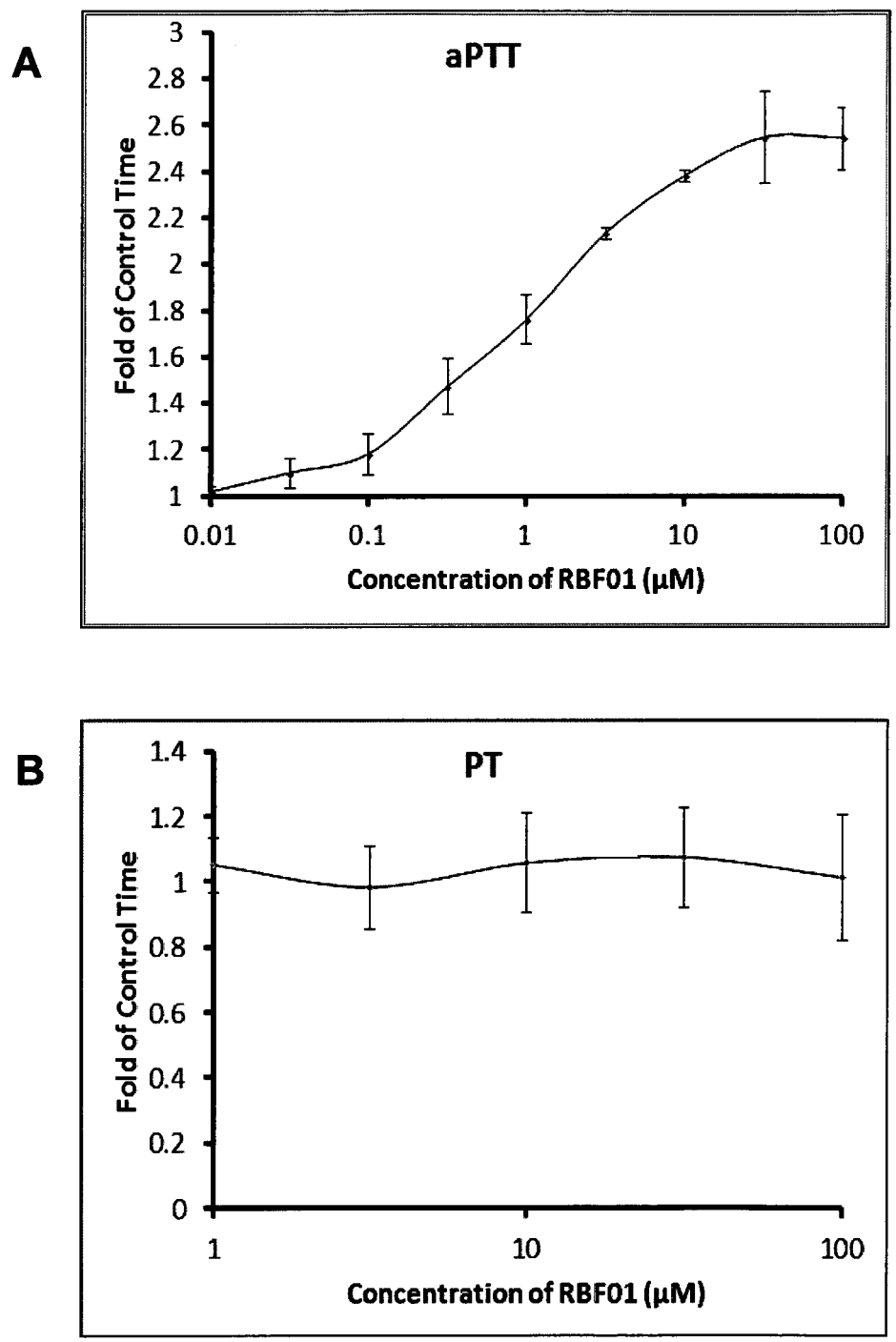
FIGS. 4A-4E: (4A) aPTT of human plasma pre-incubated with rBF01; (4B) PT of human plasma pre-incubated with rBF01; (4C) Activity of Intrinsic and Extrinsic Tenase Complex pre-incubated with rBF01; (4D) and (4E) Activity of serine protease pre-incubated with rBF01.

Since the venom supply is limited, BF01 was recombinantly expressed in *E. coli* and purified by cleavage on Ni-NTA beads (FIG. 3A). rBF01 has an additional 5 amino acids "GSEFM" in the N-terminal due to modification and thrombin cleavage during expression and purification. The identity and purity of rBF01 was ascertained by ESI-MS (FIG. 3B). In order to make sure the recombinant protein fold correctly and was active, the secondary structure, aPTT and PT of rBF01 were examined. Shown herein is that the recombinant rBF01 shares the same secondary structure as native protein and, consistent with the native protein, rBF01 prolonged aPTT in a dose-dependent manner (FIG. 4A) and doubled the clotting time at 2 µM, while not affecting PT (FIG. 4B) up to a concentration of 100 µM.

Figure 4C:
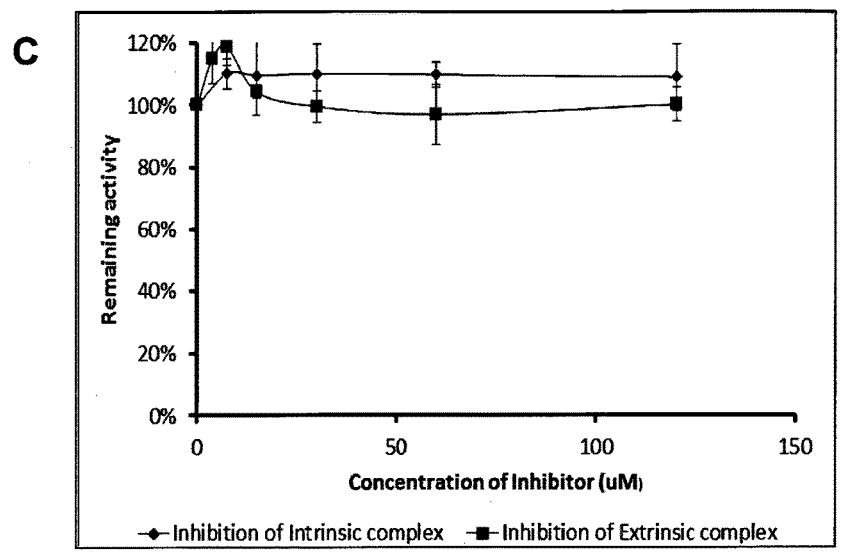
Figure 4D:
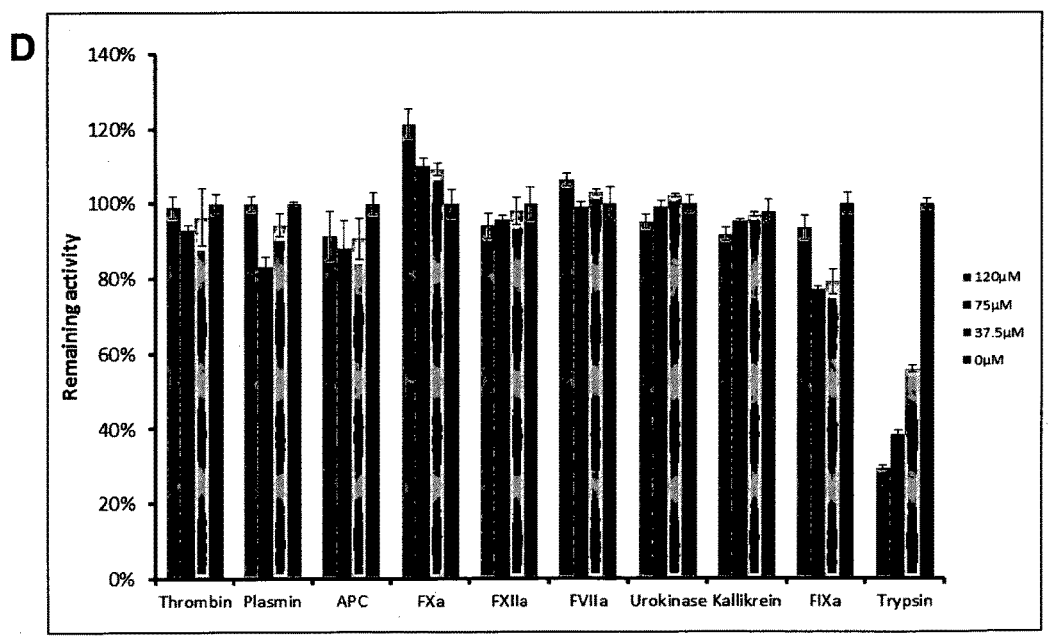
Figure 4E:
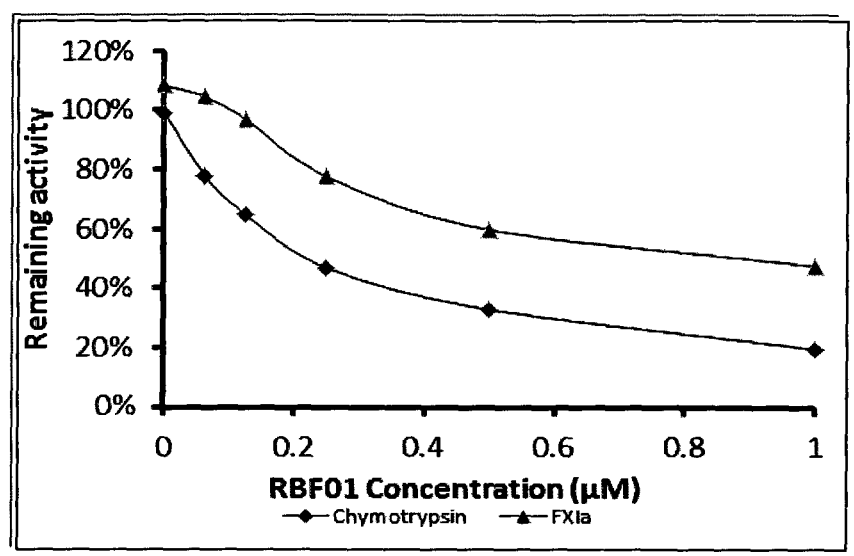

To determine the mechanism of how rBF01 prolongs aPTT, rBF01 was tested for its effect on extrinsic/intrinsic tenase complex (FIG. 4C), various serine proteases involved in the blood coagulation cascades as well as trypsin and chymotrypsin (FIGS. 4D and 4E) using chromogenic peptides as substrates. The results indicated that rBF01 inhibited chymotrypsin and FXIa strongly, and inhibited trypsin when present in high concentrations. Therefore, it was hypothesized that the mechanism through which rBF01 prolongs aPTT is the inhibition of FXIa. Prior to the data provided herein, an exogenous protein that selectively inhibiting FXIa has not been reported. Amino acid sequence alignments revealed that BF01 was only 45% identity to the kunitz domain of its physiological inhibitor protease nexin 2.

rBF01 interacts with and inhibits FXIa.

The interaction of rBF01 with FXIa was confirmed using surface plasmon resonance (SPR). rBF01 was immobilized on the surface of a COOH5 chip and different concentrations of FXIa in running buffers were analyzed. The interaction of rBF01 with FXIa was established (FIG. 5A), a calculated KD of around 20 nM was obtained by assuming a 1:1 stereochemistry ratio and one step binding. As rBF01 was shown to inhibit chymotrypsin, the interaction profile of rBF01 with chymotrypsin was also explored using the same chip (data not shown). The KD value of rBF01 with chymotrypsin is around 30 nM, in the same range of the previous report (50 nM) [17].

Figure 5C:
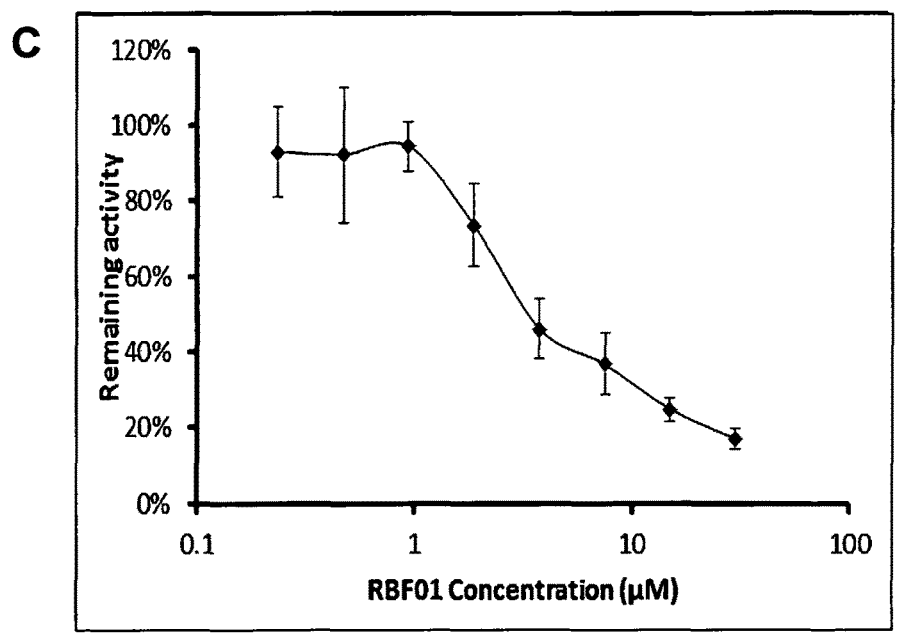

In order to confirm that rBF01 indeed inhibits the physiological function of FXIa, the inhibition effect of rBF01 on the cleavage of FXI, the physiological substrate of FXIa, by FXIa was tested. Cleavage of FIX by FXIa was monitored by two methods, western blotting (FIG. 5B) and chromogenic assays (FIG. 5C).

In western blotting, the cleavage process of FIX by FXIa was first monitored in the absence or presence of fixed concentration (10 µM) of rBF01. Presence of rBF01 was shown to slow down the cleavage of FIX (FIG. 5B upper). Since the FIXa band intensity reached saturation at 15 min in the absence of rBF01, we choose 15 min as a fixed time point to record the dose depend inhibition effect of rBF01 (FIG. 5B lower). Results indicated that rBF01 exerted a dose dependent inhibition of FIX cleavage. In chromogenic assay, the amount of cleavage product FIXa was quantified by the methods previously reported and the FIXa activity was plotted against the concentration of rBF01 (FIG. 5C), which indicated an IC50 of around 3 µM.

Figure 5D:
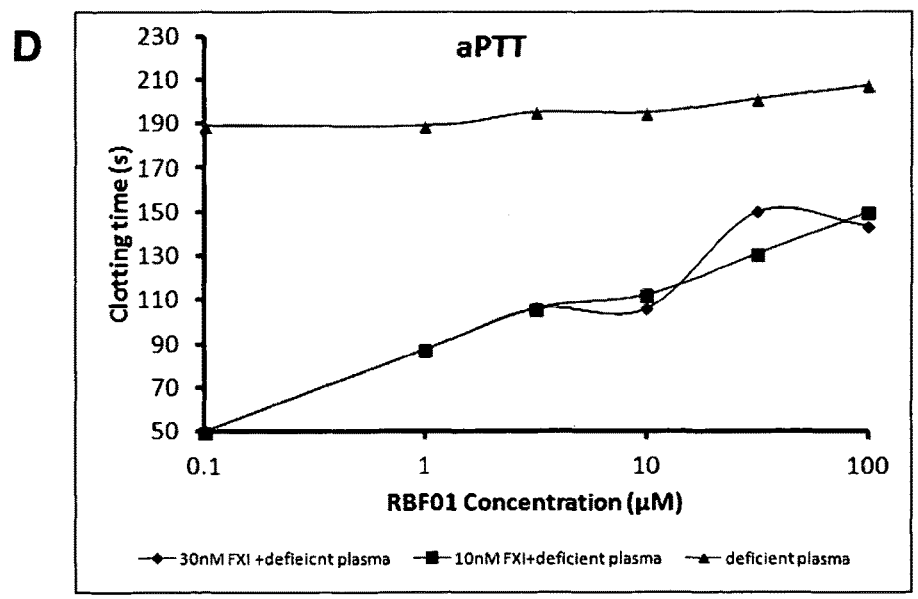

In order to draw correlation between FXIa inhibition and prolongation of aPTT, the function of rBF01 on aPTT was tested using FXI deficient human plasma and FXI deficient human plasma with FXI rescued by adding of exogenous FXI. rBF01 failed to prolong aPTT in FXI deficient plasma but was able to prolong aPTT in FXI rescued plasma with a similar potency as in normal human plasma (FIG. 5D). Thus, FXI is necessary for rBF01's function as an anticoagulant.

Figures 6A, 6B:
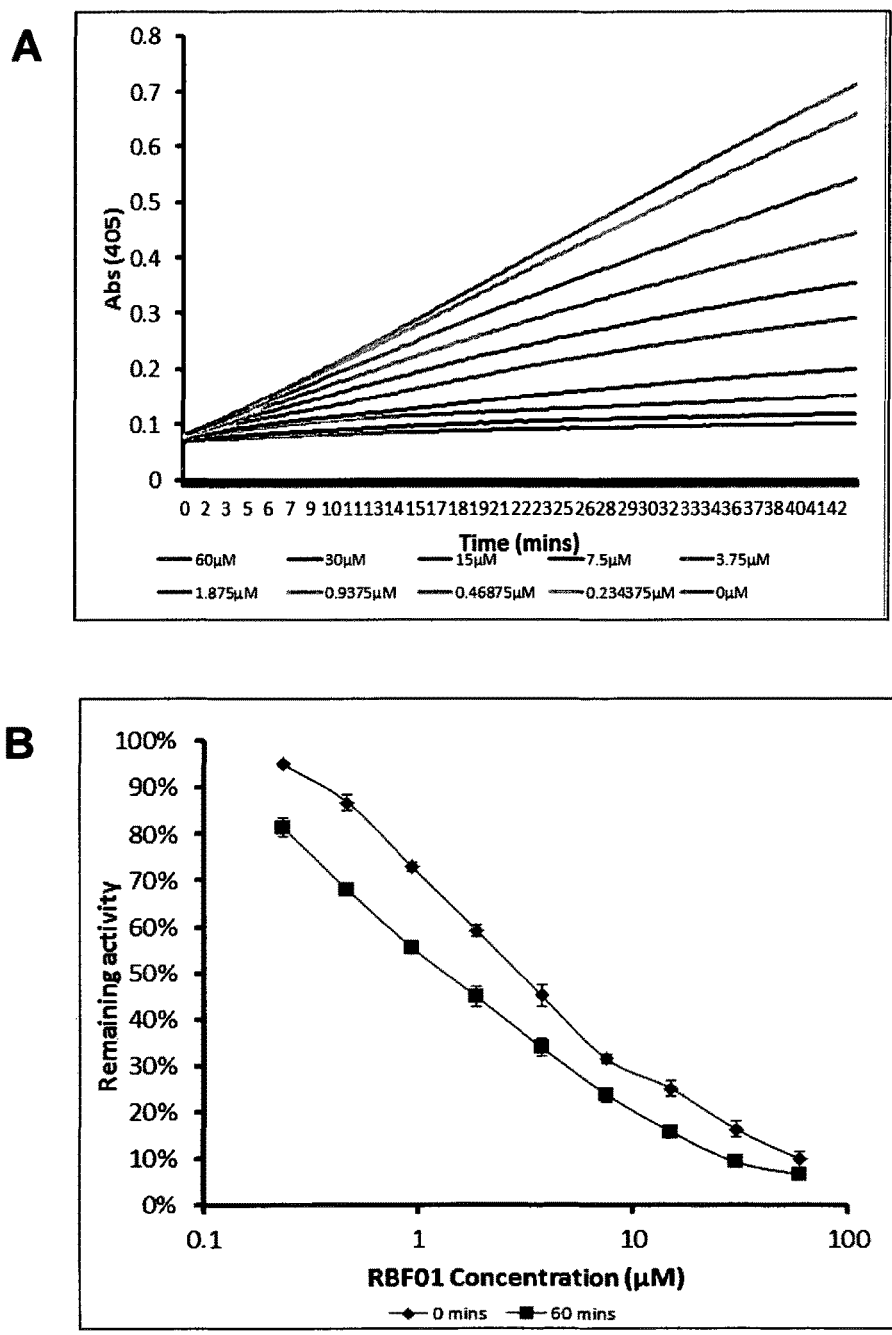
FIGS. 6A-6B: (6A) Progress curve of 52366 hydrolyze in presence of rBF01 (6B) Remaining activity of FXIa.
Figures 7A, 7B:
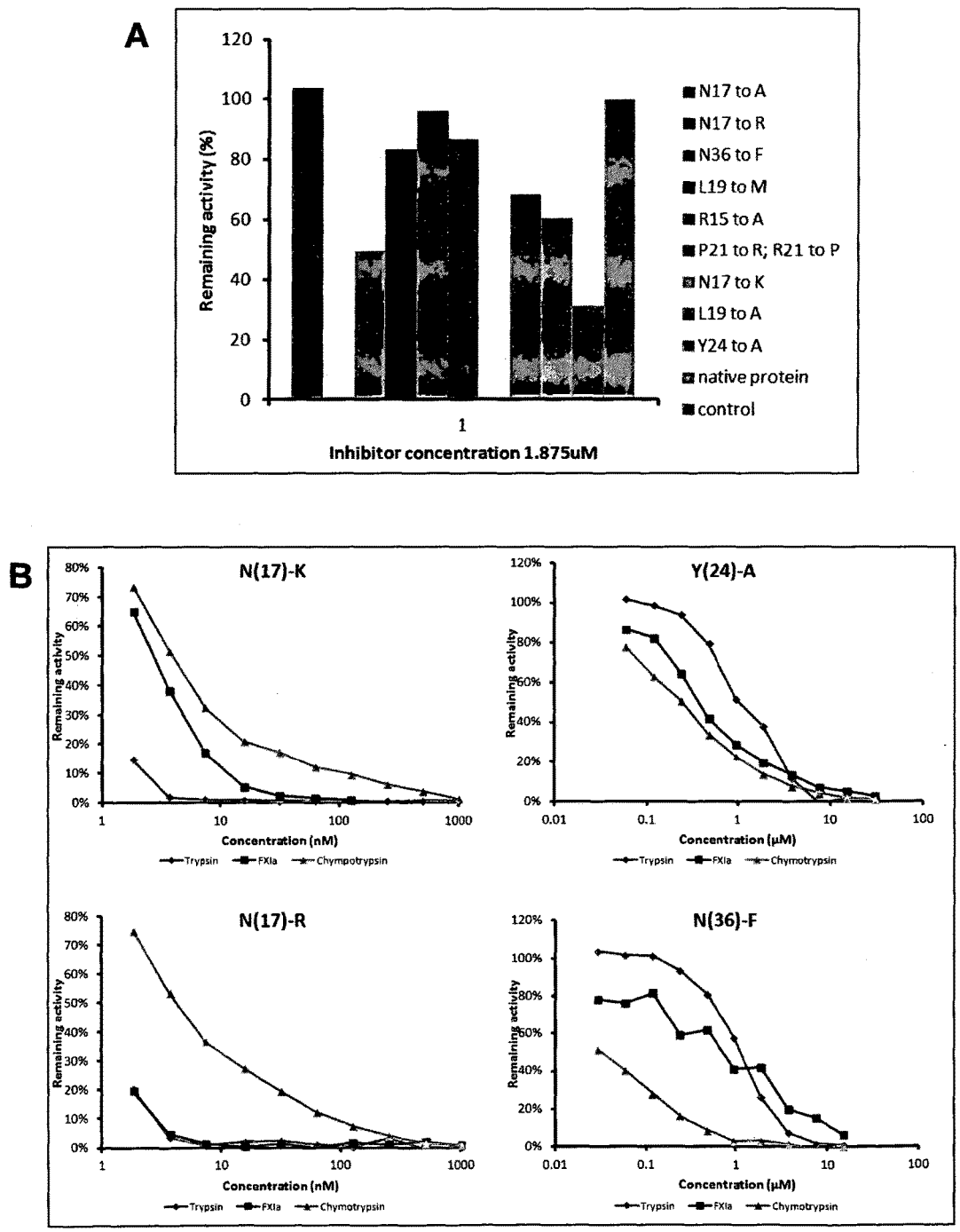
FIGS. 7A-7B: (7A) Inhibitory effect of various point mutants towards FXIa; (7B) Dose dependent inhibition curve of mutants.

As a number of kunitz type protease inhibitors exhibiting slow type inhibition, the inhibition kinetics of rBF01 was explored using chromogenic substrate S2366. The progress curve (FIG. 6A) and plotting of remaining activity of FXIa against rBF01 (FIG. 6B) indicated that rBF01 was a slow type inhibitor, with no pre-incubation IC50 3 µM and 1 hour pre-incubation IC50 1.5 µM. To test whether rBF01 was cleaved during interaction with the FXIa or chymotrypsin, a 10:1 molar ratio of rBF01 to enzyme mixture were incubated in 37° C. for overnight and injected into C18 column for detecting peptide fragments. Overnight incubation of rBF01 with FXIa did not result in cleavage of rBF01. In contrast, chymotrypsin cleaved the protein into several fragments with the cleavage site located in parts other than the loop regions.

Mutagenesis Study

In order to improve the potency and selectivity of the inhibitor, several residues located in the two loops and one chymotrypsin cleavage site of rBF01 were chosen for mutagenesis study. The mutations are P1 site substitutions N(17)-A; N(17)-K; N(17)-R; loop 2 residue substitution N(36)-F; L(19)-A; P2', substitutions L(19)-M; R(15)-A; chymotrypsin cleavage site substitution Y(24)-A; P(21)-R,R (15)-P. All the mutants were expressed and purified the same way as the recombinant rBF01 protein. The purity and identity of each mutant were ascertained by ESI-MS. Equal molar (1.875 μM) of the mutants were tested for inhibition of FXIa (FIG. 7A). It was observed that while the N(17)-A substitution completed abolished the inhibitory activity, N(17)-K and N(17)-R substitutions significantly improved the inhibitory activity. All other substitutions decreased the activity to some extent. The IC50 towards FXIa, chymotrypsin and trypsin for 4 mutants that are of particular interesting, namely the P1 site mutants N(17)-R; N(17)-K, the loop2 mutants N(36)-F, and the chymotrypsin cleavage site mutant Y(24)-A were further determined (FIG. 7B). N(36)-F and Y(24)-A failed to increase either potency or selectivity, N(17)-K and N(17)-R were able to increase FXIa inhibitory potency (~100 fold) and selectivity over chymotrypsin but both showed some decrease in terms of selectivity over trypsin. The mutants were also tested for prolongation of aPTT. Consistent with the enzyme activity assays, N(17)-K and N(17)-R showed much higher potency in prolongation of aPTT compared with native protein (data not shown).

Summary

The high risk of excessive bleeding associated with most anti-thrombotic drugs available in the market has made it necessary to discover new anticoagulants with minimal bleeding side effects. Inhibitors targeting the intrinsic coagulation pathway while leaving the extrinsic and common pathways unaffected are potential candidates of such new anticoagulants.

In an attempt to identify this new kind of anticoagulants, *Bungarus fasciatus* venom was fractionated and examined for effects on PT and aPTT of human plasma. Fractions that prolonged aPTT and left PT unaffected were further analyzed by mass spectrometry, protein sequencing, and circular dichroism spectroscopy and screened for specificity against different coagulation enzymes. Isolated candidate peptide was further characterized by a series of functional assays including inhibition kinetics, western blotting, surface plasmon resonance and blood coagulation assays.

A kunitz-type protease inhibitor (termed BF01) showing highly specific inhibition of FXIa was purified. The protein was recombinantly expressed in *Escherichia coli* system, and purified by Ni-NTA beads. rBF01 prolonged aPTT and was demonstrated to interact and inhibit FXIa in a dose- and time-dependent manner, while inhibition of other protease in the coagulation pathways (Kallikrein, FXIIa, FXIa, FXa, FIXa, FVIIa, Urokinase, alpha-Thrombin) were not observed. rBF01's inhibitory effect on the cleavage of FIX by FXIa was observed using western blotting through probing for FIX and FIXa. Mutagenesis analysis of BF01 was carried out as well, which produced mutants with much higher potency.

Therefore, BF01, variants thereof (e.g., rBF01) and mutants thereof (e.g., N(17); N(17)R), are highly specific anticoagulant proteins that targets FXIa of the intrinsic pathway, but leaving the extrinsic and common pathway of the coagulation cascade untouched. FXIa is a therapeutic target for anti-thrombosis and cardiovascular-protection. FXIa inhibition limits the amplification of thrombin formation by intrinsic cascade, while exerting a limited effect on the initiation of coagulation by tissue factor, thus minimizing the likelihood of bleeding side effects that are associated with drugs that target extrinsic and common pathways. Current studies indicate that FXIa inhibition will render existing clots more sensitive to fibrinolysis. Thus, BF01 represents a novel anticoagulant with minimal bleeding side effects that are associated with many of the currently approved anticoagulants.

Example 2

Some of the experiments in Example 2 are the same or similar to the experiments in Example 1.

Materials and Methods

Protein Purification and Identification

*B. fasciatus* venom proteins were purified by size exclusion, ion-exchange and high performance liquid chromatography. The homogeneity and mass of the proteins were ascertained by ESI-MS. Complete amino acid sequences of proteins were determined by Edman degradation of native proteins and peptides obtained by enzymatic digestion:

Study of Anticoagulant Properties and Serine Protease Specificity

The anticoagulant properties of proteins were characterized by aPTT and PT assays. The serine protease specificities of proteins were evaluated using amidolytic activity on specific chromogenic substrates.

Recombinant Expression and Point Mutagenesis

The synthetic Fasxiator gene was cloned into pET28a vector. Proteins were expressed using *E. coli* system, refolded and purified. Mutations were made through PCR using pET28a plasmid containing Fasxiator gene as a template and primers containing mismatch base pair(s).

Characterization of Interaction and Inhibition of FXIa

The interaction and inhibition of rFasxiator with FXIa was characterized using surface plasmon resonance, western blotting, chromogenic, PT and aPTT assays.

Kinetic Studies

The kinetic study was carried out according to the methods described by Copeland23 using KaleidaGraph 4.5 software20 and GraphPad Prism software.

$FeCl_3$ Induced Carotid Artery Thrombosis Model

All animal experiments and procedures were carried out under protocol 041/12 approved by Institutional Animal Care and Use Committee, National University of Singapore.

Statistical Analysis

Results are expressed as means±SD unless otherwise indicated. Statistical differences among the animal groups were analyzed by unpaired t-test. Significance was set at P≤0.05 (GraphPad Prism software, San Diego, Calif.).

Supplemental Materials and Methods

Materials

Thromboplastin-D and APTT-XL were purchased from Pacific Hemostasis, Thermo Scientific (Waltham, Mass., USA). Thrombin from bovine plasma was purchased from Merck Millipore (Darmstadt, Germany). FVIIa, FIXa, FXa, FXIa, activated protein C, plasmin, thrombin and FXI deficient plasma were purchased from Hematologic Technologies (Essex Junction, Vt., USA). FXIIa, kallikrein, trypsin and urokinase were purchased from Calbiochem, EMD Millipore (Billerica, Mass., USA). Phosphatidylcholine and phosphatidylserine were purchased from Sigma-Aldrich (St. Louis, Mo., USA). Chromogenic substrates, N-Benzoyl-L-isoleucyl-L-glutamyl-glycyl-L-arginine-p-nitroaniline hydrochloride and its methyl ester (S-2222), H-D-Phenylalanyl-L-pipecolyl-L-arginine-p-nitroaniline dihydrochloride (S-2238), H-D-Valyl-L-leucyl-L-lysine-p-nitroaniline dihydrochloride (S-2251), H-D-Isoleucyl-L-prolyl-L-arginine-p-nitroaniline dihydrochloride (S-2288), H-D-Prolyl-L-phenylalanyl-L-arginine-p-nitroaniline dihydrochloride (S-2302), L-Pyroglutamyl-L-prolyl-L-arginine-p-nitroaniline hydrochloride (S-2366), L-Pyroglutamyl-glycyl-L-arginine-p-nitroaniline hydrochloride (S-2444) were purchased from DiaPharma (Westchester, Ohio, USA). D-leucyl-phenylglycyl-arginine-p-nitroanilide diacetate (Spectrozyme FIXa) were purchased from Sekisui Diagnostics (Stanford, Conn., USA).

Dithiothreitol, 40% acrylamide and Coomassie Brilliant Blue R-250 were purchased from Bio-Rad Laboratories (Hercules, Calif., USA). Ammonia persulphate (APS) was purchased from AppliChem GmbH (Darmstadt, Germany). TEMED was purchased from MP Biomedicals (Solon, Ohio, USA). Tris-glycine SDS buffer was purchased from 1st Base (Singapore). Tris and Guanidine HCl were purchased from Alfa Aesar (Ward Hill, Mass., USA). Pre-stained protein ladder was purchased from Fermentas (Burlington, Ontario, Canada). Reagents for N-terminal protein sequencing were purchased from Sematec Pte Ltd (Tokyo, Japan). All other chemicals used, unless otherwise indicated, were of analytical grade and were obtained from Sigma-Aldrich (St. Louis, Mo., USA).

Methods

Size Exclusion Chromatography (SEC)

Crude *Bungarus fasciatus* venom (100 mg) (a generous gift from Professor Cassian Bon, Pasteur Institute, Paris, France) was dissolved in 1 ml of distilled water and clarified by centrifugation at 13,200 rpm for 10 min. The clarified venom solution was applied to a HiLoad 16/60 Superdex 30 preparative grade size exclusion column (GE Healthcare Life Sciences, Piscataway, N.J., USA) equilibrated with 50 mM Tris-HCl buffer (pH 8.0) and eluted with the same buffer using AKTA Prime Plus system (GE Healthcare Life Sciences, Piscataway, N.J., USA) at 0.5 ml/min flow rate. The elution of proteins from the column was monitored at 280 nm.

Cation Exchange Chromatography (CEC)

The pooled fractions from SEC were applied to a Bio-Rad S6 cation exchange chromatography column (Hercules, Calif., USA) and resolved by a gradient elution profile (flow rate of 2 ml/min) with buffer A being 50 mM Phosphate buffer pH 7.0 and buffer B being 50 mM Phosphate buffer pH 7.0 containing 0.5 M NaCl using the Chromeleon Chromatography Data System on a Dionex Ultimate 3000 HPLC system (Thermo Fisher Scientific, Waltham, Mass. USA).

Reverse Phase High Performance Liquid Chromatography (RP-HPLC)

Pooled fractions from SEC and cation exchange chromatography were applied to a Jupiter C18 (250×10 mm) reversed-phase column (Phenomenex, Torrance, Calif., USA) and resolved by a multi-step gradient elution profile (flow rate 5 ml/min) with buffer A being 0.1% TFA in water and buffer B being 0.1% TFA in 80% acetonitrile water solution using the Chromeleon Chromatography Data System on a Dionex Ultimate 3000 HPLC system (Thermo Fisher Scientific, Waltham, Mass. USA).

Electrospray Ionization Mass Spectrometer (ESI-MS)

Samples (20 µl) were injected through the auto-sampler into a LCQ Fleet Ion Trap Mass Spectrometer (Thermo Scientific, Waltham, Mass., USA) with a flow rate of 100 µl/min, the signals after injection were captured using full scan mode and masses of proteins and peptides were determined by Xcalibur software.

Effect on Activated Partial Thromboplastin Time (aPTT)

Human plasma was obtained from healthy donor's blood by centrifugation of the blood (containing one part 3.2% sodium citrate and 9 parts of blood) at 1500 rcf for 15 min. Equal volumes (50 µl) of human plasma, APTT-XL, 20 mM CaCl2 and various concentrations of protein diluted with HEPES buffer (25 mM, pH 7.4) were pre-warmed to 37° C. individually. Protein was added to plasma and incubated for 10 min, followed by the addition of APTT-XL and further incubation of 3 min. Clotting was initiated by the addition of 20 mM $CaCl_2$ to the mixture and the clot formation was measured using an Infinite M200 microplate reader (Tecan, Mannedorf, Switzerland) at 650 nm for fibrin polymers formation.

Prothrombin Time (PT)

Plasma, thromboplastin-D and various concentrations of protein diluted with HEPES buffer (25 mM, pH 7.4) were pre-warmed to 37° C. individually. Protein (100 µl) was added to plasma (100 µl) and incubated for 10 min. Clotting was initiated by the addition of thromboplastin-D (100 µl) to the mixture and the clot formation was measured using a BBL fibrometer (Becton Dickinson and Co., Maryland, USA).

Pyridylethylation and Digestion

Pyridylethylation of cysteine residues of protein was carried out by dissolving protein (50-100 µg) into 1 ml of denaturing buffer (0.1 M Tris-HCl, pH 8.5, 6 M guanidine hydrochloride) followed by the addition of 5 µl of β-mercaptoethanol and 2 µl of 4-vinyl-pyridine. Oxygen was displaced from the mixture by blowing nitrogen gas over the solution before sealing the tube. The mixture was further incubated at 37° C. for 1 h. The pyridylethylated protein sample was purified by RP-HPLC, lyophilized and digested with Lys-C and Arg-C for 2-16 h, after which the resulting peptides were separated by RP-HPLC N-Terminal Sequencing N-terminal sequencing of the pyridylethylated proteins was performed by automated Edman degradation using a PPSQ31 protein sequencer (Shimadzu, Kyoto, Japan) equipped with an UV detector and a pump. The PTH amino acids were identified by matching their retention times with those of standards. The sequences obtained were compared to other protein sequences in the database using Basic. Local Alignment Search Tool (BLAST).

Recombinant Expression, On-column Folding and Purification

The Fasxiator gene was synthesized by Geniwiz (South Plainfield, N.J., USA) according to the protein sequence and using *E. coli* preferred codons, and cloned into pET28a expression vector between EcoRI and HindIII (Thermo Scientific, Pittsburgh, Pa., USA) restriction sites. pET28a plasmid containing the gene of interest was transformed into BL21 competent cells (homemade) and expression of the proteins was induced by 1 mM IPTG at 18° C. for 20 h. The *E. coli* cells after induction were collected by centrifugation at 6,000 rpm for 30 min and resuspended in phosphate buffered saline (PBS) containing 8 M Urea. The resuspended solution was incubated for 2 h and sonicated for 5 min at 25° C. to lyse the cells and then subjected to centrifugation at 15,000 rpm for 30 min. The supernatants were filtered through 0.45 µm filters, before mixing with Ni-NTA beads (Bio-Rad, Hercules, Calif., USA) and further incubated for 2 h at room temperature. The Ni-NTA beads were collected and washed extensively in sequence with PBS containing 8 M Urea, PBS containing 160 mM NaCl and PBS. After which, the Ni-NTA beads were added into PBS containing 0.5 mg/ml thrombin (from bovine plasma) and incubated in room temperature for 16 h to enzymatic release the folded protein. The released proteins in the PBS were concentrated by HPLC and lyophilized. After dissolving into H2O, the protein concentration was determined by measuring absorbance at 280 nm and using an extinction coefficient predicted by ExPASy ProtParam tool.

Circular Dichroism Spectroscopy

Far-UV circular dichroism spectra (260-190 nm) of protein MilliQ water solution (0.08-0.1 mg/ml) was recorded using a Jasco J-810 Spectropolarimeter (Jasco Corp., Tokyo, Japan).

Effect on Intrinsic/Extrinsic Tenase Complex

The intrinsic and extrinsic tenase complex was reconstituted according the methods reported by Koyama et al., *General Pharm.* 31:277-282 (1998) with minor modification.

Activation of FVII: The FVIIIa used for reconstitution of intrinsic tenase complex was freshly activated from FVIII, purchased from Bayer Pharmaceutics (Leverkusen, Germany). FVIII was reconstituted to a final concentration of 100 units/ml. 100 units/ml FVIII (40 µl) was mixed with 6 µl of activation buffer, 2 µl of 25 nM α-thrombin and incubated at 37° C. for 10 min. The reaction was stopped by adding 2 µl of 11,500 units/ml Hirudin and incubating at 37° C. for 5 min.

Reconstitution of intrinsic tenase: Intrinsic tenase complex was reconstituted by adding 6.25 µl each of activation buffer (50 mM HEPES pH 7.4, 140 mM NaCl, 5 mM CaCl$_2$, 0.1% BSA), phosphatidylcholine: phosphatidylserine (PCPS) (7:3) (16 µM), FVIIIa (80 units/ml) and FIXa (160 pM) to a microtiter plate and incubating at 37° C. for 10 min. 12.5 µl of various concentrations of Inhibitors diluted with activation buffer were added and the mixture was incubated for another 15 min, followed by the addition of 12.5 µl of human FX (240 nM) and incubation for a further 2 min. The activation of FX to FXa by tenase complex was stopped by adding 25 µl of quenching buffer (50 mM HEPES pH 7.4, 140 mM NaCl, 50 mM EDTA, 0.1% BSA), after which 25 µl of 2 mM S-2222 substrate was added. The cleavage of S-2222 by FXa was measured at 405 nm using the Infinite M200 microplate reader. PCPS, FIXa and FX were diluted with activation buffer from stock, while S2222 was diluted with distilled water.

Reconstitution of extrinsic tenase: Extrinsic tenase complex was reconstituted by adding 6.25 µl each of activation buffer (50 mM HEPES pH 7.4, 140 mM NaCl, 5 mM CaCl$_2$, 0.1% BSA), PCPS (7:3) (16 µM), tissue factor (80 nM) and FVIIa (160 pM) to a microtiter plate and incubating at 37° C. for 15 min. Various concentrations of inhibitors in the activation buffer (12.5 µl) were added and the mixture was incubated for another 15 min, followed by the addition of 12.5 al of human FX (240 nM) and incubation for a further 15 min. The activation of FX to FXa by tenase complex was stopped by adding 25 µl of quench buffer (50 mM HEPES pH 7.4, 140 mM NaCl, 50 mM EDTA, 0.1% BSA), after which 25 µl of 2 mM S-2222 was added as a substrate for hydrolysis by FXa. The cleavage of S-2222 was measured at 405 nm using the Infinite M200 microplate reader.

Protease Selectivity Profile

The selectivity profiles of the anticoagulant proteins were examined against twelve serine proteases: procoagulant serine proteases (FVIIa, FIXa, FXa, FXIa, FXIIa, kallikrein, and thrombin), anticoagulant serine protease (activated protein C), fibrinolytic serine proteases (urokinase and plasmin), and classical serine proteases (trypsin and chymotrypsin).

50 µl of the respective serine protease diluted with activation buffer (50 mM HEPES pH 7.4, 140 mM NaCl, 5 mM CaCl$_2$, 0.1% BSA) from stock was pre-incubated with 25 µl of different concentrations of proteins in a microtiter plate for 30 min at 37° C., followed by the addition of 25 µl the appropriate chromogenic substrate. In a total volume of 100 for rFasxiator the final serine protease/chromogenic substrate concentrations were as follows: FVIIa (200 nM)/S-2288 (1 mM), FIXa (150 nM)/Spectrozyme FIXa (1 mM), FXa (2 nM)/S-2222 (0.5 mM), FXIa (0.5 nM)/S-2366 (0.5 mM), FXIIa (10 nM)/S-2302 (0.5 mM), kallikrein (16 nM)/S-2302 (0.5 mM), thrombin (2 nM)/S-2238 (0.1 mM), activated protein C (5 nM)/S-2366 (1 mM), urokinase (400 ng/ml)/S-2444 (0.5 mM), plasmin (5 nM)/S-2251 (0.5 mM), chymotrypsin (10 nM)/S-2586 (0.5 mM). The cleavage of substrate was measured at 405 nm using the Infinite M200 microplate reader.

As the concentrations of rFasxiator variants (1 nM to 10 µM) used were much lower than rFasxiator (30 µM~120 µM), the concentration of the serine proteases were concomitantly decreased (FVIIa 100 nM, FXa 1 nM, FXIIa 5 nM, Kallikrein 2 nM, thrombin 1 nM, activated protein C 2 nM, plasmin 1 nM, chymotrypsin 5 nM) to increase the ratio of inhibitor to enzyme. The substrate concentrations of FXa (S2222 1 mM), FXIa (S2366 1 mM) and activated protein C (S2366 1.5 mM) were increased to allow for a longer monitor time.

Surface Plasmon Resonance rFasxiator (50 µl of 500 nM, in 10 mM acetate buffer, pH 6.0) was immobilized on a COOH5 chip (SensiQ technologies, Oklahoma; Oklahoma, USA) using amine coupling with a SensiQ Pioneer system (SensiQ technology, Oklahoma, Okla., USA). 145 µl of different concentrations of FXIa or chymotrypsin diluted in running buffer (10 mM HEPEs, 150 mM NaCl, 5 mM CaCl$_2$ and 0.1% Tween 20, pH 7.4) were used as analytes at a flow rate of 20 µl/min and a dissociation time of 240 s was applied. The chip surface was regenerated with 25 µl of 10 mM glycine/HCl buffer pH 3.1 at a flow rate of 50 µl/min and a dissociation time of 240 s after each analysis cycle.

Western Blotting

Concentration-dependent inhibition of FIX activation: 5 µl of 750 pM FXIa, 5 µl of 300 nM FIX and 5 µl of various concentration of recombinant inhibitor pre-warmed to 37° C. were mixed and further incubated at 37° C. for 15 min before mixing with 5 µl of 4×SDS sample buffer and heated at 37° C. for 10 min to stop the reaction.

Time-dependent inhibition of FIX activation: 40 µl of 750 pM FXIa, 40 µl of 300 nM FIX and 40 µl of buffer or 30 µM recombinant proteins pre-warmed to 37° C. were mixed. From this mixture 15 µl aliquots were removed at indicated times, mixed with 5 µl of 4×SDS sample buffer and heated at 37° C. for 10 min to stop the reaction.

All the 20 µl was then loaded to a 10% SDS-PAGE, transferred to a nitrocellulose membrane (Bio-Rad Laboratories, Hercules, Calif., USA) and probed for FIX and FIXa using mouse anti-FIX antibody (Hematologic Technologies, Essex Junction, Vt., USA).

Inhibition of FIX Cleavage

20 µl of indicated concentrations of recombinant protein or buffer was mixed with 15 µl of 667 pM FXIa and incubated at 37° C. for 1 h. The cleavage of FIX was initiated by adding of 5 µl of 400 nM FIX into the above mixture. 2 min after adding FIX, 10 µl aliquots were removed from the mixture and quickly diluted by 125 times. 7.5 µl of the diluted solution was immediately mixed with 7.5 µl of freshly activated FVIIIa (80 units/nil), 7.5 µl of activation buffer (50 mM HEPES pH 7.4, 140 mM NaCl, 5 mM CaCl2, 0.1% BSA), 7.5 µl of 16 µM PCPS and incubated at 37° C. for 10 min to form the intrinsic tenase complex. 25 µl of the above intrinsic tenase complex was mixed with 25 µl of 120 nM FX and further incubated for 2 min in room temperature, after which, 25 µl of quench buffer was added, followed by 25 µl of 2 mM S2222. The cleavage of S2222 was measured at 405 nm using a microplate reader. PCPS, FIXa, FXIa, recombinant protein and FX were diluted with activation buffer from stock, while S2222 was diluted with distilled water.

Generation of Progress Curve of 52366 Cleavage by FXIa

Recombinant proteins, FXIa and substrate S2366 were pre-warmed to 37° C. 25 µl of indicated concentrations of recombinant protein were mixed with 25 µl of 4 mM S2366. The reactions were started by adding of 50 µl of 1 nM FXIa and the hydrolysis of S2366 was measured at 405 nm using a microplate reader.

Generation of Point Mutants

Mutations were made through polymerase chain reactions using pET28a plasmid containing the original Fasxiator gene as a template and primers containing designed mismatch base pair(s). The components of the reactions are Pfu Turbo® DNA polymerase 0.4 µl (1 U) (Stratagene, La Jolla, Calif., USA), dNTPs 2 µl (2 mM of each) (Thermo Scientific, Pittsburgh, Pa., USA), primers forward and reverse 1 µl (0.75 µM each), pET28a plasmid 0.14 µl (20 ng), 10×Pfu Turbo® buffer 2 µl, ddH2O 13.46 µl. The annealing temperatures used were 54° C. and 60° C., a total of 16 cycles of replication were carried out using a thermocycler (Biorad, Hercules, Calif., USA). The reaction mixtures were treated with DpnI 0.1 µl (1 U) (Thermo Scientific, Pittsburgh, Pa., USA) and analyzed by 1% agarose gel for complete digestion before transformation into DH5a competent cells (homemade). Obtained clones were sequenced (service provided by 1st base, Singapore) and plasmids containing desired mutations were transformed into BL21 competent cells for protein expression. The induction and purification procedures were the same as described above. The molecular weights of purified mutated proteins were determined using ESI-MS as previously described to confirm the identity of the proteins. The proteins were quantified by measuring absorbance at 280 nm and using the extinction coefficient predicted by ExPASy ProtParam tool.

Kinetic Studies

The kinetic study was carried out according to the methods described by Copeland R A, Binding Inhibitors & Time-Dependent Inhibition, *Enzymes: a practical introduction to structure, mechanism and data analysis*, 2nd ed. New York::Wiley-VCH 2000:305-349.

Ki determination for slow type inhibitor: Progress curves of slow type inhibitors were generated as described above. The progress curves were fitted into Equation 1 using KaleidaGraph 4.5 software.

$$P=V_s \times t+(V_i-V_s)[1-\exp(-K_{obs}\times t)]/K_{obs}+P_0 \qquad \text{Eqn (1)}$$

P stands for amount of product; $V_s$: steady state velocity; $V_i$: initial state velocity; t: time; $P_0$: correction factor for initial amount of product; $K_{obs}$: apparent first-order rate constant for the inter-conversion between $V_s$ and $V_i$.

Obtained $K_{obs}$ were plotted against substrate concentration and inhibitor concentration respectively.

In fixed inhibitor concentrations, for competitive inhibitors, $K_{obs}$ decreases as substrate concentration is raise; for noncompetitive inhibitors, $K_{obs}$ does not vary with substrate concentration, while for uncompetitive inhibitors, $K_{obs}$ increase with increasing substrate concentration.

With fixed substrate concentration, for type I inhibitor, plot of $K_{obs}$ versus inhibitor concentration yields a straight line, while for type II inhibitor, plot of Kobs versus inhibitor concentration results in a hyperbola.

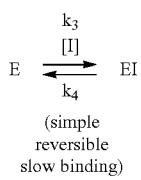

(simple reversible slow binding)

Type 1

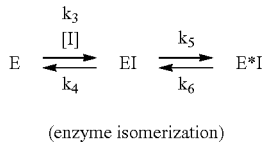

(enzyme isomerization)

Type 2

For Type I inhibitor, the relationship between $K_{obs}$ and inhibitor concentration [I] is given by Equation 2

$$K_{obs}=K_4(1+[I]/Ki^{app}) \qquad \text{Eqn (2)}$$

For competitive inhibitor, the relationship between $Ki^{app}$ and $K_i$ were given by Equation 3

$$K_i=Ki^{app}/(1+[S]/Km) \qquad \text{Eqn (3)}$$

[S] stands for substrate concentration, Km stands for the Michaelis constant.

$K_i$ determination for fast type inhibitor: For fast type inhibitors, their $K_i$ were calculated by Equation 4

$$K_i=IC_{50}/(1+[S]/Km) \qquad \text{Eqn (4)}$$

IC50 were determined by fitting the respective dose-inhibition curve using GraphPad Prism software.

FeCl3 Induced Carotid Artery Thrombosis Model

All animal experiments and procedures were carried out under protocol 041/12 approved by Institutional Animal Care and Use Committee (IACUC), National University of Singapore. The FeCl3 induced carotid artery thrombosis model was performed as described previously. C57BL/6 male mice (9-11 weeks old, 24.5-27.5 g) (Invivos, Singapore) were anesthetized with an i.p. injection of ketamine (75 mg/Kg) and medetomidine (1 mg/Kg). Two sets of independent experiments were performed to evaluate the efficacy of rFasxiator. In the first experiment, 0.1 ml protein (2 mg/ml) was injected into the mice via tail vein. The right carotid artery was exposed using blunt dissection and vascular injuries were caused by applying a filter paper of sizes of 2 mm×2 mm saturated with 6% FeCl3 on top of the carotid artery for 3 min. In the second experiment higher concentration of protein (0.15 ml) was injected and intensity of injury was decreased by smaller filter papers (1 mm×1 mm) and lower FeCl$_3$ (5%). After 3 min FeCl$_3$ exposure, the filter paper was removed and the vessel was washed with sterile normal saline. To determine the time to occlusion, a miniature Doppler flow probe (Cat # MA0.5 VB, Transonic Systems Inc., Ithaca, N.Y., USA) was placed around the carotid artery and blood flow was recorded using a Transonic flowmeter (Transonic Systems Inc., Ithaca, N.Y., USA). The maximal monitor time after injury is 30 min. Mice were killed by cervical dislocation immediately after conclusion of the experiment and prior to recovery from anesthesia.

Statistical Analysis

Results are expressed as means±SD unless otherwise described. Statistical differences among the animal groups were analyzed by unpaired t-test. Significance was set at P≤0.05 (GraphPad Prism software, San Diego, Calif.).

Results

Isolation of Anticoagulants that Selectively Target Intrinsic Pathway

Figures 9A, 9B, 9C, 9D, 9E, 9F:
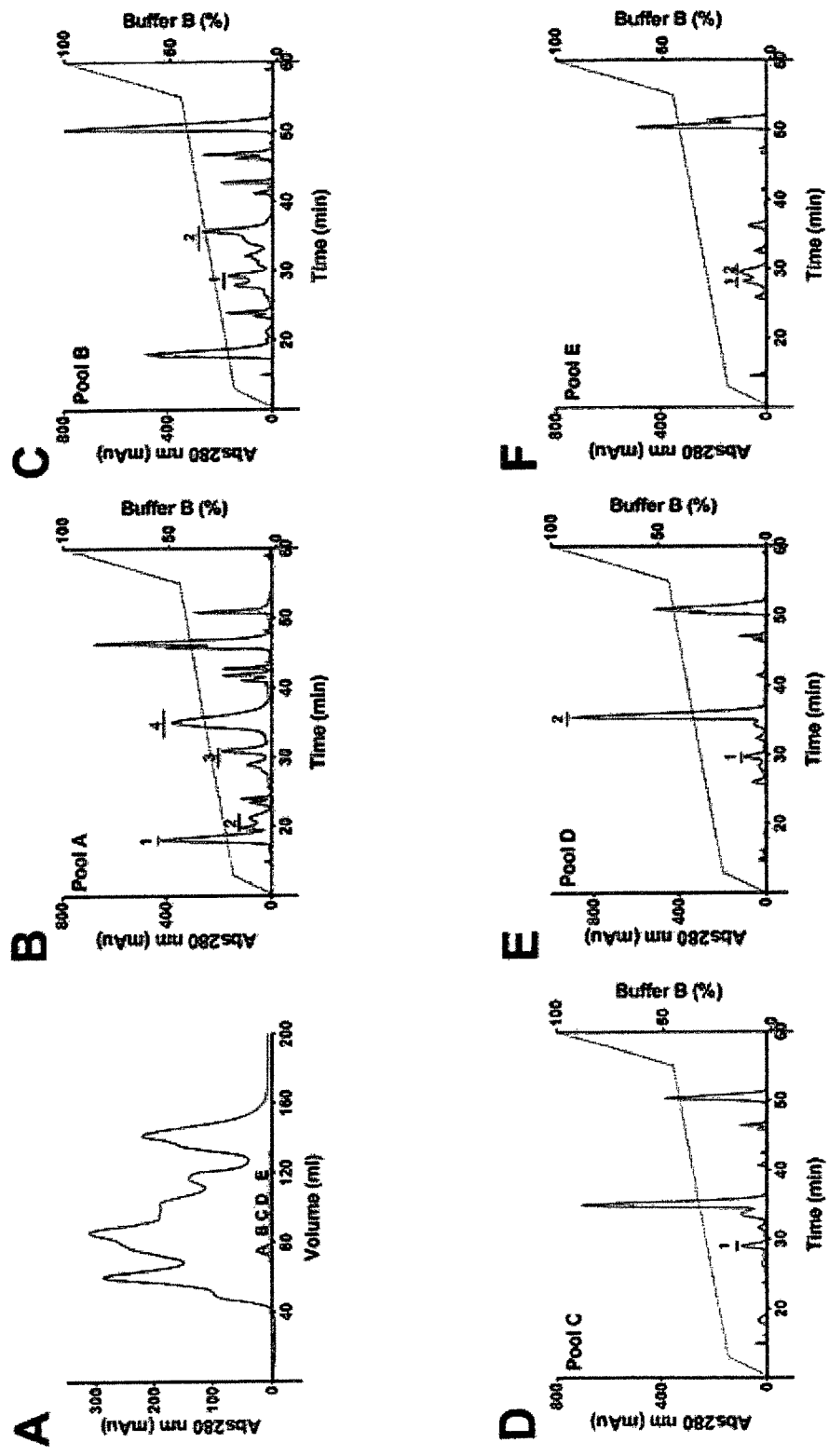

A plethora of different low molecular weight venom toxins, including three-finger toxins, Kunitz-type protease inhibitors, natriuretic peptides and C-type lectins, have been isolated from the venom of *Bungarus* snake venoms. To isolate low molecular weight anticoagulant proteins we subjected *Bungarus fasciatus* venom to a two-step fractionation using size exclusion chromatography (SEC) and reversed phase high performance liquid chromatography (RP-HPLC) (FIG. 9A-9F). The molecular weights (MW) of each RP-HPLC fractions were then determined by electrospray ionization mass spectrometry (ESI-MS). Pooled fractions containing proteins below 8 kDa (Table 2) were tested for their effects on aPTT and PT (FIG. 9G).

Three RP-HPLC pools (B1, C1 and D1) prolonged aPTT without significant effects on PT (FIG. 9G), indicating that they affected the intrinsic pathway, while leaving the extrinsic pathway unaffected. ESI-MS results indicated that these pools mainly contained two proteins with MW of 6977.5±0.85 Da and 7307.3±0.67 Da. These two proteins were separated by introducing a cation exchange chromatography (CEC) step between SEC and RP-HPLC (FIG. 9H-9J). The homogeneity and mass of the purified proteins were determined by ESI-MS. The smaller protein (MW: 6977.5±0.85 Da) was named BF01, and the larger molecule (MW: 7307.3±0.67 Da) was named BF02. Both BF01 and BF02 prolonged aPTT (FIG. 9K).

Protease Specificity of Novel Anticoagulants

Figure 16:
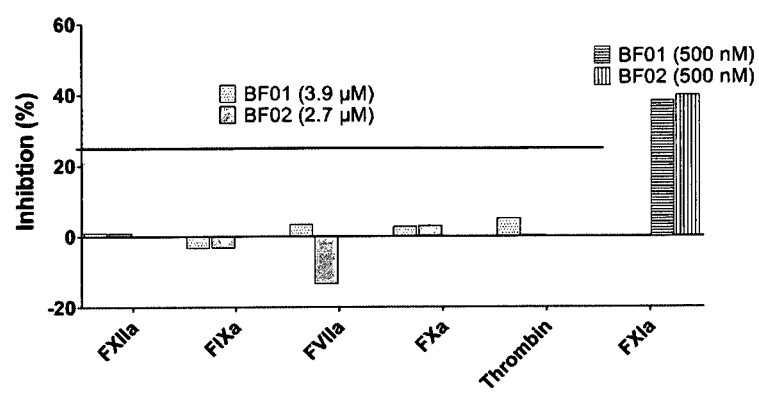
FIG. 16: Effects of BF01 and BF02 on various procoagulant proteases in the blood coagulation cascade were evaluated. Results indicate that both proteins are selective inhibitors of FXIa.
Figures 17A, 17B, 17C, 17D, 17E, 17F, 17G:
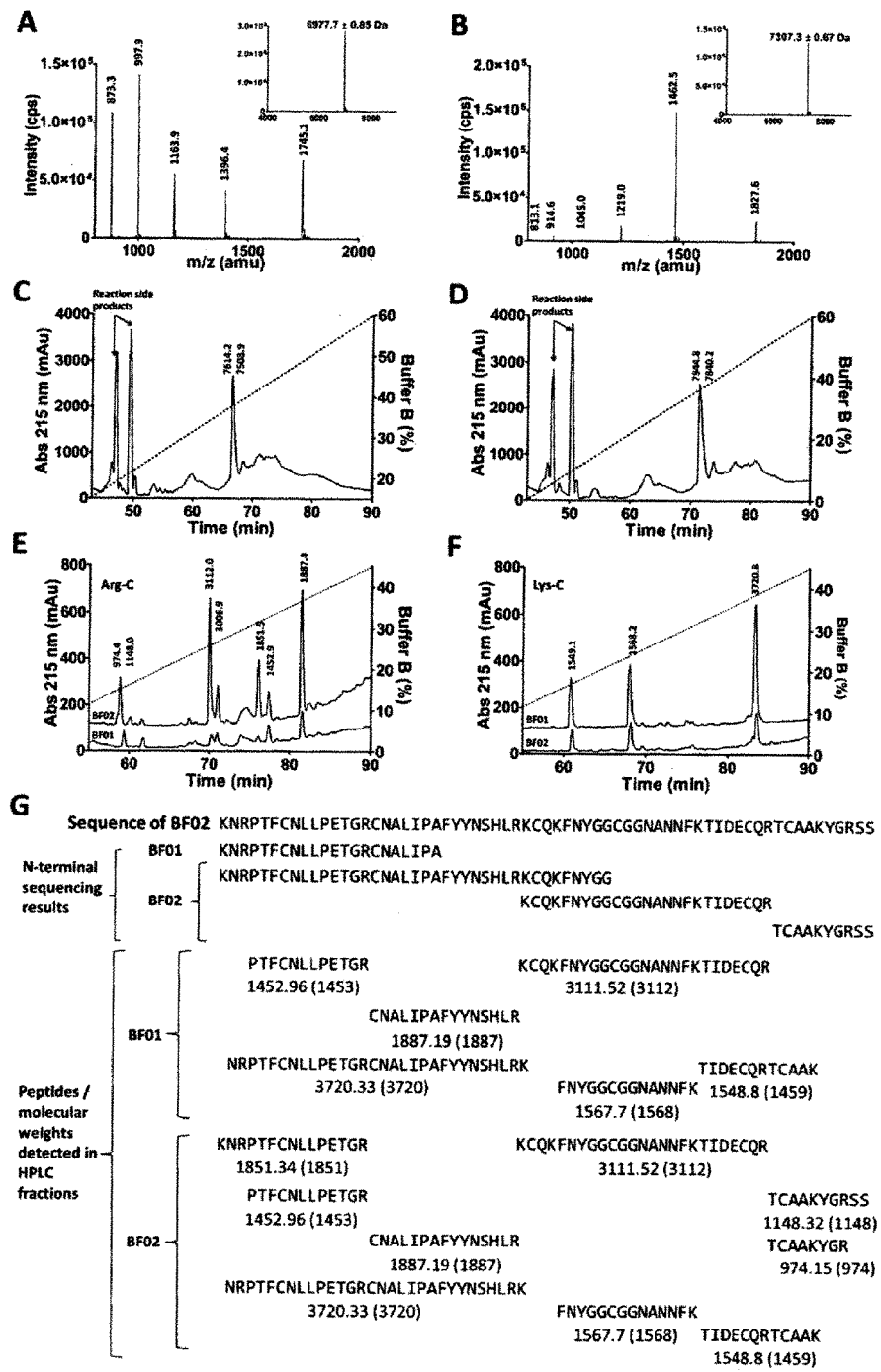
FIGS. 17A-17G: Sequence determination of BF01/02. (17A) ESI-MS profile of BF01; (17B) ESI-MS profile of BF02; (17C-17D) HPLC profile of BF01/02 after pyridylethylation; the major product had a molecular weight of 7614.2 Da (BF01)/7944.8 Da (BF02), while molecular weight of 7508.9 Da (BF01)/7840.2 Da (BF02) (minus one 4-pyridylethyl group) was also detected in the same peak. (17E) HPLC profile of BF01/02 after Arg-C digestion; the molecular weights of major peaks are shown. (17F) HPLC profile of BF01/02 after Lys-C digestion; the molecular weights of major peak are shown. (17G) The amino acid sequence of BF01/02 was determined by N-terminal sequencing of pyridylethylated BF01/02 and peptides from Arg-C digestion of BF02 (SEQ ID NOs: 19 and 21-39). The molecular weights detected in Arg-C and Lys-C digestion were assigned to the expected peptides and these peptides were aligned with the full length sequence of BF02. The molecular weights of peptides are shown in the format of (calculated mass/determined mass). BF01 showed identical HPLC profile as BF02 except the presence of "RSS" at the C-terminal. The presences of two isoforms of Kunitz-type inhibitor that differ by "RSS" in the C-terminal in *Bungarus fasciatus* venom were recorded earlier.

To determine the protease specificity, BF01 and BF02 were screened against several procoagulant serine proteases in the coagulation pathway (FIG. 16) and were found to selectively inhibit FXIa. The more abundant BF01 was further screened against 10 serine proteases (thrombin, FVIIa, FIXa, FXa, FXIa, FXIIa, Plasmin, Kallikrein, APC, Urokniase) in the coagulation cascade. Other than FXIa, BF01 (10 µM) did not inhibit the activities of other serine proteases (FIG. 9L).

Amino Acid Sequences of Novel Anticoagulants

Figure 9M:
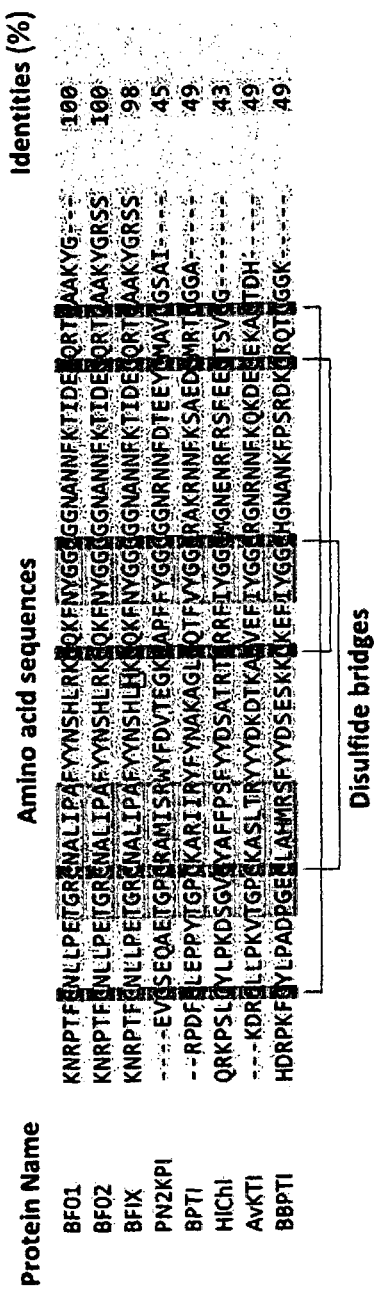

BF01 and BF02 were subjected to pyridylethylation, Lys-C/Arg-C digestion and protein sequencing. Elution profile of peptide fragments and sequencing data suggested that BF01 and BF02 are isoforms (FIG. 17A-17G); BF02 has three additional amino acid residues at the C-terminal compared to BF01. BLAST searches indicated that BF01 and BF02 were Kunitz-type protease inhibitors. BF02 is only one residue different from a previously reported chymotrypsin inhibitor, Kunitz IX (BFIX), isolated from the venom of the same species. However, its haemostatic effect has not been previously reported. The sequences of BF01 and BF02 were aligned with BFIX, PN2KPI and other Kunitz-type chymotrypsin or trypsin inhibitors (FIG. 9M). Interestingly, BF01/BF02 shows limited similarity with PN2KPI (45% identity; 58% similarity). We focused on BF01 for further studies and it was named as Fasxiator (*B. fasciatus* FXIa inhibitor).

Recombinant Expression of Fasxiator

Figures 10A, 10B, 10C, 10D, 10E, 10F:
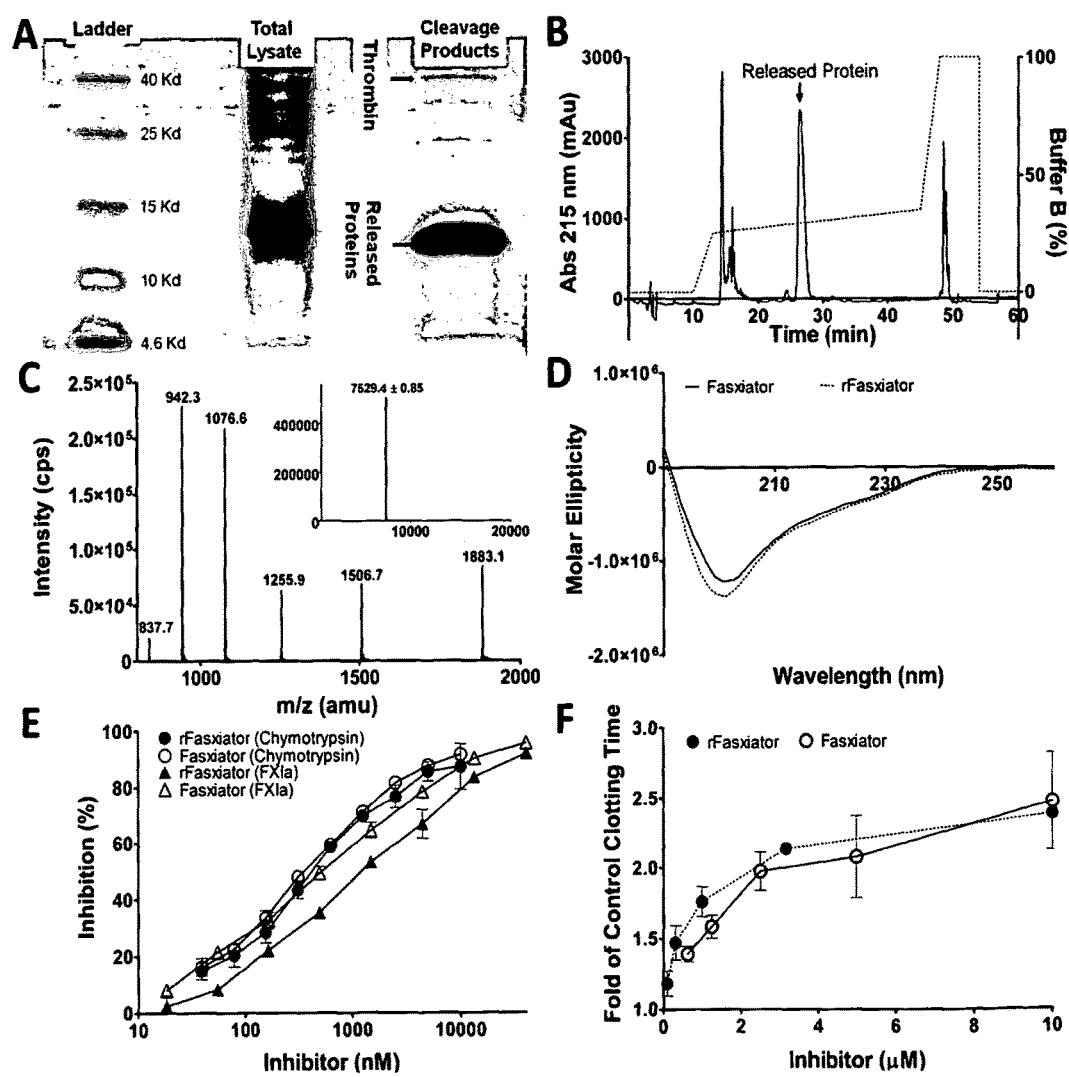
FIGS. 10A-10F: Recombinant expression and purification of rFasxiator. (10A) SDS PAGE of total bacterial lysate and thrombin cleavage product from Ni-NTA beads; (10B) Purification of thrombin cleavage products using RP-HPLC; (10C) ESI-MS profile of purified recombinant protein (rFasxiator). rFasxiator has an additional five amino acid residues in the N-terminal compared with Fasxiator. (10D) Circular dichroism spectra of Fasxiator and rFasxiator; (10E) Inhibition of chymotrypsin and FXIa activities by Fasxiator and rFasxiator; (10F) Prolongation of aPTT by Fasxiator and rFasxiator. Results indicate that Fasxiator and rFasxiator share similar structure and activity (10D-10F).

Due to limited venom supply, Fasxiator was recombinantly expressed in *E. coli* and refolded. The bacterial lysate and refolded protein were visualized on a 15% SDS PAGE using Coomassie blue staining (FIG. 10A). The refolded protein was further fractionated by RP-HPLC (FIG. 10B). Recombinant Fasxiator (rFasxiator) has an additional five amino acid residues "GSEFM" in the N-terminal compared to BFO 1. The identity and homogeneity of rFasxiator was ascertained by ESI-MS (FIG. 10C); MW of 7529.40±0.85 Da matches the calculated mass from the sequence. rFasxiator showed similar secondary structure (FIG. 10D), inhibitory effect on FXIa and chymotrypsin (FIG. 10E) and anticoagulant activity (FIG. 10F) compared to native Fasxiator. Thus, rFasxiator is structurally and functionally similar to native Fasxiator and was used in all subsequent functional studies.

rFasxiator Selectively Inhibits FXIa

Figures 11A, 11B, 11C, 11D:
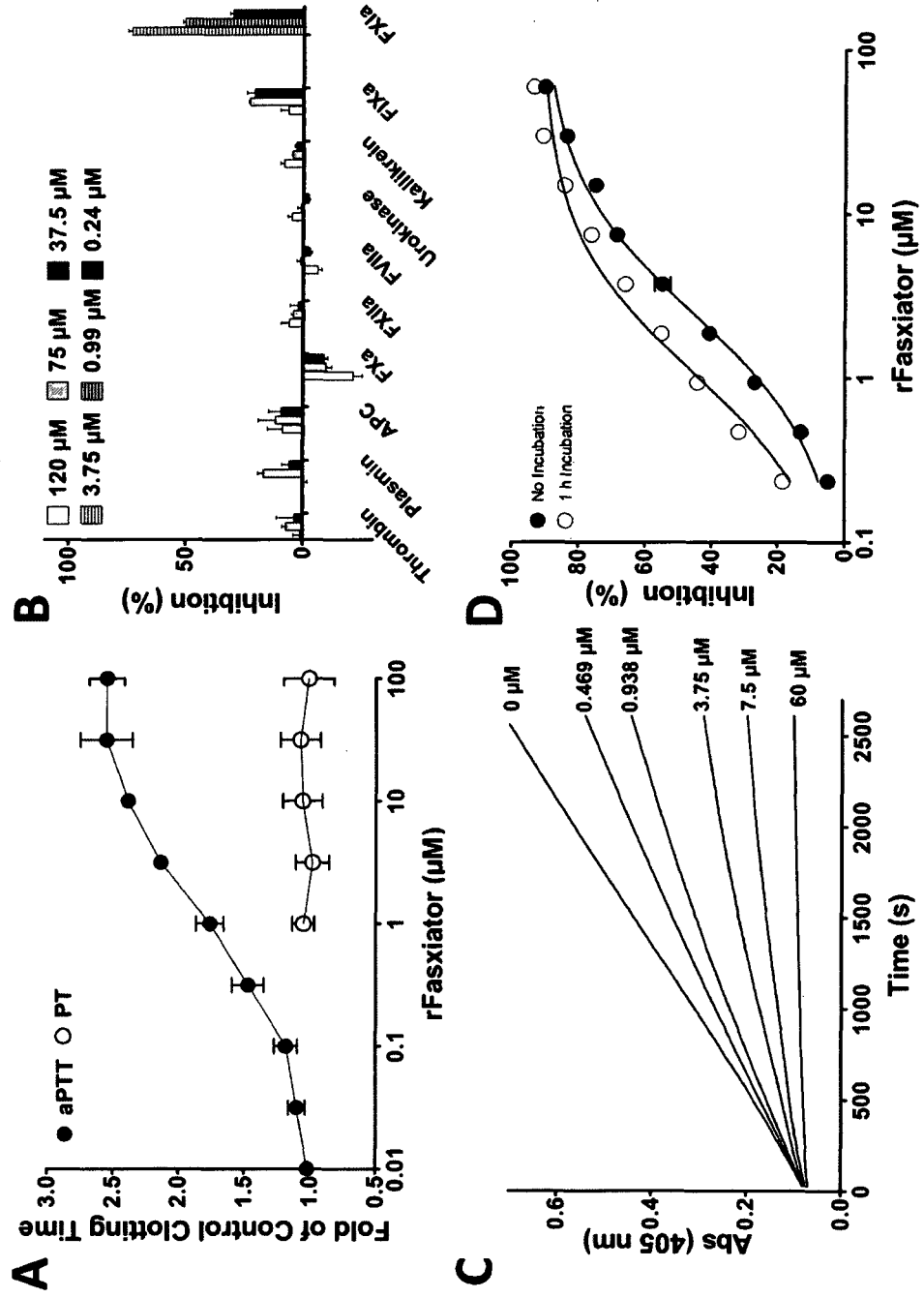
FIGS. 11A-11D: Anticoagulant activity and protease specificity of rFasxiator. (11A) Effect of rFasxiator on aPTT and PT. rFasxiator prolonged aPTT in a dose-dependent manner, while it had no significant effect on PT; (11B) rFasxiator selectively inhibits FXIa among the serine proteases in the blood coagulation cascade. (11C) Progress curves of 52366 cleavage by FXIa in the presence of different concentrations of rFasxiator. (11D) Effects of incubation time on the inhibition of FXIa by rFasxiator. Dose-inhibition curve shifts to the left with 1 h incubation. Time-dependent increase in inhibiting effect of rFasxiator indicates that rFasxiator is a slow-type inhibitor.
Figure 18:
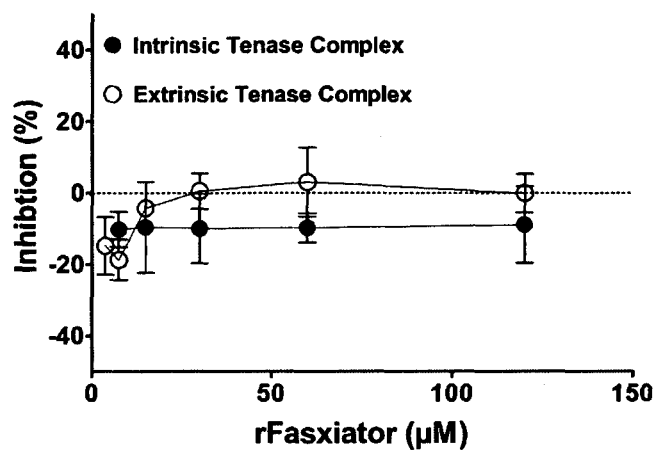
FIG. 18: Effect of rFasxiator on the intrinsic and the extrinsic tenase complexes. rFasxiator had no significant inhibitory effect on the activity of both complexes.
Figures 19A, 19B:
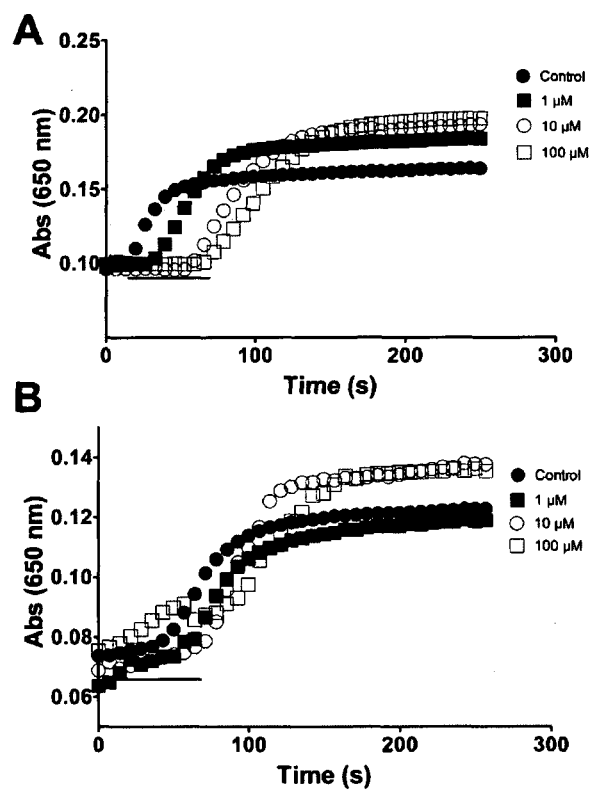
FIGS. 19A-19B: Effects of rFasxiator on aPTT of human (19A) and murine (19B) plasma. Clotting of plasma was monitored by absorbance at 650 nm. aPTT of human plasma was prolonged by rFasxiator, but rFasxiator had no significant effect in murine plasma. rFasxiator does not inhibit murine FXIa or inhibits it in a much less potency than inhibiting human FXIa.
Figures 20A, 20B, 20C, 20D, 20E, 20F:
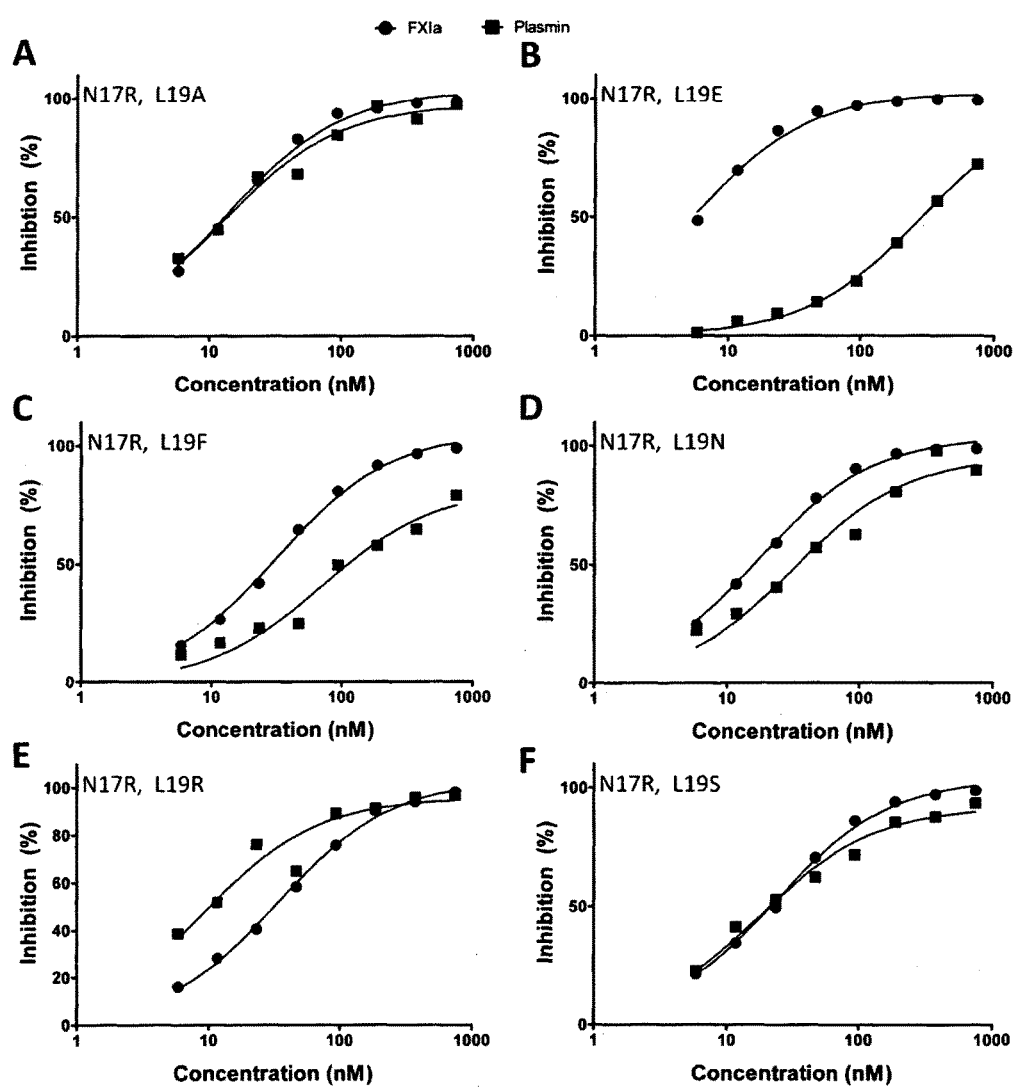
FIGS. 20A-20F: Selectivity of Set 2 variants. In order to increase the selectivity of rFasxiatorN17R, we have mutated the P2' residue "L" to A/E/F/N/R/S. Since rFasxiatorN17R suffered from poor selectivity toward Plasmin, for a screening, we tested the dose dependent inhibition of the new variants against FXIa and Plasmin (20A-20F) without preincubation of inhibitor with proteases. rFasxiatorN17R, L19E showed best selectivity toward FXIa over plasmin.
Figures 21A, 21B, 21C:
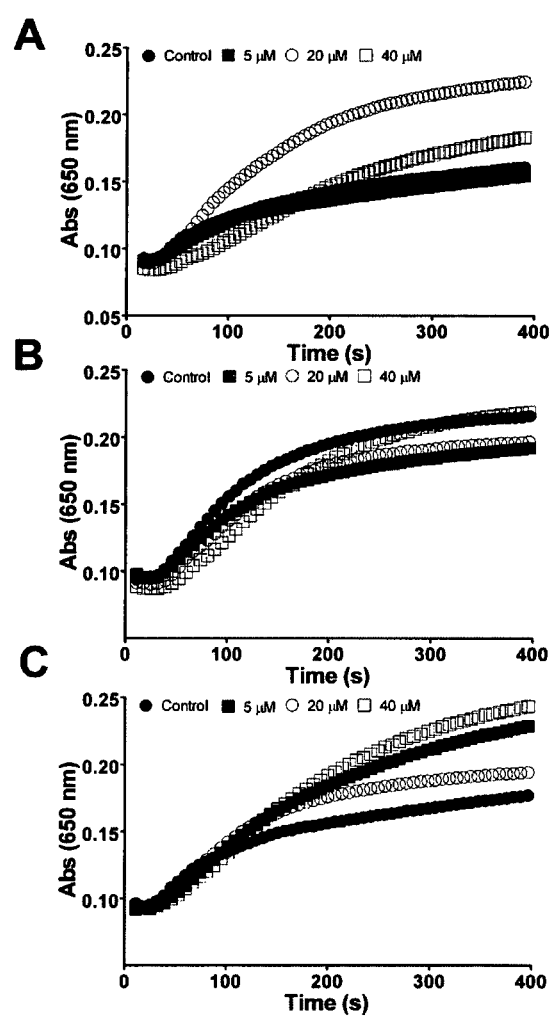
FIGS. 21A-21C: rFasxiator$_{N17R,L19E}$ was not able to prolong PT in human plasma up to a concentration of 40

The anticoagulant activity and protease specificity of rFasxiator were determined. rFasxiator doubled aPTT at ~3 µM but had no significant effect on PT up to 100 µM (FIG. 11A). rFasxiator was tested for its effect on extrinsic and intrinsic tenase complexes (FIG. 18), as well as various serine proteases involved in the coagulation cascade (FIG. 11B). rFasciator selectively inhibits FXIa (IC50~1.5 µM); it failed to significantly inhibit other serine proteases even at 120 µM. The inhibition kinetics of rFasxiator on FXIa using chromogenic substrate S2366 (FIG. 11C-11D) indicated that rFasxiator is a slow-type inhibitor, with $IC_{50}$ values changing from 3 µM (no pre-incubation) to 1.5 µM (1 hr pre-incubation). In contrast, rFasxiator was a fast type inhibitor of chymotrypsin with an $IC_{50}$ of 1 µM (data not shown).

rFasxiator Prolongs aPTT Through Inhibition of FXIa

As rFasxiator inhibits the cleavage of small peptide substrates by FXIa, we examined the interaction of rFasxiator with FXIa.

Figures 12A, 12B, 12C, 12D:
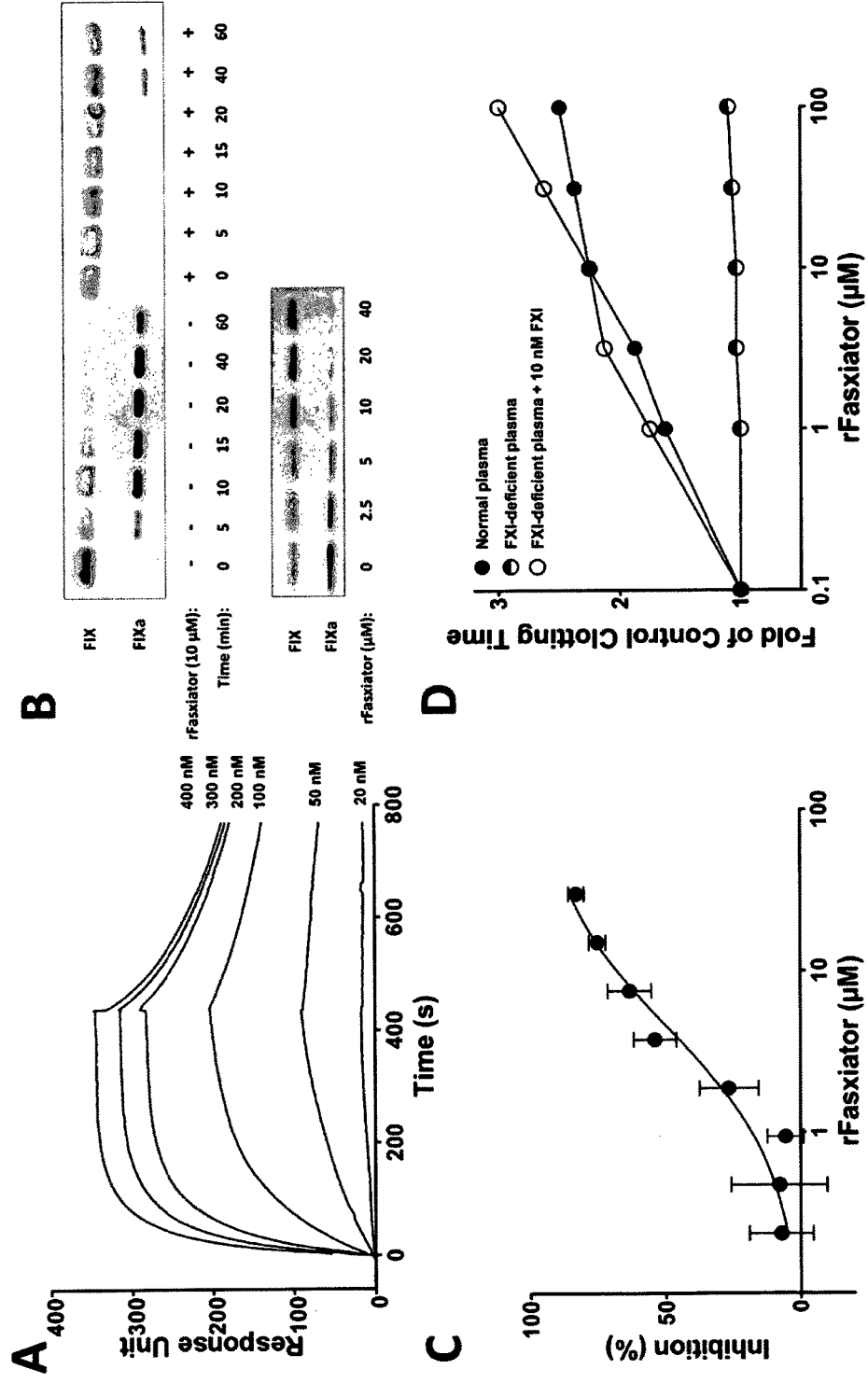
FIGS. 12A-12D: rFasxiator interacts with and inhibits FXIa. (12A) High affinity binding of rFasxiator to FXIa. In SPR studies, rFasxiator was immobilized and various concentrations of FXIa were used as the analyte. FXIa binds to rFasxiator with a KD of 20.15 nM. rFasxiator also binds chymotrypsin with a KD of 29.3 nM (data not shown); (12B) Inhibition of cleavage of FIX by rFasxiator. FIX and FIXa were detected by western blotting. rFasxiator shows time-dependent (upper panel) and dose-dependent (lower panel) inhibition of activation of FIX; (12C) Inhibition of activation of FIX by rFasxiator. The FIXa generated was quantified by its hydrolytic activity on chromogenic substrate (activity in the absence of rFasxiator was defined as 100%); (12D) FXIa is the target for rFasxiator for its anticoagulant effects. Data points represent average of duplicates. aPTT is prolonged by rFasxiator in normal plasma, but not in FXI-deficient plasma. The anticoagulant effects were observed when 10 nM FXI was added to FXI-deficient plasma. Thus, FXI is the main target of rFasxiator.
Figures 13A, 13B, 13C, 13D, 13E:
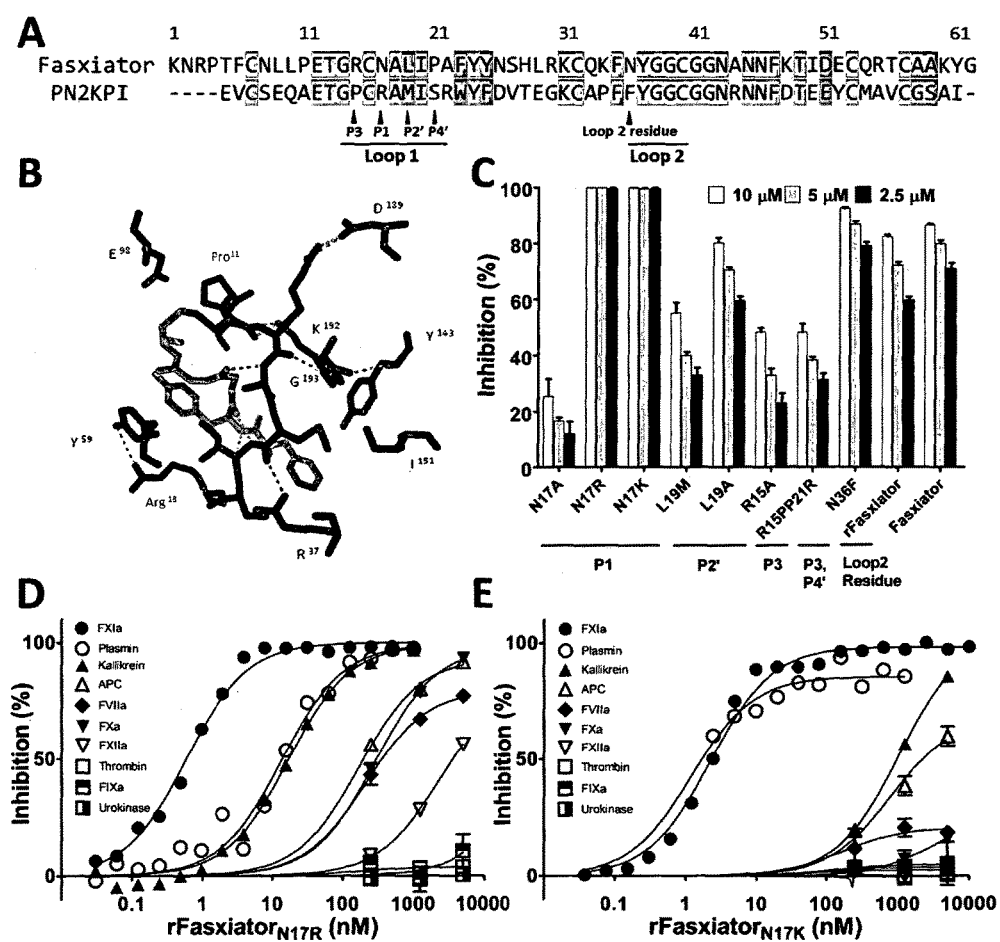
FIGS. 13A-13E: Structure-function relationships of rFasxiator. (13A) Sequence alignment of two FXIa-specific Kunitz-type inhibitors (SEQ ID NOs: 1 and 14). Yellow color: identical residues; green color: conserved residues. To increase potency and selectivity of rFasxiator, we selected residues (identified by arrow heads) that are involved in interaction with FXIa; (13B) Interaction between PN2KPI and FXIa light chain (protease domain), FXIac, as determined by 3D structure of the complex. Only relevant segments are shown. Red: FXIa residues involved in interaction with PN2KPI; Dark blue: Loop I (GPCRAMISR) residues of PN2KPI; Green: Loop 2 (FYGGC) residues of PN2KPI; Light blue: Hydrogen bonds; The guanidinium group of Arg15 (P1) in PN2KPI interacts with the carboxylate group of Asp 189 of FXIac to form a salt bridge in the S1 pocket; Pro13 (P3) help Cys14 (P2) and Gly12 (P4) found hydrogen bonds with Lys192 of FXIac by turning the backbone; Met17 (P2') and Ser19 (P4') interact with Arg37D of FXIa; Phe34 of PN2KPI is in van der Waals contact with Tyr143 of FXIac. (13C) FXIa inhibition by site-directed mutants of rFasxiator (40 min pre-incubation with FXIa). Two mutants rFasxiatorN17R and rFasxiatorN17K show significant increase in their potency; Selectivity profiles of rFasxiatorN17K (13D) and rFasxiatorN17R (13E) (30 min pre-incubation of enzyme and inhibitor). Further mutations are needed for improving selectivity.
Figures 14A, 14B, 14C, 14D, 14E, 14F, 14G:
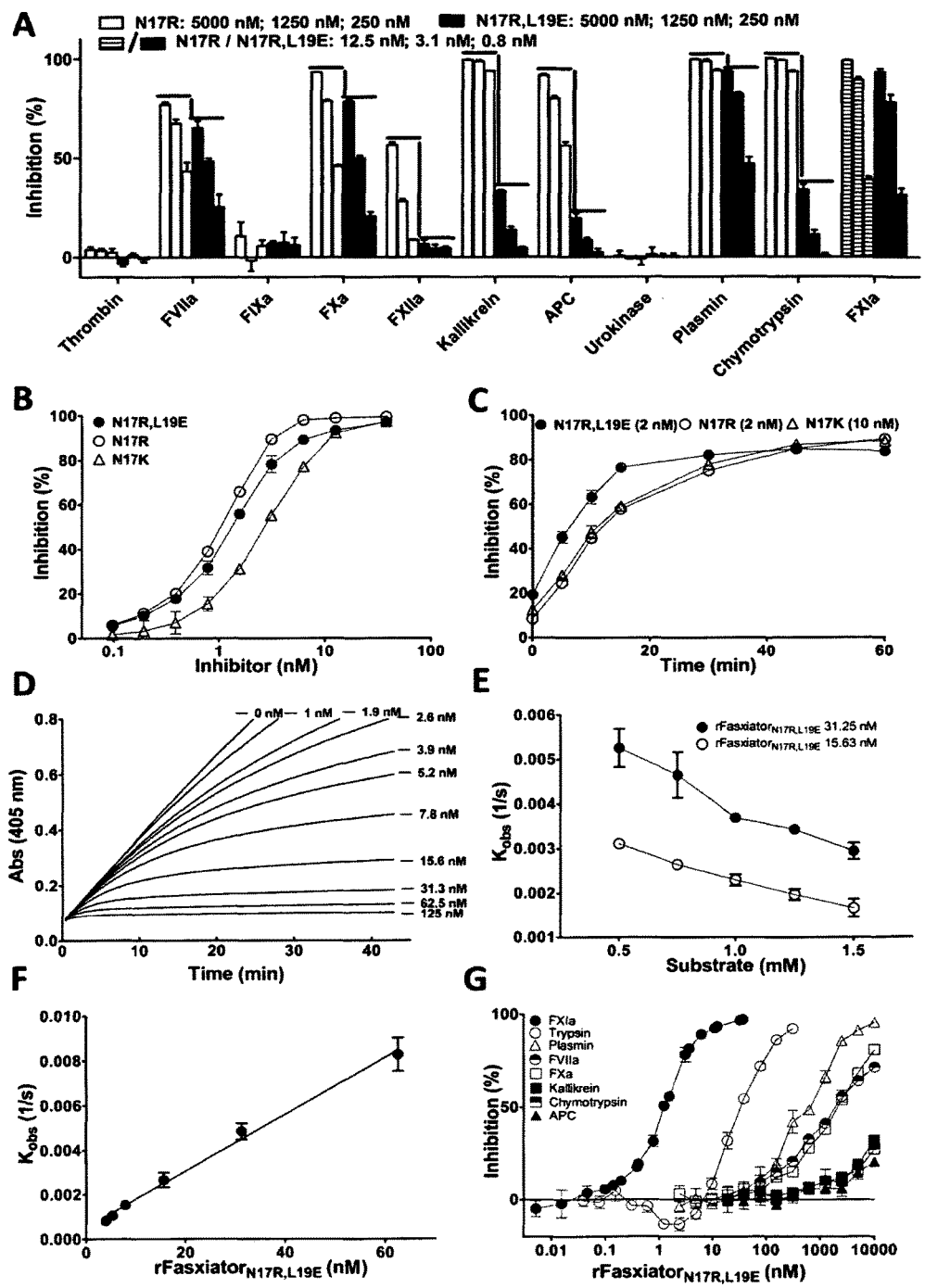
FIGS. 14A-14G: Functional characterization of rFasxiator$_{N17R,L19E}$. (14A) Comparison of selectivity between rFasxiator$_{N17R,L19E}$ and rFasxiator$_{N17R}$. rFasxiator$_{N17R,L19E}$ has better selectivity over FVIIa, FXa, FXIIa, kallikrein, APC, plasmin, and chymotrypsin; (14B) Dose-dependent inhibition of FXIa by rFasxiator$_{N17R,L19E}$, rFasxiator$_{N17R}$ and rFasxiator$_{N17K}$ (40 min pre-incubation); (14C) Time-dependent inhibition of FXIa byj rFasxiator$_{N17R,L19E}$, rFasxiator$_{N17R}$ and rFasxiator$_{N17K}$. (14D) Effect of rFasxiator$_{N17R,L19E}$ on cleavage of S2366 by FXIa$_{N17R,L19E}$. The curves were fitted into Eqn 1 to determine $K_{obs}$; (14E) $K_{obs}$ were plotted against substrate concentration. The decrease in inhibition with increasing concentrations of substrate suggests that rFasxiator$_{N17R,L19E}$ is a competitive inhibitor; (14F) Kobs were plotted against rFasxiator$_{N17R,L19E}$ concentration. A straight line indicates that rFasxiator$_{N17R,L19E}$ is a type I slow-type inhibitor. (14G) Selectivity of rFasxiator$_{N17R,L19E}$ against different serine proteases (40 min pre-incubation). rFasxiator$_{N17R,L19E}$ has high potency and good selectivity to FXIa.
Figures 15A, 15B, 15C:
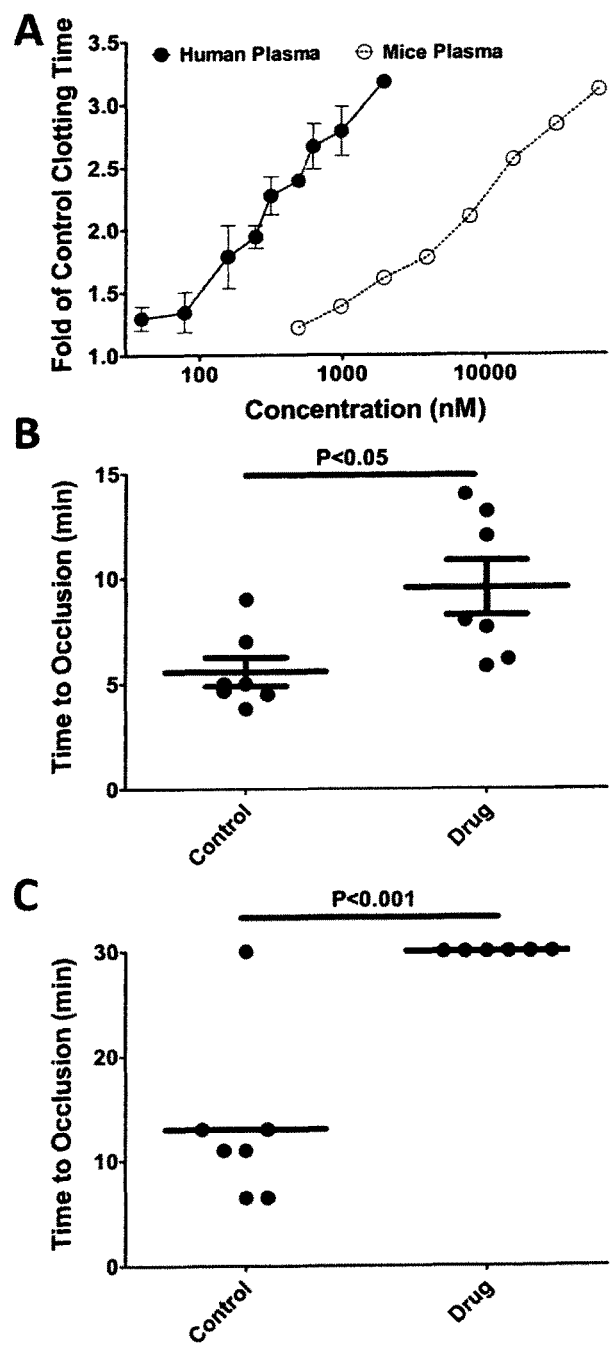
FIGS. 15A-15C: Anti-thrombotic effect of rFasxiator$_{N17R,L19E}$ in FeCl$_3$-induced carotid artery thrombosis model in mice. (15A) Potency of rFasxiator in prolonging aPTT in both human and murine plasma. Human plasma data represents average of triplicates, while mice plasma data represents average of duplicates; (15B) Thrombosis was induced by 6% FeCl$_3$, 2 mm*2 mm filter paper; 200 μg rFasxiator$_{N17R,L19E}$ per mice. Significant differences between two groups were calculated using paired t-test, P<0.05; (15C) Thrombosis was induced by 5% FeCl$_3$, 1 mm*1 mm filter paper; 300 μg rFasxiator$_{N17R,L19E}$ per mice. Significant differences between two groups were calculated using t-test were detected, P<0.001.

Firstly, we determined the affinity of rFasxiator to FXIa using surface plasmon resonance (SPR). rFasxiator was immobilized on the surface of a COOH5 chip and different concentrations of FXIa were used as analyte (FIG. 12A). The sensorgrams indicated strong interaction of rFasxiator with FXIa; we calculated a $K_D$ of 20.15 nM assuming a 1:1 stoichiometry and single step binding. Similarly, rFasxiator interacted with chymotrypsin with a $K_D$ of 29.3 nM (data not shown). This $K_D$ value is similar to that of chymotrypsin inhibitor BFIX (~50 nM) reported in earlier.

Secondly, we examined the effect of rFasxiator on the cleavage of FIX, the physiological substrate of FXIa. The cleavage of FIX by FXIa was monitored using western blotting in both the presence and absence of 10 µM rFasxiator. The presence of rFasxiator slowed down the cleavage of FIX (FIG. 12B, upper panel). At 15 min, rFasxiator exerted a dose-dependent inhibition of FIX cleavage by FXIa (FIG. 12B, lower panel). The amount of cleavage product, FIXa, was also quantified by the chromogenic assays (FIG. 12C). rFasxiator was found to inhibit the activation of FIX with a similar potency as the inhibition of FXIa cleavage of small peptide substrates ($IC_{50}$~3 µM).

Finally, we tested the effect of rFasxiator on the prolongation of aPTT in normal and FXI-deficient human plasma.

rFasxiator failed to prolong aPTT in FXI-deficient plasma, while it was able to prolong aPTT in FXI rescued plasma with a similar potency as in normal human plasma (FIG. 12D). This result strongly suggests that FXI is necessary for rFasxiator's function as an anticoagulant, whereby prolongation of aPTT could have been achieved via the inhibition of FXIa. To the best of our knowledge, this is the first exogenous protein that selectively targets FXIa.

Improvement of rFasxiator Potency by Site-Directed Mutagenesis

As the in vitro studies showed that rFasxiator prolonged aPTT through inhibition of FXIa, the anticoagulant effect of rFasxiator was tested in mouse plasma. Unfortunately, unlike in human plasma, rFasxiator failed to prolong aPTT (FIGS. 19A-19B). This is probably due to the weaker inhibition of murine FXIa.

To improve the potency and selectivity of rFasxiator, specific residues in loops 1 and 2 of rFasxiator were selected based on the co-crystal structure of PN2KPI and FXIa catalytic domain (accession Id: 1ZJD) 25 (FIG. 13A, 13B). The following single point mutations were carried out: (1) P1 substitutions N17A, N17K and N17R; (2) P2' substitutions L19A and L19M; (3) P3' substitution R15A; and (4) P3, P4' exchange R15P,P21R (all in loop 1) and (5) N36F substitution (in loop 2). All the mutants were expressed and purified using the same procedures as the rFasxiator protein. The homogeneity and identity of each mutant were ascertained by ESI-MS (Table 3).

All mutants were tested for FXIa inhibition (FIG. 13C). Mutation of P1, as expected, had a significant effect on the inhibitory activity; rFasxiatorN17A lost ~75% of the inhibitory activity, while mutation to positively charged Lys and Arg significantly enhanced, it. All the other substitutions at P2', P3', P4' and P3 resulted in decreased or had no significant effect on the inhibitory activity. We determined the specificity of rFasxiator$_{N17K}$ and rFasxiator$_{L17R}$ for the serine proteases in the coagulation pathway. Although these mutations increased the potency, the selectivity was lost: rFasxiator$_{N17K}$ has similar selectivity towards FXIa and plasmin (FIG. 13D), while rFasxiatorNl7R is only marginally selective towards FXIa compared to plasmin and kallikrein (FIG. 13E).

To enhance the selectivity of rFasxiator, rFasxiator$_{N17R}$ was chosen for further modifications. The P2' L residue was mutated to A/E/F/N/R/S. All the double mutants were then evaluated for their ability to inhibit FXIa and plasmin (FIGS. 20A-20F). rFasxiator$_{N17R,L19E}$ showed the best selectivity among all mutants toward FXIa. Comparison of selectivities revealed that rFasxiator$_{N17R,L19E}$ had better selectivity over FVIIa, FXa, FXIIa, kallikrein, APC, plasmin, and chymotrypsin than rFasxiator$_{N17R}$ (FIG. 14A). The dose-response studies indicated that the $IC_{50}$ for FXIa inhibition by rFasxiator$_{N17R}$, rFasxiator$_{N17K}$ and rFasxiator$_{N17R,L19E}$ with 40 min incubation were 0.94 nM, 2.96 nM and 1.26 nM, respectively (FIG. 14B). The inhibitory potencies of these mutants increased with prolongation of incubation time with FXIa (FIG. 14C) and hence are also slow-type inhibitors. Thus, with two mutations in rFasxiator$_{N17R,L19E}$, we significantly improved the inhibitory potency (1000 fold) and selectivity towards FXIa.

Inhibition Kinetics of rFasxiator$_{N17R,L19E}$

To further understand the interaction with FXIa, we determined the kinetic parameters of rFasxiator$_{N17R,L19E}$. Progress curves of cleavage of S2366 by FXIa with (i) fixed substrate concentration and different concentrations of rFasxiaotor$_{N17R,L19E}$ (FIG. 14D), and (ii) fixed rFasxiator$_{N17R,L19E}$ concentration and different concentrations of S2366 were plotted (data not shown). The curves were fitted into Eqn 1 (Materials and Methods) to determine $K_{obs}$. $K_{obs}$ decreases with the increasing substrate concentration (FIG. 14E). Hence, rFasxiator$_{N17R,L19E}$ is a competitive inhibitor. As the plot of $K_{obs}$ versus rFasxiator$_{N17R,L19E}$ concentrations (FIG. 14F) shows a straight line, rFasxiator$_{N17R,L19E}$ is a type I slow-type inhibitor with a $K_i$ of 0.86 nM using Eqn 2 and 3 (Materials and Methods). For comparison, we also determined the dose-dependent inhibition of other serine proteases (FIG. 14G). $K_i$ values of rFasxiator$_{N17R,L19E}$ in inhibition of trypsin, plasmin, FXa, FVIIa and kallikrein were obtained and compared with those of PN2KPI (Table 1). rFasxiator$_{N17R,L19E}$ inhibited FXIa with similar potency as PN2KPI (0.86 nM versus 0.81 nM), while their selectivity are different. rFasxiator$_{N17R,L19E}$ dropped 2-5 folds in selectivity against plasmin, FXa and FVIIa, while gained 28.9 fold and 323 folds selectivity against kallikrein and trypsin comparing to PN2KPI. Thus we have developed a new selective inhibitor of FXIa, which has similar potency as the endogenous physiological inhibitor.

rFasxiator$_{N17R,L19E}$ Prolongs $FeCl_3$-Induced Carotid Artery Thrombosis

The anticoagulant effects of rFasxiator$_{N17R,L19E}$ were quantified by aPTT and PT in human and murine plasma. rFasxiatorN17R,L19E prolonged aPTT in a dose-dependent manner (FIG. 15A) and doubled aPTT at around 300 nM, but had no significant effect on PT up to 40 μM in human plasma (FIGS. 21A-21C). Similarly, it also prolonged aPTT in mice plasma in a dose-dependent manner, however, the potency was about 10 fold weaker (doubled aPTT at ~4 μM). Thus, rFasxiator$_{N17R,L19E}$ exerts its anticoagulant effects through the intrinsic pathway.

We used $FeCl_3$-induced carotid artery thrombosis model to evaluate the antithrombotic effects of rFasxiator$_{N17R,L19E}$. In the first set of experiments, 0.2 mg rFasxiator$_{N17R,L19E}$ almost doubled the occlusion time (5.57 min versus 9.55 min) in the test animals compared to control animals (FIG. 15B). While all the control animals conformed to a one step formation of thrombus (flow gradually reduced to zero and maintained until the end point), four of the treated animals showed diffused events (flow reduced first, bounced back to normal and reduced again). We, therefore, repeated the animal experiments with the increased inhibitor (0.3 mg) and reduced the injury strength. Under these conditions, 6 control animals attained occlusion times in around 10 min, but no occlusion was found until 30 min in the 7th mouse. In treated animals there was no occlusion until the end of experimental period (30 min) (FIG. 15C). Thus, rFasxiator$_{N17R,L19E}$ exhibited antithrombotic effects in mouse carotid artery thrombosis. The in vivo data complemented with our in vitro data demonstrates the potent anticoagulant activity of rFasxiator$_{N17R,L19E}$.

Discussion

Fasxiator described here is the first exogenous FXIa inhibitor. It is a Kunitz-type serine protease inhibitor. It has only one residue different from a chymotrypsin inhibitor BFIX isolated from same venom. However, the haemostatic effects of BFIX were not explored. Fasxiator (FXIa and chymotrypsin inhibitor) showed low identity (<50%) with PN2KPI (trypsin and FXIa inhibitor), BPTI (trypsin, plasmin, kallikrein and FXIa inhibitor), HlChl (chymotrypsin inhibitor), AvKTI (trypsin and plasmin inhibitor) and BBPTI-1 (chymotrypsin inhibitor) (FIG. 9N). Because of its distinct sequence, we characterized the anticoagulant property, serine protease specificity and the inhibitory effects of rFasxiator on FXIa in detail. rFasxiator inhibits intrinsic pathway, while leaves extrinsic pathway unaffected. rFasxiator selectively inhibits FXIa among the serine proteases and tenase complexes involved in the coagulation cascade. Using four completely different methods (SPR, western blotting, chromogenic and standard coagulation assays), we have shown that rFasxiator interacts with FXIa with high affinity and inhibits cleavage and activation of FIX, and thus exerts its anti-coagulation function through targeting FXIa (FIGS. 11A-11D). Thus, we have identified and successfully expressed rFasxiator, a selective FXIa inhibitor from *B. fasciatus* venom.

Further characterization of rFasxiator in mouse models was hindered by its inability to prolong aPTT in murine plasma (FIGS. 19A-19B). Further, the inhibitory effects of rFasxiator on FXIa are relatively weak compared to PN2KPI and several other small inhibitors of FXIa (μM versus nM). Thus, we attempted to increase the potency of rFasxiator through specific point mutations. The major challenge is to achieve both strong potency and high selectivity, as most of the coagulation factors are trypsin-like proteases with their selectivity dependent on minor differences in the active-site pocket. To understand molecular details of interaction between FXIa and Kunitz inhibitor, we used the co-crystal structure of PN2KPI and FXIa catalytic domain (FXIac) (PDB: 1ZJD) as a reference. The key interactions between PN2KPI and FXIa are as follows: (a) the guanidinium group of Arg15 (P1) in PN2KPI interacts directly with the carboxylate group of Asp 189 of FXIac to form a salt bridge in the S1 pocket; (b) Pro13 (P3) helps Cys14 (P2) and Gly12 (P4) to form hydrogen bonds with Lys192 of FXIac by turning the backbone; (c) Met17 (P2') and Sen 9 (P4') interact with Arg37D of FXIa; and (d) Phe34 of PN2KPI is in van der Waals contact with Tyr143 of FXIac. Thus, we chose the corresponding residues (P1, P3, P2', P4' and the first residue in loop II) in rFasxiator for mutagenesis study. As predicted, the P1 residue is the most essential residue for inhibitory activity. Changing Asn17 (P1) in rFasxiator to FXIa preferred residue, arginine and lysine, significantly improved the potency of inhibition (FIGS. 13A-13E). However, mutations designed to mimic the loop 1 structure of PN2KPI failed to improve inhibitory potency.

rFasxiator$_{N17K}$ and rFasxiator$_{N17R}$ showed 100-1000 times increment in potency. However, further efforts were needed to optimize the specificity and selectivity of rFasxiator$_{N17K}$ and rFasxiator$_{N17R}$. Since mutations in P2' significantly affected the selectivity of PN2KPI, we mutated Leu19 to residues of different properties. The properties/residues are: Small/Ala; Nucleophilic/Ser; Hydrophobic/Pro; Aromatic/Phe; Acidic/Glu; Amide/Asn; and Basic/Arg. Except for rFasxiator$_{N17R,L19P}$, all the other mutants were successfully expressed and evaluated for their protease selectivity. Glutamate in P2' position is the least preferred residue by kallikrein, APC, plasmin, FXIIa and chymotrypsin; rFasxiator$_{N17R,L19E}$ showed dramatic loss of inhibitory effect on these enzymes (FIG. 14A). In contrast, FXIa tolerated an acidic residue in P2' position. This Glutamate may interact with Arg37D of FXI and form a salt bridge. Thus, by modifying P1 and P2' sites of rFasxiator, we have successfully improved the potency and specificity of rFasxiator. These results suggest that it is possible to change potency/selectivity of type inhibitors to a specific serine protease with only limited modifications.

The comparison of rFasxiator$_{N17R,L19E}$ with PN2KPI (Table 1) indicated that rFasxiator$_{N17R,L19E}$ inhibited FXIa with similar potency as PN2KPI (0.86 nM as compared to 0.81 nM), but their specificities are different.

rFasxiator$_{N17R,L19E}$ treated animals were protected against $FeCl_3$-induced carotid artery thrombosis and the protective effects are related to injury strength (FIGS. 15A-15C). Similar observations were also made with FXI-deficient mice; FXI-deficient mice were fully protected against thrombosis induced by 5% $FeCl_3$, partially protected against 7.5% $FeCl_3$, and showed almost no protection against 10% $FeCl_3$. Thus, disruption of FXI provides milder protection against artery thrombosis, unlike thrombin inhibition. This may be because thrombin is downstream of FXIa in the thrombus formation and thus a more direct target for inhibition of thrombus growth. The diffused pattern observed suggested that rFasxiator$_{N17R,L19E}$, played a role in the growth/stability of thrombus, which is consistent with the phenomena observed elsewhere. Platelet deposition and fibrin accumulation was reduced in vascular graft occlusion in FXI antibody treated baboon and thrombi inside the carotid artery was flushed away by blood flow in some of the PN2KPI treated mice. Thus, rFasxiator$_{N17R,L19E}$ prevent thrombosis formation in vivo. To evaluate toxicity, we administered rFasxiator or rFasxiator$_{N17R,L19E}$ at a single dosage of 50 mg/kg through intraperitoneal injections or 10 mg/kg through intravenous injections in C57BL/6 mice. These mice showed no pathologic symptoms and they survived more than three days without any complications. Thus, rFasxiator and rFasxiator$_{N17R,L19E}$ have low/no toxicity in healthy animals.

In summary, we have isolated a novel exogenous FXIa inhibitor, Fasxiator from *B. fasciatus* venom. Recombinant double mutant has high potency and selectivity towards FXIa and it inhibits occlusion in mouse carotid artery thrombosis model and has potential in developing antithrombotic drugs.

TABLE 1

Comparison of $K_i$ of rFasxiator$_{N17R,L19E}$ with PN2KPI

| | rFasxiator$_{N17R,L19E}$/ Fold to FXIa | PN2KPI/ Fold to FXIa |
|---|---|---|
| FXIa | 0.86 nM/1 | 0.81 nM/1 |
| Trypsin | 9.7 nM/11.3 | 0.03 nM/−27 |
| Kallikrein | 5297.7 nM/6160.1 | 183 nM/225.9 |
| Plasmin | 145.5 nM/169.2 | 459 nM/566.7 |
| FVIIa | 693 nM/805.8 | 3500 nM/4320 |
| FXa | 718 nM/834 | 1150 nM/1419.8 |

TABLE 2

Molecular weights of proteins in RP-HPLC pooled fractions

| Pool | A1 | A2 | A3 | A4 | B1 | B2 | C1 | D1 | D2 | E1 | E2 |
|---|---|---|---|---|---|---|---|---|---|---|---|
| Molecular Weight | 6970 | 6912/6811 | 7420/7421 | 7268 | 6977/6433 | 7268 | 6977/7307 | 7307/7133 | 6505 | 6363/6325 | 6373 |

The molecular weights of BF01 and BF02 are indicated by a text box.

TABLE 3

| Molecular weights of rFasxiator mutants | | | | | | | | |
|---|---|---|---|---|---|---|---|---|
| Mutants | N17A | N17R | N17K | L19A | L19M | R15A | R15P, P21R | N36F |
| Calculated MW | 7485.53 | 7570.64 | 7542.63 | 7486.48 | 7546.59 | 7443.45 | 7528.56 | 7561.63 |
| Determined MW | 7486 | 7571.8 | 7543.9 | 7487 | 7547.2 | 7444 | 7529 | 7562.2 |
| Mutants | N17R, L19A | N17R, L19E | N17R, L19F | N17R, L19N | N17R, L19R | N17R, L19S | | |
| Calculated MW | 7528.56 | 7586.6 | 7604.66 | 7571.58 | 7613.67 | 7544.56 | | |
| Determined MW | 7528.8 | 7586.8 | 7604.8 | 7572 | 7614.4 | 7545.5 | | |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An isolated peptide comprising the amino acid sequence of SEQ ID NO: 40.

2. The isolated peptide of claim 1 wherein the amino acid sequence of the peptide comprises SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

3. A pharmaceutical composition comprising the isolated peptide of claim 1.

4. The pharmaceutical composition of claim 3 wherein the amino acid sequence of the peptide comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

5. A method of reducing thrombogenesis in an individual in need thereof comprising administering an effective amount of all or a biologically active fragment thereof, one or more variants thereof, and/or one or more mutants thereof, wherein the peptide comprises the amino acid sequence of SEQ ID NO:40, and wherein the biologically active fragment thereof, one or more variant thereof, and/or one or more mutants thereof comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

6. The method of claim 5 wherein the peptide selectively inhibits FXIa.

7. The method of claim 5 wherein the thrombogenesis is a vein thrombosis, artery thrombosis or a combination thereof.

8. The method of claim 5 wherein the individual has undergone a cerebrovascular event, an ischemic stroke or a combination thereof.

9. The method of claim 5 wherein the peptide is administered to the individual before, after or during formation of a thrombus.

10. The method of claim 5 wherein the individual is a human.

11. A method of selectively inhibiting the intrinsic pathway of blood coagulation in an individual in need thereof comprising administering an effective amount of all or a biologically active fragment thereof, one or more variants thereof, and/or one or more mutants thereof to the individual, wherein the peptide comprises the amino acid sequence of SEQ ID NO:40 and wherein the biologically active fragment thereof, one or more variant thereof, and/or one or more mutants thereof comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

12. The method of claim 11 wherein the peptide selectively inhibits FXIa.

13. A method of selectively inhibiting FXI in an individual in need thereof comprising administering an effective amount of all or a biologically active fragment thereof, one or more variants thereof, and/or one or more mutants thereof to the individual, wherein the peptide comprises the amino acid sequence of SEQ ID NO:40, and wherein the biologically active fragment thereof, one or more variant thereof, and/or one or more mutants thereof comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

14. The method of claim 13 wherein the peptide selectively inhibits FXIa.

15. An isolated peptide consisting essentially of the amino acid sequence of SEQ ID NO: 12.

16. A pharmaceutical composition comprising the isolated peptide of claim 15.

17. A method of reducing thrombogenesis in an individual in need thereof comprising administering an effective amount of all or a biologically active fragment thereof, of the peptide of claim 15.

18. A method of selectively inhibiting the intrinsic pathway of blood coagulation in an individual in need thereof comprising administering an effective amount of all or a biologically active fragment thereof, of the peptide of claim 15.

19. A method of selectively inhibiting FXI in an individual in need thereof comprising administering an effective amount of all or a biologically active fragment thereof, of the peptide of claim 15.

* * * * *